(12) United States Patent
Bertoni et al.

(10) Patent No.: US 11,278,629 B2
(45) Date of Patent: Mar. 22, 2022

(54) METHODS FOR IMPROVING ANTI-CD37 IMMUNOCONJUGATE THERAPY

(71) Applicant: Debiopharm International, S.A., Lausanne (CH)

(72) Inventors: Francesco Bertoni, Bellinzona (CH); Angela Romanelli, Lexington, MA (US); Callum Sloss, Wakefield, MA (US)

(73) Assignee: DEBIOPHARM INTERNATIONAL, S.A., Lausanne (CH)

( * ) Notice: Subject to any disclaimer, the term of this patent is extended or adjusted under 35 U.S.C. 154(b) by 0 days.

(21) Appl. No.: 16/346,905

(22) PCT Filed: Nov. 2, 2017

(86) PCT No.: PCT/IB2017/056841
§ 371 (c)(1),
(2) Date: May 2, 2019

(87) PCT Pub. No.: WO2018/083633
PCT Pub. Date: May 11, 2018

(65) Prior Publication Data
US 2020/0054763 A1      Feb. 20, 2020

Related U.S. Application Data

(60) Provisional application No. 62/416,376, filed on Nov. 2, 2016.

(51) Int. Cl.
| A61K 47/68 | (2017.01) |
| A61K 9/00 | (2006.01) |
| A61K 39/395 | (2006.01) |
| A61K 39/00 | (2006.01) |
| A61K 31/573 | (2006.01) |
| A61K 38/19 | (2006.01) |
| C07K 16/28 | (2006.01) |

(52) U.S. Cl.
CPC ........ *A61K 47/6849* (2017.08); *A61K 9/0019* (2013.01); *A61K 31/573* (2013.01); *A61K 38/193* (2013.01); *A61K 39/3955* (2013.01); *A61K 47/6803* (2017.08); *A61K 47/6867* (2017.08); *C07K 16/2896* (2013.01); *A61K 2039/54* (2013.01); *A61K 2039/545* (2013.01)

(58) Field of Classification Search
CPC ...................... G01N 33/6893; G01N 2800/52
See application file for complete search history.

(56) References Cited

U.S. PATENT DOCUMENTS

| 5,122,368 | A |   | 6/1992 | Greenfield et al. |
| 5,595,756 | A | * | 1/1997 | Bally ............ A61K 9/1272 264/4.1 |
| 7,303,749 | B1 |  | 12/2007 | Chari |
| 7,585,491 | B2 |  | 9/2009 | Govindan |
| 7,601,354 | B2 |  | 10/2009 | Chari et al. |
| 7,989,598 | B2 |  | 8/2011 | Steeves et al. |
| 8,088,387 | B2 |  | 1/2012 | Steeves et al. |
| 8,765,917 | B2 |  | 7/2014 | Deckert et al. |
| 9,346,887 | B2 |  | 5/2016 | Deckert et al. |
| 9,447,189 | B2 |  | 9/2016 | Deckert et al. |
| 10,166,181 | B2 |  | 1/2019 | Ducrey et al. |
| 10,202,460 | B2 |  | 2/2019 | Deckert et al. |
| 10,556,958 | B2 |  | 2/2020 | Deckert et al. |
| 2003/0114398 | A1 |  | 6/2003 | Chatterjee et al. |
| 2004/0166115 | A1 |  | 8/2004 | Griffiths et al. |
| 2005/0136049 | A1 |  | 6/2005 | Ledbetter et al. |
| 2005/0287538 | A1 |  | 12/2005 | Cheung et al. |
| 2006/0039913 | A1 |  | 2/2006 | Das et al. |
| 2006/0233822 | A1 |  | 10/2006 | Xia et al. |
| 2006/0263349 | A1 |  | 11/2006 | McCutcheon et al. |
| 2007/0009519 | A1 |  | 1/2007 | Hariharan et al. |
| 2007/0059306 | A1 |  | 3/2007 | Grosmaire et al. |
| 2007/0237779 | A1 |  | 10/2007 | Ledbetter et al. |
| 2007/0270585 | A1 |  | 11/2007 | Chari et al. |
| 2008/0075726 | A1 |  | 3/2008 | Smith et al. |
| 2008/0226626 | A1 |  | 9/2008 | Hariharan et al. |
| 2008/0227198 | A1 |  | 9/2008 | Hariharan et al. |
| 2008/0279850 | A1 |  | 11/2008 | Brady et al. |
| 2009/0041783 | A1 |  | 2/2009 | Takayama et al. |
| 2009/0136516 | A1 |  | 5/2009 | Tedder et al. |
| 2009/0148447 | A1 |  | 6/2009 | Ledbetter et al. |
| 2009/0175867 | A1 |  | 7/2009 | Thompson et al. |
| 2009/0269336 | A1 |  | 10/2009 | Hong et al. |
| 2009/0274692 | A1 |  | 11/2009 | Tan et al. |

(Continued)

FOREIGN PATENT DOCUMENTS

| CN | 1446104 A | 10/2003 |
| CN | 1494433 A | 5/2004 |

(Continued)

OTHER PUBLICATIONS

Heppner et al. Tumor heterogenity: biological implications and therapeutic consequences. Cancer Metastasis Review 2:5-23; 1983 (Year: 1983).*
Jain RK. Barriers to drug delivery in solid tumors. Scientific American, Jul. 1994, 58-65 (Year: 1994).*
Awan, F., et al., "Phase 1 Study of TRU-016, an Anti-CD37 SMIP Protein in Naive and Relapsed and/or Refractory CLL Patients," ASH Annual Meeting 642: Abstract#1792 poster, p. 1, United States (Nov. 2011). Accessed at: https://ash.confex.com/ash/2011/webprogram/Paper39421.html on Jul. 20, 2015.
Colman, P.M., "Effects of Amino Acid Sequence Changes on Antibody-antigen Interactions," Research in Immunology 145(1):33-36, Elsevier, France (Jan. 1994).
Deckert, et al.,"Preclinical Mechanistic Studies Investigating Neutrophil and Lymphoid Cell Depletion by IMGN529, a CD37-Targeting Antibody-Drug Conjugate (ADC)," poster# 3119, 2 pages, 57th ASH Annual Meeting and Exposition, Dec. 6-9, 2014, San Francisco, United States.

(Continued)

Primary Examiner — Vanessa L. Ford
Assistant Examiner — Sandra E. Dillahunt
(74) Attorney, Agent, or Firm — Sterne, Kessler, Goldstein and Fox P.L.L.C.

(57) ABSTRACT

Methods for identifying and treating patients having cancer who are likely to respond to treatment with an anti-CD37 immunoconjugate (e.g., IMGN529) are provided.

26 Claims, 3 Drawing Sheets

Specification includes a Sequence Listing.

(56) References Cited

U.S. PATENT DOCUMENTS

| | | |
|---|---|---|
| 2009/0274713 A1 | 11/2009 | Chari et al. |
| 2010/0034820 A1 | 2/2010 | Ledbetter et al. |
| 2010/0135900 A1 | 6/2010 | Cerveny et al. |
| 2010/0189722 A1 | 7/2010 | Heider et al. |
| 2011/0256056 A1 | 10/2011 | Alper et al. |
| 2011/0256153 A1 | 10/2011 | Deckert et al. |
| 2012/0020963 A1 | 1/2012 | Banchereau et al. |
| 2012/0020983 A9 | 1/2012 | Braun et al. |
| 2012/0276119 A1 | 11/2012 | Deckert et al. |
| 2013/0058947 A1 | 3/2013 | Stull et al. |
| 2013/0295104 A1 | 11/2013 | Deckert et al. |
| 2014/0120083 A1 | 5/2014 | Stern et al. |
| 2014/0170063 A1 | 6/2014 | Govindan et al. |
| 2014/0348745 A1 | 11/2014 | Larsen et al. |
| 2015/0093397 A1 | 4/2015 | Carrigan |
| 2015/0343077 A1 | 12/2015 | Deckert et al. |
| 2016/0326258 A1 | 11/2016 | Deckert et al. |
| 2016/0340438 A1 | 11/2016 | Deckert et al. |
| 2017/0000900 A1 | 1/2017 | Romanelli et al. |
| 2018/0244795 A1 | 8/2018 | Deckert et al. |
| 2019/0183788 A1 | 6/2019 | Romanelli et al. |
| 2019/0218303 A1 | 7/2019 | Deckert et al. |
| 2020/0270361 A1 | 8/2020 | Deckert et al. |
| 2020/0330604 A1 | 10/2020 | Li et al. |
| 2021/0196835 A1 | 7/2021 | Rouits et al. |

FOREIGN PATENT DOCUMENTS

| | | | |
|---|---|---|---|
| CN | 1568198 A | 1/2005 | |
| EP | 0328147 B1 | 5/1994 | |
| JP | 2006513203 A | 4/2006 | |
| JP | 2016536298 A | 11/2016 | |
| WO | WO-0124763 A2 | 4/2001 | |
| WO | WO-0204021 A1 | 1/2002 | |
| WO | WO-02060484 A1 | 8/2002 | |
| WO | WO-02060485 A2 | 8/2002 | |
| WO | WO-02102972 A2 | 12/2002 | |
| WO | WO-03048306 A2 | 6/2003 | |
| WO | WO-03083069 A2 | 10/2003 | |
| WO | WO-2004058298 A1 | 7/2004 | |
| WO | WO-2005017148 A1 | 2/2005 | |
| WO | WO-2005037989 A2 | 4/2005 | |
| WO | WO-2005037992 A2 | 4/2005 | |
| WO | WO-2006074397 A2 | 7/2006 | |
| WO | WO-2006133450 A2 | 12/2006 | |
| WO | WO-2007014278 A2 | 2/2007 | |
| WO | WO-2007077173 A1 | 7/2007 | |
| WO | WO-2007140371 A2 | 12/2007 | |
| WO | WO-2007146968 A2 | 12/2007 | |
| WO | WO-2008052030 A2 | 5/2008 | |
| WO | WO-2008119567 A2 | 10/2008 | |
| WO | WO-2009019312 A2 | 2/2009 | |
| WO | WO-2009065576 A1 | 5/2009 | |
| WO | WO-2009085576 A2 | 7/2009 | |
| WO | WO-2009126858 A2 | 10/2009 | |
| WO | WO-2009126944 A1 | 10/2009 | |
| WO | WO-2009134977 A1 | 11/2009 | |
| WO | WO-2010008726 A1 | 1/2010 | |
| WO | WO-2010009124 A2 | 1/2010 | |
| WO | WO-2010126551 A1 | 11/2010 | |
| WO | WO-2011090754 A1 | 7/2011 | |
| WO | WO-2011090762 A1 | 7/2011 | |
| WO | WO-2011100398 A1 | 8/2011 | |
| WO | WO-2011100403 A1 | 8/2011 | |
| WO | WO-2011112978 A1 | 9/2011 | |
| WO | WO-2012135740 A2 | 10/2012 | |
| WO | WO-2013149171 A2 | 10/2013 | |
| WO | WO-2013171289 A1 | 11/2013 | |
| WO | WO-2014143807 A2 * | 9/2014 | ......... A61K 39/39558 |
| WO | WO-2014195460 A1 | 12/2014 | |
| WO | WO-2014197411 A1 * | 12/2014 | ......... C07K 16/2827 |
| WO | WO-2015038777 A1 | 3/2015 | |
| WO | WO-2015067586 A2 | 5/2015 | |
| WO | WO-2015116279 A2 * | 8/2015 | ......... H04B 10/2589 |
| WO | WO-2015116729 A2 * | 8/2015 | ......... C07K 16/2809 |
| WO | WO-2015175533 A2 | 11/2015 | |
| WO | WO-2016200676 A1 * | 12/2016 | ......... C07K 16/2887 |
| WO | WO-2017040247 A1 | 3/2017 | |
| WO | WO-2018083633 A1 | 5/2018 | |
| WO | WO-2019229677 A1 | 12/2019 | |

OTHER PUBLICATIONS

Gershoni, J.M., et al., "Epitope Mapping: the First Step in Developing Epitope-based Vaccines," BioDrugs 21(3):145-156, Springer International, New Zealand (2007).

Tutt, A., et al., "Trispecific F(ab')₃ Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).

Wang, L., et al., "Structural Characterization of the Maytansinoid-Monoclonal Antibody Immunoconjugate, huN901-DM1, by mass spectrometry," Protein Science, 14(9):2436-2446, Cold Spring Harbor Laboratory Press, United States (Sep. 2005).

Ackler, S., et al., "The Bcl-2 Inhibitor ABT-263 Enhances the Response of Multiple Chemotherapeutic Regimens in Hematologic Tumors in Vivo," Cancer Chemotherapy and Pharmacology 66(5):869-880, Springer Verlag, Germany (2010).

Algate, P., et al., "TRU-016, An Anti-CD37 SMIP (TM) Biologic, In combination with Other therapeutic Drugs in Models of Non-Hodgkin's Lymphoma," Blood 116(21):3931, American Society of Hematology, United States (Nov. 2010), 5 pages.

Alley, S.C., et al., "Antibody-drug Conjugates: Targeted Drug Delivery for Cancer," Current Opinion in Chemical Biology 14(4):529-537, Elsevier, England (2010).

Altschuler, E.P., et al., "Method for Obtaining Recombinant Antibodies and for Improving Affinities Thereof," Uspehi biologicheskoi himii 50: 203-258, Pleiades Publishing Ltd., Russia (Dec. 2010).

Altshuler, E.P., et al., "Generation of Recombinant Antibodies and Means for Increasing Their Affinity," Biochemistry 75(13):1584-1605, Pleiades Publishing, Ltd., United States (Dec. 2010).

Angeletti, R.H., "Design of Useful Peptide Antigens," Journal of Biomolecular Techniques 10(1):2-10, Association of Biomolecular Resource Facilities, United States (1999).

Angelisova, P., et al., "Association of Four Antigens of the Tetraspans Family (CD37, CD53, TAPA-1, and R2/C33) with MHC Class II Glycoproteins," Immunogenetics 39(4):249-256, Springer-Verlag, Germany (1994).

Awan, F.T., et al., "Phase 1 Study of TRU-016, an Anti-CD37 SMIP™ Protein in Naive and Relapsed and/or Refractory CLL Patients," Blood (ASH Annual Meeting Abstracts) 118(21):Abstract 1792, pp. 1-2, United States (Nov. 2011), Accessed at http://www.bloodjournal.org/content/118/21/1792.full.pdf on Dec. 2, 2015.

Awan, F., et al., "Phase 1 Study of TRU-016, an Anti-CD37 SMIP Protein in Naive and Relapsed and/or Refractory CLL Patients," Poster 1792, 1 page, 2011 American Society of Hematology Annual Meeting, Dec. 10 San Diego, United States.

Barrena, S., et al., "Aberrant Expression of Tetraspanin Molecules in B-cell Chronic Lymphoproliferative Disorders and its Correlation with Normal B-cell Maturation," Leukemia 19(8):1376-1383, Nature Publishing Group, England (2005).

Beckwith, K.A., et al.,"The CD37-Targeted Antibody-Drug Conjugate IMGN529 is Highly Active against Human CLL and in a Novel CD37 Transgenic Murine Leukemia Model," Leukemia 28(7):1501-1510, Nature Publishing Group, England (Jul. 2014).

Beers, S.A., et al., "Type II (Tositumomab) Anti-CD20 Monoclonal Antibody Out Performs Type I (Rituximab-Like) Reagents in B-Cell Depletion Regardless of Complement Activation," Blood 112(10):4170-4177, American Society of Hematology, United States (2008).

Bernstein, I.D., et al., "High Dose Radiolabeled Antibody Therapy of Lymphoma," Cancer Research 50(3 Suppl):1017s-1021s, American Association for Cancer Research, United States (1990).

Bissery, M., et al., "Experimental Antitumor Activity of Taxotere (RP 56976, NSC 628503), a Taxol Analogue," Cancer Research 51(18):4845-4852, American Association for Cancer Research, United States (1991).

(56) References Cited

OTHER PUBLICATIONS

Blanc, V., et al., "SAR3419: An Anti-CD19-Maytansinoid Immunoconjugate for the Treatment of B-Cell Malignancies," Clinical Cancer Research 17(20):6448-6458, American Association for Cancer Research, United States (2011).

Boross, P. and Leusen, J.H., "Mechanisms of Action of CD20 Antibodies," American Journal of Cancer Research 2(6):676-690, e-Century Publishing Corporation, United States (2012).

Braslawsky, G.R., et al., "Antitumor Activity of Adriamycin (hydrazone-linked) Immunoconjugates Compared with Free Adriamycin and Specificity of Tumor Cell Killing," Cancer Research 50(20):6608-6614, American Association for Cancer Research, United States (1990).

Business Wire, "ImmunoGen, Inc. Announces Presentations at the 102nd Annual Meeting of the American Associated for Cancer Research," May 30, 2011, accessed at http://files.shareholder.comjdownloads/ABEA-5VU3S1/0x0x500536/b6f7f6a6-1853-4476-93cf-2f2f895241d7/1MGN News_2011_3_30_General_Releases.pdf, accessed on Dec. 8, 2014.

Chen, R., et al., "A Phase II Study of Vorinostat and Rituximab for Treatment of Newly Diagnosed and Relapsed/refractory Indolent Non-hodgkin Lymphoma," Haematologica 100(3):357-362, Ferrata Storti Foundation, Italy (Mar. 2015).

Cheson, B.D., et al., "Revised Response Criteria for Malignant Lymphoma," Journal of Clinical Oncology 25(5):579-586, American Society of Clinical Oncology, United States (2007).

Co, M.S., et al., "Chimeric and Humanized Antibodies With Specificity for the CD33 Antigen," Journal of immunology, 148(4):1149-1154., American Association of Immunologists, United States (Feb. 1992).

Cragg, M.S., et al., "Complement-mediated Lysis by Anti-CD20 mAb Correlates with Segregation into Lipid Rafts," Blood 101(3):1045-1052, American Society of Hematology, United States (Feb. 2003).

Dahle, J., et al., "Evaluating Antigen Targeting and Anti-tumor Activity of a New Anti-CD37 Radioimmunoconjugate Against Non-Hodgkin's Lymphoma," Anticancer Research 33(1):85-96, International Institute of Anticancer Research, Greece (2013).

Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Episodes and Peptide Immunogenicity Is Drastically Influenced by the Nature of the Protein Carrier," Virology 202:540-549, Elsevier Inc., Netherlands (1994).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

Deckert, et al., IMGN529, a Novel Antibody-Dmg Conjugate (ADC) Targeting CD37 Shows Synergistic Activity with Rituximab in Non-Hodgkin Lymphoma (NHL) Models, poster# 1548. 1 page, 57th ASH Annual Meeting and Exposition, Dec. 5, 2015, Orlando, United States.

Deckert, et al., "Preclinical Mechanistic Studies Investigating Neutrophil and Lymphoid Cell Depletion by IMGN529, a CD37-Targeting Antibody-Drug Conjugate (ADC)," poster# 3119. 1 page, 57th ASH Annual Meeting and Exposition, Dec. 6-9, 2014, San Francisco, United States.

Deckert, J., et al., "A Novel Anti-CD37 Antibody-Drug Conjugate with Multiple Anti-tumor Mechanisms for the Treatment of B-Cell Malignancies," Blood 122(20):3500-3510 American Society of Hematology, United States (2013).

Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23):1548, 5 pages, American Society of Hematology, United States (2015).

Deckert, J., et al., "IMGN529: A Therapeutic Maytansinoid Conjugate of an Anti-CD37 Antibody with Multiple Mechanisms of Action for B-cell Lymphoma and Leukemia," AACR Poster Abstract #2, United States, Apr. 2-6, 2011.

Deckert, J., et al., "IMGN529: An Anti-CD37 Antibody-Maytansinoid Conjugate with Multiple Mechanisms of Actions for B-Cell Malignancies," Keystone Symposhis—B Cells: New Insights into Normal versus Dysregulated Function, Apr. 12-16, 2011, Poster#306, United States (Apr. 2011).

Deckert, J., et al., "Potent B-Cell Depletion by IMGN529, a CD37-Targeting Antibody-Maytansinoid Conjugate for the Treatment of B-Cell Malignancies," American Society of Hematology 2011, Abstract #3726, pp. 1-2, United States (Nov. 2011).

Deckert, J., et al., "Preclinical Mechanistic Studies Investigating Neutrophil and Lymphoid Cell Depletion by IMGN529, a CD37-Targeting Antibody-Drug Conjugate (ADC)," 56th American Society of Hematology Annual Meeting and Exposition: Abstract# 3119, 2 pages, United States (Dec. 2014) Accessed at https://ash.confex.com/ash/2014/webprogram/Paper70777.html on Aug. 26, 2015.

Deckert, J., et al., "Preclinical Mechanistic Studies Investigating Neutrophil and Lymphoid Cell Depletion by IMGN529, a CD37-Targeting Antibody-Drug Conjugate (ADC)," 56th American Society of Hematology Annual Meeting and Exposition: Poster p. 1, Abstract# 3119, Accessed at http://www.immunogen.com/documents/Publications/IMGN529%20preclinical%20ASH%2012-2014.pdf on Aug. 26, 2015.

Dijoseph, J.F., et al., "CD20-specific Antibody-targeted Chemotherapy of Non-Hodgkin's B-cell Lymphoma Using Calicheamicin-conjugated Rituximab," Cancer Immunol Immunother 56(7):1107-1117, Springer-Verlag, Germany (2007).

Ducry, L., et al., "Antibody-Drug Conjugates: Linking Cytotoxic Payloads to Monoclonal Antibodies," Bioconjugate 21:5-13, American Chemical Society, United States (2009).

Epstein, A.L., et al., "Two New Monoclonal Antibodies, Lym-1 and Lym-2, Reactive With Human B-lymphocytes and Derived Tumors, With Immunodiagnostic and Immunotherapeutic Potential," Cancer Research 47(3):830-840, American Association for Cancer Research, United States (Feb. 1987).

Epstein, A.L., et al., "Two New Monoclonal Antibodies (LN-1, LN-2) Reactive in B5 Formalin-fixed, Paraffin-embedded Tissues with Follicular Center and Mantle Zone Human B Lymphocytes and Derived Tumors," Journal of Immunology 133(2):1028-1036, American Association of Immunologists, United States (1984).

Eugenio, G., et al., Identification of anti-lymphoma biomarkers of response to the anti-cd37 antibody drug conjugate (ADC) IMGN529, presented at 58th Annual Meeting and Exposition of the American Society of Hematology 128, 1 page (2016).

Extended European Search Report and Written Opinion for EP Application No. 13 77 0074, The Hague, Netherlands, completed on Oct. 20, 2015, pp. 1-9.

Friedberg, J.W., "Double-Hit Diffuse Large B-cell Lymphoma," Journal of Clinical Oncology 30(28):3439-3443, American Society of Clinical Oncology, United States (2012).

Goel, M., et al., "Plasticity Within the Antigen-combining Site May Manifest as Molecular Mimicry in the Humoral Immune Response," Journal of Immunology 173(12):7358-7367, American Association of Immunologists, United States (Dec. 2004).

Gopal, A., et al., "Phase 1b Study of otlertuzumab (TRU-016), an Anti-CD37 monospecific ADAPTIR™ therapeutic protein, in Combination with Rituximab and Bendamustine in Relapsed Indolent Lymphoma patients," Investigational New Drugs Presented at ASH annual meeting 2012, 13 pages.

Green, T.M., et al., "Immunohistochemical Double-Hit Score Is a Strong Predictor of Outcome in Patients with Diffuse Large B-cell Lymphoma Treated with Rituximab Plus Cyclophosphamide, Doxorubicin, Vincristine, and Prednisone," Journal of Clinical Oncology 30(28):3460-3467, American Society of Clinical Oncology, United States (2012).

Greenfield, R.S., et al., "Evaluation in Vitro of Adriamycin Immunoconjugates Synthesized Using an Acid-sensitive Hydrazone Linker," Cancer Research 50(20):6600-6607, American Association for Cancer Research, United States (1990).

Greenspan, N.S. and Di Cera, E., "Defining Epitopes: It's not as Easy as it Seems," Nature Biotechnology 17(10):936-937, Nature Publishing Group, United States (1999).

(56) References Cited

OTHER PUBLICATIONS

Gross, J., "3333:Evaluation of Otlertuzumab (TRU-016), an Anti-CD37 ADAPTIR™ Therapeutic in Preclinical Combination Studies with Kinase Inhibitors and a Next Generation Anti-CD20 Mab in Vitro and in Animal Models of Non-Hodgkin's Lymphoma," Blood 124(21):3333, 2 pages, American Society of Hematology, United States (2014).
Gussow, D. and Seemann, G., "Humanization of Monoclonal Antibodies," Methods in Enzymology 203:99-121, Elsevier Science, United States (1991).
Harris, C.L., et al., "Tumour Cell Killing Using Chemically Engineered Antibody Constructs Specific for Tumour Cells and the Complement Inhibitor CD59," Clinical & Experimental Immunology 107(2):364-371, Blackwell Publishing, England (1997).
Heider, K.H., et al., "A Novel Fc-engineered Monoclonal Antibody to CD37 with Enhanced ADCC and High Proapoptotic Activity for Treatment of B-cell Malignancies," Blood 118(15):4159-4168, The American Society of Hematology, United States (2011).
Hicks, S.W., et al., "The Antitumor Activity of Imgn529, a Cd37-targeting Antibody-drug Conjugate, Is Potentiated by Rituximab in Non-hodgkin Lymphoma Models," Neoplasia 19(9):661-671, Neoplasia Press, United States (Sep. 2017).
Hu, S., et al., "MYC/BCL2 Protein Coexpression Contributes to the Inferior Survival of Activated B-Cell Subtype of Diffuse Large B-Cell Lymphoma and Demonstrates High-Risk Gene Expression Signatures: a Report from The International DLBCL Rituximab-CHOP Consortium Program," Blood 121(20):4021-4031, American Society of Hematology, United States (2013).
International Preliminary Report on Patentability for International Application No. PCT/US2012/031648, The International Bureau of WIPO, Switzerland, dated Oct. 2, 2013, pp. 1-9.
International Preliminary report on patentability for International Application No. PCT/US2016/035558, International search authority, Switzerland, dated Dec. 12, 2017, 8 pages.
International Preliminary Report on Patentability for International Application No. PCT/US2016/048887,International Searching Authority, United States, dated Nov. 29, 2016, 5 pages.
International Search Report and Written Opinion for International Application No. PCT/US11/28172, International Searching Authority, United States, dated Jul. 13, 2011, pp. 1-9.
International Search Report and Written Opinion for International Application No. PCT/US12/31648, Commissioner for Patents, United States, dated Sep. 20, 2012, 16 pages.
International Search Report and Written Opinion for International Application No. PCT/US15/30371, Commissioner for Patents, United States, dated Nov. 2, 2015, pp. 1-10.
International Search Report and Written Opinion for International Application No. PCT/US2013/034646, Commissioner for Patents, United States, dated Sep. 16, 2013, pp. 1-15.
International Search Report and Written Opinion for International Application No. PCT/US2016/035558, Commissioner for Patents, United States, dated Sep. 7, 2016, 11 pages.
International Search Report and Written Opinion for International Application No. PCT/US2016/048887, Commissioner for Patents, United States, dated Nov. 29, 2016, 8 pages.
International Search Report with Written Opinion for International Application No. PCT/IB2017/056841, International Searching Authority, Netherlands, dated Feb. 2, 2018, 10 pages.
Kaminski, M.S., et al., "Imaging, Dosimetry, and Radioimmunotherapy with Iodine 131-labeled Anti-CD37 Antibody in B-cell Lymphoma," Journal of Clinical Oncology 10(11):1696-1711, American Society of Clinical Oncology, United States (1992).
Khan, T and Salunke, D.M, "Adjustable Locks and Flexible Keys: Plasticity of Epitope-paratope Interactions in Germline Antibodies," Journal of Immunology 192(11):5398-5405, American Association of Immunologists, United States (Jun. 2014).
Knobeloch, K.P., et al. ."Targeted Inactivation of the Tetraspanin CD37 Impairs T-cell-dependent B-cell Response Under Suboptimal Costimulatory Conditions," Molecular and Cellular Biology 20(15):5363-5369, American Society for Microbiology, United States (2000).
Konig, A., et al., "Basic Fibroblast Growth Factor (bFGF) Upregulates the Expression of bcl-2 in B Cell Chronic Lymphocytic Leukemia Cell Lines Resulting in Delaying Apoptosis," Leukemia 11(2):258-265, Nature Publishing Group, England (1997).
Kovtun, Y., et al., "Antibody-Maytansinoid Conjugates Designed to Bypass Multidrug Resistance," Cancer Research 70(6):2528-2537, American Association for Cancer Research, United States (Mar. 2010).
Lai, K.C., et al., "Evaluation of Targets for Maytansinoid ADC Therapy Using a Novel Radiochemical Assay," Pharmaceutical Research 32(11):3593-3603, Kluwer Academic, United States (2015).
Lai, K.C., et al., "The CD37-targeting ADC IMGN529 Combines the Potent Anti-cancer Activity of K7153A Antibody with Efficient Maytansinoid Delivery," AACR-EORTC-NCI 2011, Poster, 1 page, United States (Nov. 2011).
Lai, K.C., et al., "The CD37-targeting ADC IMGN529 Combines the Potent Anti-cancer Activity of K7153A Antibody with Efficient Maytansinoid Delivery," AACR-EORTC-NCI 2011, Poster Abstract #B209, p. 1, United States (Nov. 2011).Accessed at: http://mct.aacrjournals.org/content/10/11_Supplement/B209.short on Jul. 20, 2015.
Lai, K.C., et al., "The CD37-targeting ADC IMGN529 Combines the Potent Anti-cancer Activity of K7153A Antibody with Efficient Maytansinoid Delivery," Oasis, The Online Abstract Submission System, Abstract 11-A-226-AACR:pp. 1-2, Molecular Targets and Cancer Therapeutics, Nov. 12-16, 2011, San Francisco, United States (Nov. 2011). Accessed at http://www.abstractsonline.com/plan/viewabstract.aspx?mid=2889&skey=946d141d-1376-4bec-8e3f-a54580b89072&ckey=5af84375-1153-46e6-974c-e95ea6225aef&mkey=%7Ba57ff86d-d414-4079-bcbd-157746574f37%7D on Jul. 16, 2015.
Lambert, J.M., "Antibody-Maytansinoid Conjugates: A New Strategy for the Treatment of Cancer," Drugs of the Future 35(6):471-480, Prous Science, S.A.U., Spain (Jun. 2010).
Lapalombella, R., et al., "Tetraspanin CD37 Directly Mediates Transduction of Survival and Apoptotic Signals," Cancer Cell 21(5):694-708, Elsevier Inc., United States (2012).
Lim, S.H., et al., "Anti-CD20 Monoclonal Antibodies: Historical and Future Perspectives," Haematologica 95(1):135-143, Ferrata Storti Foundation, Italy (Jan. 2010).
Link, M.P., et al., "A Unique Antigen on Mature B Cells Defined by a Monoclonal Antibody," The Journal of Immunology 137(9):3013-3018, The American Association of Immunologists, United States (1986).
Lippincott-Schwartz, J., "Antibodies as Cell Biological Tools," Current Protocols in Cell Biology, 16.0.1-16.0.2, 2002.
MacCallum, R.M., et al., "Antibody-antigen Interactions: Contact Analysis and Binding Site Topography," Journal of Molecular Biology 262(5):732-745, Academic Press, England (Oct. 1996).
Maecker, H.T., et al., "The Tetraspanin Superfamily: Molecular Facilitators," FASEB Journal 11(6):428-442, FASEB, United States (1997).
Mariuzza, R.A., et al., "The Structural Basis of Antigen-antibody Recognition," Annual Review of Biophysics and Biomolecular Structure 16:139-159, Annual Reviews, United States (1987).
Marken, U.S., et al., "Membrane Topology of the L6 Antigen and Identification of the Protein Epitope Recognized by the L6 Monoclonal Antibody," The Journal of Biological Chemistry 269(10):7397-7401, American Society for Biochemistry and Molecular Biology, United States (1994).
Meyer-Wentrup, F., et al., "Dectin-1 Interaction with Tetraspanin CD37 Inhibits IL-6 Production," The Journal of Immunology 178(1):154-162, The American Association of Immunologists, Inc., United States (2007).
Moore, K., et al., "Use of the Monoclonal Antibody WR17, Identifying the CD37 gp40-45 Kd Antigen Complex, in the Diagnosis of B-lymphoid Malignancy," Journal of Pathology 152(1):13-21, John Wiley & Sons, Ltd., England (1987).

(56) References Cited

OTHER PUBLICATIONS

Morris, G.E., "Epitope Mapping of Protein Antigens by Competition ELISA," The Protein Protocols Handbook 1:595-600, Humana Press, United States (1996).
NCT01534715, "IMGN529 in Treating Patients with Relapsed or Refractory Non-Hodgkin's Lymphoma," retrieved from https://clinical.gov/archive/NCT01534715/2012_02_16, retrieved on Sep. 6, 2016, 2 pages.
Oki, Y., et al., "Pegylated Liposomal Doxorubicin Replacing Conventional Doxorubicin in Standard R-chop Chemotherapy for Elderly Patients With Diffuse Large B-cell Lymphoma: an Open Label, Single Arm, Phase II Trial," Clinical Lymphoma, Myeloma & Leukemia 15(3); 152-158, Elsevier, United States (Mar. 2015).
Pagel, J.M, et al., "Phase 1 Study of TRU-016, An Anti-CD37 SMIP™ Protein in Relapsed and/or Refractory NHL Patients," Blood (ASH Annual Meeting Abstracts) 2011 118(21):Abstract 1636, 2 pages, The American Society of Hematology, United States (2011).
Park, P.U., et al., "Antibody and Linker Selection for the Anti-CD37 Antibody-maytansinoid Conjugate IMGN529 for the Treatment of B-cell Malignancies," Experimental and Molecular Therapeutics Session, AACR Annual Meeting 2011, Experimental and Molecular Therapeutics session, Abstract #2830:1-24, United States (Apr. 2011). Accessed at http://cancerres.accrjournals.org/content/71/8_Supplement/2830.abstract on Jul. 20, 2015.
Paul, W.E., "Immunogenicity and Antigen Structure," in Fundamental Immunology, Third Edition, pp. 242, Raven Press, United States (1993).
Pers, J.O., et al., "Anti-CD20 Antibody-Mediated Apoptosis of B Cells Is a Lipid Raft-Dependent Process," Annals of the Rheumatic Diseases 70(Suppl 2):A73, BMJ Publishing Group Ltd (Feb. 2011).
Pinkas, J., "Antibody Maytansinoid Conjugates for the Treatment of Cancer," Protein Therapeutics Forum 2012:1-23, Jan. 30, 2012, United States (Jan. 2012).
Polson, A.G., et al., "Antibody-drug Conjugates for the Treatment of Non-Hodgkin's Lymphoma: Target and Linker-drug Selection," Cancer Research 69(6):2358-2364, American Association for Cancer Research, United States (2009).
Poosarla, V.G., et al., "Computational De Novo Design of Antibodies Binding to a Peptide With High Affinity," Biotechnology and Bioengineering 114(6):1331-1342, Wiley, United States (Jun. 2017).
Preissuance Submission by Third Party under 37 C.F.R. § 1.290 in U.S. Appl. No. 13/045,693 (inventors Deckert et al., filed Mar. 11, 2011) dated May 30, 2013, 14 pages.
Preissuance Submission by Third Party under 37 C.F.R. § 1.290 in U.S. Appl. No. 13/436,528 (inventors Deckert et al.,filed Mar. 30, 2012), dated Aug. 26, 2013, 15 pages.
Preissuance Submission by Third Party under 37 C.F.R. § 1.290 in U.S. Appl. No. 13/796,768 (inventors Deckert et al., filed Mar. 12, 2013), dated Apr. 1, 2014, 18 pages.
Press, O.W., et al., "Endocytosis and Degradation of Monoclonal Antibodies Targeting Human B-cell Malignancies," Cancer Research 49(17):4906-4912, American Association for Cancer Research, United States (1989).
Press, O.W., et al., "Radiolabeled-antibody Therapy of B-cell Lymphoma with Autologous Bone Marrow Support," The New England Journal of Medicine 329(17):1219-1224, Massachusetts Medical Society, United States (1993).
Press, O.W., et al., "Retention of B-cell-specific Monoclonal Antibodies by Human Lymphoma Cells," Blood 83(5):1390-1397, The American Society of Hematology, United States (1994).
Press, O.W., et al., "Treatment of Refractory Non-Hodgkin's Lymphoma with Radiolabeled MB-1 (anti-CD37) Antibody," Journal of Clinical Oncology 7(8):1027-1038, American Society of Clinical Oncology, United States (1989).
Robak, T. and Robak, E., "New Anti-CD20 Monoclonal Antibodies for the Treatment of B-cell Lymphoid Malignancies," BioDrugs 25(1):13-25, Springer International, New Zealand (Feb. 2011).
Robak, T., et al., "TRU-016, a Humanized Anti-CD37 IgG Fusion Protein for the Potential Treatment of B-cell Malignancies," Current Opinion in Investigational Drugs 10(12):1383-1390, Thomson Reuters Ltd., England (2009).
Roguska, M.A., et al., "A Comparison of Two Murine Monoclonal Antibodies Humanized by CDR-grafting and Variable Domain Resurfacing," Protein Engineering 9(10):895-904, Oxford University Press, England (1996).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Romanelli, A., et al., Novel CD37-Targeting Antibody-Drug Conjugate (ADC), IMGN529, Has Synergistic Activity in Combination with Rituximab in Non-Hodgkin Lymphoma (NHL) Models, presented at 13th International Conference on Malignant Lymphoma, Jun. 17-20, 2015, 1 page.
Rops, A.L., et al., "The Tetraspanin CD37 Protects Against Glomerular IgA Deposition and Renal Pathology," American Journal of Pathology 176(5):2188-2197, American Society for Investigative Pathology, United States (May 2010).
Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).
Rudolph, C., et al., "Molecular Cytogenetic Characterization of the Mantle Cell Lymphoma Cell Line GRANTA-519," Cancer Genetics and Cytogenetics 153(2):144-150, Elsevier, United States (2004).
Schwartz-Albiez, R., et al., "The B Cell-associated CD37 Antigen (gp40-52). Structure and Subcellular Expression of an Extensively Glycosylated Glycoprotein," The Journal of Immunology 140(3):905-914, The American Association of Immunolmists, United States (1988).
Sheng, K-C., et al., "Tetraspanins CD37 and CD151 Differentially Regulate Ag Presentation and T-cell co-stimulation by DC," European Journal of Immunology 39(1):50-55, Wiley-VCH Verlag GmbH & Co. KGaA, Germany (2009).
Smith, S.M., et al., "The Impact of MYC Expression in Lymphoma Biology: Beyond Burkitt Lymphoma," Blood Cells, Molecules and Diseases 45(4):317-323, Academic Press, United States (Dec. 2010).
Smith, T.J., et al., "2006 Update of Recommendations for the Use of White Blood Cell Growth Factors: An Evidence-based Clinical Practice Guideline," Journal of Clinical Oncology 24(19):3187-3205, American Society of Clinical Oncology, United States (2006).
Smolewski, P., et al., "Pro-apoptotic Effect of an Anti-cd37 Scfv-fc Fusion Protein, in Combination With the Anti-cd20 Antibody, Ofatumumab, on Tumour Cells From B-cell Malignancies," European Journal of Cancer 50(15):2677-2684, Elsevier, Netherlands (Oct. 2014).
Stathis, A. et al.,"Preliminary Findings from a Phase I, Multi-center, Open-label Study of the anti-CD37 Antibody-Drug Conjugate (ADC), IMGN529, in Adult Patients with Relapsed or Refractory Non-Hodgkin Lymphoma (NHL)," 2014 ASCO Annual Meeting, Poster, Abstract No. 8526, United States (May 2014), 1 page Accessed at http://www.immunogen.com/documents/Publications/IMGN529%20first%20clin%20ASCO%202014.pdf on Aug. 26, 2015.
Stathis, A. et al., "A Phase I Study of IMGN529, An Antibody-Drug Conjugate (ADC) Targeting CD37, In Adult Patients With Relapsed or Refractory Non-Hodgkin Lymphoma (NHL)," 56th American Society of Hematology Annual Meeting and Exposition: Abstract#1760, United States (Dec. 2014), 1 page Accessed at https://ash.confex.com/ash/2014/webprogram/Paper70219.html, on Aug. 26, 2015.
Stathis, A. et al., "A Phase I Study of IMGN529, An Antibody-Drug Conjugate (ADC) Targeting CD37, In Adult Patients With Relapsed or Refractory Non-Hodgkin Lymphoma (NHL)," Abstract#1760, American Society of Hematology Annual Meeting, San Francisco, California, United States (Dec. 2014), 2 pages, accessed at http://www.immunogen.com/documents/Publications/IMGN529_Phl_ASH12-2014.pdf, accessed on Aug. 26, 2015.
Stathis, A., et al., "Safety, Tolerability, and Preliminary Activity of IMGN529, a CD37-Targeted Antibody-Drug Conjugate, In Patients with Relapsed or Refractory B-Cell Non-Hodgkin Lymphoma: a

(56) References Cited

OTHER PUBLICATIONS

Dose-Escalation, Phase I Study, " Invest New Drugs, 36(5):869-876, Springer, United States (Oct. 2018).
Supplementary European Search Report for Application No. EP11754195, dated Sep. 10, 2013, 7 pages.
Tedder, T.F., et al., "Structure of the Gene Encoding the Human B Lymphocyte Differentiation Antigen CD20 (B1)," The Journal of Immunology 142(7):2560-2568, The American Association of Immunologists, United States (1989).
Tedoldi, S., et al., "Selective Loss of B-Cell Phenotype in Lymphocyte Predominant Hodgkin Lymphoma," Pathology 213(4):429-440, John Wiley and Sons, England, (Dec. 2007).
Teicher, B.A. and Chari, R.V.J., "Antibody Conjugate Therapeutics: Challenges and Potential," Clinical Cancer Research 17(20):6389-6397, American Association for Cancer Research, United States (Oct. 2011).
Tomayko. M.M. and Reynolds, C.P., "Determination of Subcutaneous Tumor Size in Athymic (Nude) Mice," Cancer Chemotherapy and Pharmacology 24(3):148-154, Springer Verlag, Germany (1989).
Van Spriel, A.B., et al., "A Regulatory Role for CD37 in T Cell Proliferation," The Journal of Immunology 172 (5):2953-2961, The American Association of Immunologists, United States (2004).
Van Spriel, A.B., et al., "The Tetraspanin Protein CD37 Regulates IgA Responses and Anti-Fungal Immunity," PLoS Pathogens 5(3) e1000338:1-11, Public Library of Science, United States (2009).
Wang, Z., et al., "Universal Pcr Amplification of Mouse Immunoglobulin Gene Variable Regions: the Design of Degenerate Primers and an Assessment of the Effect of DNA Polymerase 3' to 5' Exonuclease Activity," Journal of Immunological Methods 233(1-2):167-177,Elsevier, Netherlands (Jan. 2000).
Yu, B., et al., "Targeted Drug Delivery and Cross-Linking Induced Apoptosis with Anti-CD37 based Dual-Ligand Immunoliposomes in B Chronic Lymphocytic Leukemia Cells," Biomaterials 34(26):6185-6193, Elsevier Science, Netherlands (2013).
Zenz, T. et al., "Exceptional In Vitro Activity of CD37 Antibodies in CLL," Blood 116(21): 1021-1022, 2010 ASH Annual Meeting Abstracts (Abstract 2460), American Society of Hematology, United States (2010), 5 pages, accessed at https://ashconfex.com/ash/2010/webprogram/Paper29401.html, accessed on Apr. 4, 2016.
Zhao, X., et al., "CD37 is a Potential Therapeutic Target for B-Cell Non-Hodgkin Lymphoma," Blood, 116(21), 3 pages, American Society of Hematology, United States (Nov. 2011); 52nd Annual Meeting of the American Society of Hematology (Ash); United States; Dec. 4-7, 2010 Accessed at https://ash.confex.com/ash/2010/webprogram/Paper28315.html, on Nov. 13, 2015.
Zhao, X., et al., "CD37 Is a Potential Therapeutic Target for B-Cell Non-Hodgkin Lymphoma," Blood: 2010 ASH Annual Meeting Abstracts 116(21):1277-1278, Abstract No. 3098, American Society of Hematology, United States (Nov. 19, 2010).
Zhao, X., "Targeting CD37 and folate receptor for cancer therapy: strategies based on engineered proteins and liposomes," Europe PubMed Central, accessed at http://europepmc.org/theses/ETH/6183, accessed on Dec. 9, 2014 (2007) [Thesis 6183], pp. 1-296.
Zhao, X.B., et al., "Novel Anti-CD37 Small Modular Immunopharmaceutical (SMP) Induces B-Cell-Specific, Caspase-Independent Apoptosis in Human CLIJ Cells," Blood 104, Abstract 2515, p. 1, ASH Annual Meeting, American Society of Hematology, United States (2004). Accessed at http://abstracts.hematologylibrary.org/cgi/content/short/104/11/2515 on Jul. 16, 2015.
Zhao, X.B. et al., "Targeting CD37-positive Lymphoid Malignancies with a Novel Engineered Small Modular Immunopharmaceutical," Blood 110(7):2569-2577, The American Society of Hematology, United States (2007).
Levy, M. Y., et al., "Safety and efficacy of CD37-Targeting Naratuximab Emtansine plus Rituximab in Diffuse Large B-cell Lymphoma and Other Non-Hodgkin's B-cell Lymphomas—a Phase 2 Study," Poster #244, presented at the 16th International Conference on Malignant Lymphoma (Virtual Edition), June 18-22, 2021, Hematological Oncology, John Wiley & Sons, Inc., United States, accessed at URL: [https://www.debiopharm.com/drug-development/publications/safety-and-efficacy-of-cd37-targeting-naratuximab-emtansine-plus-rituximab-in-diffuse-large-b-cell-lymphoma-and-other-non-hodgkins-b-cell-lymphomas-a-phase-2-study/]on July 16, 2021, 1 page (June 2021).

\* cited by examiner

SEQUENCE LISTING

<160> NUMBER OF SEQ ID NOS: 70

<210> SEQ ID NO 1
<211> LENGTH: 281
<212> TYPE: PRT
<213> ORGANISM: Homo Sapiens

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 2
<211> LENGTH: 281
<212> TYPE: PRT
<213> ORGANISM: Macaca mulatta

<400> SEQUENCE: 2

Met Ser Ala Gln Glu Ser Cys Leu Ser Leu Ile Lys Tyr Phe Leu Phe
1               5                   10                  15

Val Phe Asn Leu Phe Phe Phe Val Ile Leu Gly Ser Leu Ile Phe Cys
            20                  25                  30

Phe Gly Ile Trp Ile Leu Ile Asp Lys Thr Ser Phe Val Ser Phe Val

```
            35                  40                  45
Gly Leu Ala Phe Val Pro Leu Gln Ile Trp Ser Lys Val Leu Ala Ile
 50                  55                  60

Ser Gly Val Phe Thr Met Gly Leu Ala Leu Leu Gly Cys Val Gly Ala
 65                  70                  75                  80

Leu Lys Glu Leu Arg Cys Leu Leu Gly Leu Tyr Phe Gly Met Leu Leu
                 85                  90                  95

Leu Leu Phe Ala Thr Gln Ile Thr Leu Gly Ile Leu Ile Ser Thr Gln
                100                 105                 110

Arg Ala Gln Leu Glu Arg Ser Leu Gln Asp Ile Val Glu Lys Thr Ile
                115                 120                 125

Gln Arg Tyr His Thr Asn Pro Glu Glu Thr Ala Ala Glu Glu Ser Trp
            130                 135                 140

Asp Tyr Val Gln Phe Gln Leu Arg Cys Cys Gly Trp His Ser Pro Gln
145                 150                 155                 160

Asp Trp Phe Gln Val Leu Thr Leu Arg Gly Asn Gly Ser Glu Ala His
                165                 170                 175

Arg Val Pro Cys Ser Cys Tyr Asn Leu Ser Ala Thr Asn Asp Ser Thr
                180                 185                 190

Ile Leu Asp Lys Val Ile Leu Pro Gln Leu Ser Arg Leu Gly Gln Leu
                195                 200                 205

Ala Arg Ser Arg His Ser Thr Asp Ile Cys Ala Val Pro Ala Asn Ser
            210                 215                 220

His Ile Tyr Arg Glu Gly Cys Ala Arg Ser Leu Gln Lys Trp Leu His
225                 230                 235                 240

Asn Asn Leu Ile Ser Ile Val Gly Ile Cys Leu Gly Val Gly Leu Leu
                245                 250                 255

Glu Leu Gly Phe Met Thr Leu Ser Ile Phe Leu Cys Arg Asn Leu Asp
                260                 265                 270

His Val Tyr Asn Arg Leu Arg Tyr Arg
            275                 280

<210> SEQ ID NO 3
<211> LENGTH: 281
<212> TYPE: PRT
<213> ORGANISM: Mus musculus

<400> SEQUENCE: 3

Met Ser Ala Gln Glu Ser Cys Leu Ser Leu Ile Lys Tyr Phe Leu Phe
 1               5                  10                  15

Val Phe Asn Leu Phe Phe Val Leu Gly Gly Leu Ile Phe Cys Phe
                 20                  25                  30

Gly Thr Trp Ile Leu Ile Asp Lys Thr Ser Phe Val Ser Phe Val Gly
                 35                  40                  45

Leu Ser Phe Val Pro Leu Gln Thr Trp Ser Lys Val Leu Ala Val Ser
 50                  55                  60

Gly Val Leu Thr Met Ala Leu Ala Leu Leu Gly Cys Val Gly Ala Leu
 65                  70                  75                  80

Lys Glu Leu Arg Cys Leu Leu Gly Leu Tyr Phe Gly Met Leu Leu Leu
                 85                  90                  95

Leu Phe Ala Thr Gln Ile Thr Leu Gly Ile Leu Ile Ser Thr Gln Arg
                100                 105                 110

Val Arg Leu Glu Arg Arg Val Gln Glu Leu Val Leu Arg Thr Ile Gln
                115                 120                 125
```

```
Ser Tyr Arg Thr Asn Pro Asp Glu Thr Ala Ala Glu Glu Ser Trp Asp
    130                 135                 140
Tyr Ala Gln Phe Gln Leu Arg Cys Cys Gly Trp Gln Ser Pro Arg Asp
145                 150                 155                 160
Trp Asn Lys Ala Gln Met Leu Lys Ala Asn Glu Ser Glu Glu Pro Phe
                165                 170                 175
Val Pro Cys Ser Cys Tyr Asn Ser Thr Ala Thr Asn Asp Ser Thr Val
            180                 185                 190
Phe Asp Lys Leu Phe Phe Ser Gln Leu Ser Arg Leu Gly Pro Arg Ala
        195                 200                 205
Lys Leu Arg Gln Thr Ala Asp Ile Cys Ala Leu Pro Ala Lys Ala His
    210                 215                 220
Ile Tyr Arg Glu Gly Cys Ala Gln Ser Leu Gln Lys Trp Leu His Asn
225                 230                 235                 240
Asn Ile Ile Ser Ile Val Gly Ile Cys Leu Gly Val Gly Leu Leu Glu
                245                 250                 255
Leu Gly Phe Met Thr Leu Ser Ile Phe Leu Cys Arg Asn Leu Asp His
            260                 265                 270
Val Tyr Asp Arg Leu Ala Arg Tyr Arg
        275                 280
```

<210> SEQ ID NO 4
<211> LENGTH: 5
<212> TYPE: PRT
<213> ORGANISM: artificial sequence
<220> FEATURE:
<223> OTHER INFORMATION: VH-CDR1

<400> SEQUENCE: 4

```
Thr Ser Gly Val Ser
1               5
```

<210> SEQ ID NO 5
<211> LENGTH: 9
<212> TYPE: PRT
<213> ORGANISM: artificial sequence
<220> FEATURE:
<223> OTHER INFORMATION: VH-CDR2

<400> SEQUENCE: 5

```
Val Ile Trp Gly Asp Gly Ser Thr Asn
1               5
```

<210> SEQ ID NO 6
<211> LENGTH: 7
<212> TYPE: PRT
<213> ORGANISM: artificial sequence
<220> FEATURE:
<223> OTHER INFORMATION: VH-CDR3

<400> SEQUENCE: 6

```
Gly Gly Tyr Ser Leu Ala His
1               5
```

<210> SEQ ID NO 7
<211> LENGTH: 11
<212> TYPE: PRT
<213> ORGANISM: artificial sequence
<220> FEATURE:
<223> OTHER INFORMATION: VL-CDR1

<400> SEQUENCE: 7

```
Arg Ala Ser Glu Asn Ile Arg Ser Asn Leu Ala
1               5                   10

<210> SEQ ID NO 8
<211> LENGTH: 7
<212> TYPE: PRT
<213> ORGANISM: artificial sequence
<220> FEATURE:
<223> OTHER INFORMATION: VL-CDR2

<400> SEQUENCE: 8

Val Ala Thr Asn Leu Ala Asp
1               5

<210> SEQ ID NO 9
<211> LENGTH: 9
<212> TYPE: PRT
<213> ORGANISM: artificial sequence
<220> FEATURE:
<223> OTHER INFORMATION: VL-CDR3

<400> SEQUENCE: 9

Gln His Tyr Trp Gly Thr Thr Trp Thr
1               5

<210> SEQ ID NO 10
<211> LENGTH: 115
<212> TYPE: PRT
<213> ORGANISM: artificial sequence
<220> FEATURE:
<223> OTHER INFORMATION: VH muCD37-3

<400> SEQUENCE: 10

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 11
<211> LENGTH: 115
<212> TYPE: PRT
<213> ORGANISM: artificial sequence
<220> FEATURE:
<223> OTHER INFORMATION: VH chCD37-3

<400> SEQUENCE: 11

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30
```

```
Gly Val Ser Trp Val Arg Gln Pro Gly Lys Gly Leu Glu Trp Leu
            35                  40                  45

Gly Val Ile Trp Gly Asp Gly Ser Thr Asn Tyr His Ser Ala Leu Lys
 50                  55                  60

Ser Arg Leu Ser Ile Lys Lys Asp His Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Gly Tyr Ser Leu Ala His Trp Gly Gln Gly Thr Leu Val Thr
                100                 105                 110

Val Ser Ala
       115

<210> SEQ ID NO 12
<211> LENGTH: 115
<212> TYPE: PRT
<213> ORGANISM: artificial sequence
<220> FEATURE:
<223> OTHER INFORMATION: VH huCD37-3 (version 1.0)

<400> SEQUENCE: 12

Gln Val Gln Val Gln Glu Ser Gly Pro Gly Leu Val Ala Pro Ser Gln
 1               5                  10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Pro Ser Leu Lys
 50                  55                  60

Ser Arg Leu Ser Ile Lys Lys Asp His Ser Lys Ser Gln Val Phe Leu
 65                  70                  75                  80

Lys Leu Asn Ser Leu Thr Ala Ala Asp Thr Ala Thr Tyr Tyr Cys Ala
                 85                  90                  95

Lys Gly Gly Tyr Ser Leu Ala His Trp Gly Gln Gly Thr Leu Val Thr
                100                 105                 110

Val Ser Ser
       115

<210> SEQ ID NO 13
<211> LENGTH: 108
<212> TYPE: PRT
<213> ORGANISM: artificial sequence
<220> FEATURE:
<223> OTHER INFORMATION: VL muCD37-3

<400> SEQUENCE: 13

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
            35                  40                  45

Asn Val Ala Thr Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln His Tyr Trp Gly Thr Thr Trp
                 85                  90                  95
```

```
Thr Phe Gly Gly Gly Thr Lys Leu Glu Ile Lys Arg
            100                 105

<210> SEQ ID NO 14
<211> LENGTH: 108
<212> TYPE: PRT
<213> ORGANISM: artificial sequence
<220> FEATURE:
<223> OTHER INFORMATION: VL chCD37-3

<400> SEQUENCE: 14

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg
            100                 105

<210> SEQ ID NO 15
<211> LENGTH: 108
<212> TYPE: PRT
<213> ORGANISM: artificial sequence
<220> FEATURE:
<223> OTHER INFORMATION: VL huCD37-3

<400> SEQUENCE: 15

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
            100                 105

<210> SEQ ID NO 16
<211> LENGTH: 445
<212> TYPE: PRT
<213> ORGANISM: artificial sequence
<220> FEATURE:
<223> OTHER INFORMATION: Heavy chain muCD37-3

<400> SEQUENCE: 16

Gln Val Gln Val Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Thr Ser
            20                  25                  30

Gly Val Ser Trp Val Arg Gln Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
                100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
        130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
                180                 185                 190

Gln Ser Ile Thr Cys Asn Val Ala His Pro Ala Ser Ser Thr Lys Val
                195                 200                 205

Asp Lys Lys Ile Glu Pro Arg Gly Pro Thr Ile Lys Pro Cys Pro Pro
210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Pro Asp Val Gln
                260                 265                 270

Ile Ser Trp Phe Val Asn Asn Val Glu Val His Thr Ala Gln Thr Gln
                275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
                340                 345                 350

Glu Glu Glu Met Thr Lys Lys Gln Val Thr Leu Thr Cys Met Val Thr
                355                 360                 365

Asp Phe Met Pro Glu Asp Ile Tyr Val Glu Trp Thr Asn Asn Gly Lys
    370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
                420                 425                 430

His His Thr Thr Lys Ser Phe Ser Arg Thr Pro Gly Lys
```

<210> SEQ ID NO 17
<211> LENGTH: 445
<212> TYPE: PRT
<213> ORGANISM: artificial sequence
<220> FEATURE:
<223> OTHER INFORMATION: Heavy chain chCD37-3

<400> SEQUENCE: 17

```
Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 18
<211> LENGTH: 444
<212> TYPE: PRT
<213> ORGANISM: artificial sequence
<220> FEATURE:
<223> OTHER INFORMATION: Heavy chain huCD37-3

<400> SEQUENCE: 18

Gln Val Gln Val Gln Glu Ser Gly Pro Gly Leu Val Ala Pro Ser Gln
1               5                   10                  15
Thr Leu Ser Ile Thr Cys Thr Val Ser Gly Phe Ser Leu Thr Thr Ser
            20                  25                  30
Gly Val Ser Trp Val Arg Gln Pro Pro Gly Lys Gly Leu Glu Trp Leu
        35                  40                  45
Gly Val Ile Trp Gly Asp Gly Ser Thr Asn Tyr His Pro Ser Leu Lys
    50                  55                  60
Ser Arg Leu Ser Ile Lys Lys Asp His Ser Lys Ser Gln Val Phe Leu
65                  70                  75                  80
Lys Leu Asn Ser Leu Thr Ala Ala Asp Thr Ala Thr Tyr Tyr Cys Ala
                85                  90                  95
Lys Gly Gly Tyr Ser Leu Ala His Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
```

```
                    275                 280                 285
Pro Arg Glu Glu Gln Tyr Asn Ser Thr Tyr Arg Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 19
<211> LENGTH: 214
<212> TYPE: PRT
<213> ORGANISM: artificial sequence
<220> FEATURE:
<223> OTHER INFORMATION: light chain muCD37-3

<400> SEQUENCE: 19

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
                20                  25                  30

Leu Ala Trp Tyr Gln Gln Lys Gln Gly Lys Ser Pro Gln Leu Leu Val
            35                  40                  45

Asn Val Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
```

-continued

```
                195                 200                 205

Phe Asn Arg Asn Glu Cys
    210

<210> SEQ ID NO 20
<211> LENGTH: 214
<212> TYPE: PRT
<213> ORGANISM: artificial sequence
<220> FEATURE:
<223> OTHER INFORMATION: light chain chCD37-3

<400> SEQUENCE: 20

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 214
<212> TYPE: PRT
<213> ORGANISM: artificial sequence
<220> FEATURE:
<223> OTHER INFORMATION: light chain huCD37-3

<400> SEQUENCE: 21

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60
```

```
Ser Gly Ser Gly Thr Asp Tyr Ser Leu Lys Ile Asn Ser Leu Gln Pro
 65                  70                  75                  80

Glu Asp Phe Gly Thr Tyr Tyr Cys Gln His Tyr Trp Gly Thr Thr Trp
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 22
<211> LENGTH: 115
<212> TYPE: PRT
<213> ORGANISM: artificial sequence
<220> FEATURE:
<223> OTHER INFORMATION: VH huCD37-3 (version 1.1)

<400> SEQUENCE: 22

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 23
<211> LENGTH: 742
<212> TYPE: PRT
<213> ORGANISM: Homo Sapiens

<400> SEQUENCE: 23

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
```

```
                35                  40                  45
Ala Ala Asp Leu Cys Lys Ala Phe Asn Ser Thr Leu Pro Thr Met Ala
 50                  55                  60

Gln Met Glu Lys Ala Leu Ser Ile Gly Phe Glu Thr Cys Arg Tyr Gly
 65                  70                  75                  80

Phe Ile Glu Gly His Val Val Ile Pro Arg Ile His Pro Asn Ser Ile
                     85                  90                  95

Cys Ala Ala Asn Asn Thr Gly Val Tyr Ile Leu Thr Ser Asn Thr Ser
                    100                 105                 110

Gln Tyr Asp Thr Tyr Cys Phe Asn Ala Ser Ala Pro Glu Glu Asp
                115                 120                 125

Cys Thr Ser Val Thr Asp Leu Pro Asn Ala Phe Asp Gly Pro Ile Thr
                130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                    165                 170                 175

Asp Val Ser Ser Gly Ser Ser Ser Glu Arg Ser Ser Thr Ser Gly Gly
                180                 185                 190

Tyr Ile Phe Tyr Thr Phe Ser Thr Val His Pro Ile Pro Asp Glu Asp
                195                 200                 205

Ser Pro Trp Ile Thr Asp Ser Thr Asp Arg Ile Pro Ala Thr Thr Leu
210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                    245                 250                 255

His Leu His Thr Thr Thr Gln Met Ala Gly Thr Ser Ser Asn Thr Ile
                260                 265                 270

Ser Ala Gly Trp Glu Pro Asn Glu Glu Asn Glu Asp Glu Arg Asp Arg
                275                 280                 285

His Leu Ser Phe Ser Gly Ser Gly Ile Asp Asp Glu Asp Phe Ile
                290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                    325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
                355                 360                 365

His His Glu His His Glu Glu Glu Thr Pro His Ser Thr Ser Thr
                370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                    405                 410                 415

Lys Glu Asp Ser His Ser Thr Thr Gly Thr Ala Ala Ala Ser Ala His
                420                 425                 430

Thr Ser His Pro Met Gln Gly Arg Thr Thr Pro Ser Pro Glu Asp Ser
                435                 440                 445

Ser Trp Thr Asp Phe Phe Asn Pro Ile Ser His Pro Met Gly Arg Gly
                450                 455                 460
```

-continued

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
            485                 490                 495

Arg Thr Gly Pro Leu Ser Met Thr Thr Gln Gln Ser Asn Ser Gln Ser
        500                 505                 510

Phe Ser Thr Ser His Glu Gly Leu Glu Glu Asp Lys Asp His Pro Thr
    515                 520                 525

Thr Ser Thr Leu Thr Ser Ser Asn Arg Asn Asp Val Thr Gly Gly Arg
530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
            565                 570                 575

Thr Ser Ala Lys Thr Gly Ser Phe Gly Val Thr Ala Val Thr Val Gly
        580                 585                 590

Asp Ser Asn Ser Asn Val Asn Arg Ser Leu Ser Gly Asp Gln Asp Thr
    595                 600                 605

Phe His Pro Ser Gly Gly Ser His Thr Thr His Gly Ser Glu Ser Asp
610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
            645                 650                 655

Leu Leu Ala Leu Ala Leu Ile Leu Ala Val Cys Ile Ala Val Asn Ser
        660                 665                 670

Arg Arg Arg Cys Gly Gln Lys Lys Lys Leu Val Ile Asn Ser Gly Asn
    675                 680                 685

Gly Ala Val Glu Asp Arg Lys Pro Ser Gly Leu Asn Gly Glu Ala Ser
690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
            725                 730                 735

Asp Met Lys Ile Gly Val
            740

<210> SEQ ID NO 24
<211> LENGTH: 466
<212> TYPE: PRT
<213> ORGANISM: Homo Sapiens

<400> SEQUENCE: 24

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe

```
                85                  90                  95
Lys Asn Thr Arg Thr Asn Glu Lys Val Glu Leu Gln Glu Leu Asn Asp
            100                 105                 110
Arg Phe Ala Asn Tyr Ile Asp Lys Val Arg Phe Leu Glu Gln Gln Asn
            115                 120                 125
Lys Ile Leu Leu Ala Glu Leu Glu Gln Leu Lys Gly Gln Gly Lys Ser
            130                 135                 140
Arg Leu Gly Asp Leu Tyr Glu Glu Glu Met Arg Glu Leu Arg Arg Gln
145                 150                 155                 160
Val Asp Gln Leu Thr Asn Asp Lys Ala Arg Val Glu Val Glu Arg Asp
                165                 170                 175
Asn Leu Ala Glu Asp Ile Met Arg Leu Arg Glu Lys Leu Gln Glu Glu
            180                 185                 190
Met Leu Gln Arg Glu Glu Ala Glu Asn Thr Leu Gln Ser Phe Arg Gln
            195                 200                 205
Asp Val Asp Asn Ala Ser Leu Ala Arg Leu Asp Leu Glu Arg Lys Val
            210                 215                 220
Glu Ser Leu Gln Glu Glu Ile Ala Phe Leu Lys Lys Leu His Glu Glu
225                 230                 235                 240
Glu Ile Gln Glu Leu Gln Ala Gln Ile Gln Glu Gln His Val Gln Ile
                245                 250                 255
Asp Val Asp Val Ser Lys Pro Asp Leu Thr Ala Ala Leu Arg Asp Val
            260                 265                 270
Arg Gln Gln Tyr Glu Ser Val Ala Ala Lys Asn Leu Gln Glu Ala Glu
            275                 280                 285
Glu Trp Tyr Lys Ser Lys Phe Ala Asp Leu Ser Glu Ala Ala Asn Arg
            290                 295                 300
Asn Asn Asp Ala Leu Arg Gln Ala Lys Gln Glu Ser Thr Glu Tyr Arg
305                 310                 315                 320
Arg Gln Val Gln Ser Leu Thr Cys Glu Val Asp Ala Leu Lys Gly Thr
                325                 330                 335
Asn Glu Ser Leu Glu Arg Gln Met Arg Glu Met Glu Glu Asn Phe Ala
            340                 345                 350
Val Glu Ala Ala Asn Tyr Gln Asp Thr Ile Gly Arg Leu Gln Asp Glu
            355                 360                 365
Ile Gln Asn Met Lys Glu Glu Met Ala Arg His Leu Arg Glu Tyr Gln
            370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ser Leu Pro Leu Pro
                405                 410                 415
Asn Phe Ser Ser Leu Asn Leu Arg Glu Thr Asn Leu Asp Ser Leu Pro
            420                 425                 430
Leu Val Asp Thr His Ser Lys Arg Thr Leu Leu Ile Lys Thr Val Glu
            435                 440                 445
Thr Arg Asp Gly Gln Val Ile Asn Glu Thr Ser Gln His His Asp Asp
            450                 455                 460
Leu Glu
465

<210> SEQ ID NO 25
<211> LENGTH: 339
<212> TYPE: PRT
<213> ORGANISM: Homo Sapiens
```

<400> SEQUENCE: 25

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 26
<211> LENGTH: 239
<212> TYPE: PRT
<213> ORGANISM: Homo Sapiens

<400> SEQUENCE: 26

Met Ala His Ala Gly Arg Thr Gly Tyr Asp Asn Arg Glu Ile Val Met
1               5                   10                  15

```
Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 27
<211> LENGTH: 339
<212> TYPE: PRT
<213> ORGANISM: Homo Sapiens

<400> SEQUENCE: 27

Met Ser Thr Val His Glu Ile Leu Cys Lys Leu Ser Leu Glu Gly Asp
 1               5                  10                  15

His Ser Thr Pro Pro Ser Ala Tyr Gly Ser Val Lys Ala Tyr Thr Asn
                20                  25                  30

Phe Asp Ala Glu Arg Asp Ala Leu Asn Ile Glu Thr Ala Ile Lys Thr
            35                  40                  45

Lys Gly Val Asp Glu Val Thr Ile Val Asn Ile Val Thr Asn Arg Asp
 50                  55                  60

Asn Ala Gln Arg Gln Asp Ile Val Phe Ser Tyr Gln Arg Arg Thr Lys
 65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160
```

```
Ser Asp Thr Ser Gly Asp Phe Arg Lys Leu Met Val Ala Leu Ala Lys
            165                 170                 175

Gly Arg Arg Ala Glu Asp Gly Ser Val Ile Asp Tyr Glu Leu Ile Asp
            180                 185                 190

Gln Asp Ala Gln Asp Leu Tyr Asp Ala Gly Val Lys Arg Lys Gly Thr
            195                 200                 205

Asp Val Pro Lys Trp Ile Ser Ile Met Thr Glu Arg Ser Val Pro His
            210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
            245                 250                 255

Leu Asn Leu Val Gln Arg Ile Gln Asn Lys Pro Leu Tyr Phe Ala Asp
            260                 265                 270

Gln Leu Tyr Asp Ser Met Lys Gly Lys Gly Thr Arg Asp Lys Val Leu
            275                 280                 285

Ile Arg Ile Met Val Ser Arg Ser Glu Val Asp Met Leu Lys Ile Arg
            290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
            325                 330                 335

Gly Asp Asp

<210> SEQ ID NO 28
<211> LENGTH: 724
<212> TYPE: PRT
<213> ORGANISM: Homo Sapiens

<400> SEQUENCE: 28

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
            35                  40                  45

Asp Ala Leu Asp Lys Ile Arg Tyr Glu Ser Leu Thr Asp Pro Ser Lys
        50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
            85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
            115                 120                 125

Phe Gly Val Gly Phe Tyr Ser Ala Tyr Leu Val Ala Glu Lys Val Val
            130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
            165                 170                 175

Arg Gly Thr Lys Val Ile Leu His Leu Lys Glu Asp Gln Thr Glu Tyr
            180                 185                 190
```

```
Leu Glu Glu Arg Arg Val Lys Glu Val Val Lys Lys His Ser Gln Phe
            195                 200                 205
Ile Gly Tyr Pro Ile Thr Leu Tyr Leu Glu Lys Glu Arg Glu Lys Glu
    210                 215                 220
Ile Ser Asp Asp Glu Ala Glu Glu Lys Gly Glu Lys Glu Glu
225                 230                 235                 240
Asp Lys Asp Asp Glu Glu Lys Pro Lys Ile Glu Asp Val Gly Ser Asp
                245                 250                 255
Glu Glu Asp Asp Ser Gly Lys Asp Lys Lys Lys Thr Lys Lys Ile
                260                 265                 270
Lys Glu Lys Tyr Ile Asp Gln Glu Leu Asn Lys Thr Lys Pro Ile
            275                 280                 285
Trp Thr Arg Asn Pro Asp Asp Ile Thr Gln Glu Glu Tyr Gly Glu Phe
            290                 295                 300
Tyr Lys Ser Leu Thr Asn Asp Trp Glu Asp His Leu Ala Val Lys His
305                 310                 315                 320
Phe Ser Val Glu Gly Gln Leu Glu Phe Arg Ala Leu Leu Phe Ile Pro
                325                 330                 335
Arg Arg Ala Pro Phe Asp Leu Phe Glu Asn Lys Lys Lys Lys Asn Asn
                340                 345                 350
Ile Lys Leu Tyr Val Arg Arg Val Phe Ile Met Asp Ser Cys Asp Glu
            355                 360                 365
Leu Ile Pro Glu Tyr Leu Asn Phe Ile Arg Gly Val Val Asp Ser Glu
            370                 375                 380
Asp Leu Pro Leu Asn Ile Ser Arg Glu Met Leu Gln Gln Ser Lys Ile
385                 390                 395                 400
Leu Lys Val Ile Arg Lys Asn Ile Val Lys Lys Cys Leu Glu Leu Phe
                405                 410                 415
Ser Glu Leu Ala Glu Asp Lys Glu Asn Tyr Lys Lys Phe Tyr Glu Ala
                420                 425                 430
Phe Ser Lys Asn Leu Lys Leu Gly Ile His Glu Asp Ser Thr Asn Arg
            435                 440                 445
Arg Arg Leu Ser Glu Leu Leu Arg Tyr His Thr Ser Gln Ser Gly Asp
            450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
                485                 490                 495
Ser Ala Phe Val Glu Arg Val Arg Lys Arg Gly Phe Glu Val Val Tyr
                500                 505                 510
Met Thr Glu Pro Ile Asp Glu Tyr Cys Val Gln Gln Leu Lys Glu Phe
            515                 520                 525
Asp Gly Lys Ser Leu Val Ser Val Thr Lys Glu Gly Leu Glu Leu Pro
            530                 535                 540
Glu Asp Glu Glu Glu Lys Lys Met Glu Glu Ser Lys Ala Lys Phe
545                 550                 555                 560
Glu Asn Leu Cys Lys Leu Met Lys Glu Ile Leu Asp Lys Lys Val Glu
                565                 570                 575
Lys Val Thr Ile Ser Asn Arg Leu Val Ser Ser Pro Cys Cys Ile Val
            580                 585                 590
Thr Ser Thr Tyr Gly Trp Thr Ala Asn Met Glu Arg Ile Met Lys Ala
            595                 600                 605
```

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
                675                 680                 685

Gly Ile Asp Glu Asp Glu Val Ala Ala Glu Pro Asn Ala Ala Val
        690                 695                 700

Pro Asp Glu Ile Pro Pro Leu Glu Gly Asp Glu Asp Ala Ser Arg Met
705                 710                 715                 720

Glu Glu Val Asp

<210> SEQ ID NO 29
<211> LENGTH: 718
<212> TYPE: PRT
<213> ORGANISM: Homo Sapiens

<400> SEQUENCE: 29

Met Ile Val Asp Lys Leu Leu Asp Asp Ser Arg Gly Gly Glu Gly Leu
1               5                   10                  15

Arg Asp Ala Ala Gly Gly Cys Gly Leu Met Thr Ser Pro Leu Asn Leu
                20                  25                  30

Ser Tyr Phe Tyr Gly Ala Ser Pro Ala Ala Ala Pro Gly Ala Cys
            35                  40                  45

Asp Ala Ser Cys Ser Val Leu Gly Pro Ser Ala Pro Gly Ser Pro Gly
50                  55                  60

Ser Asp Ser Ser Asp Phe Ser Ser Ala Ser Ser Val Ser Ser Cys Gly
65                  70                  75                  80

Ala Val Glu Ser Arg Ser Arg Gly Gly Ala Arg Ala Glu Arg Gln Pro
                85                  90                  95

Val Glu Pro His Met Gly Val Gly Arg Gln Gln Arg Gly Pro Phe Gln
                100                 105                 110

Gly Val Arg Val Lys Asn Ser Val Lys Glu Leu Leu Leu His Ile Arg
            115                 120                 125

Ser His Lys Gln Lys Ala Ser Gly Gln Ala Val Asp Asp Phe Lys Thr
130                 135                 140

Gln Gly Val Asn Ile Glu Gln Phe Arg Glu Leu Lys Asn Thr Val Ser
145                 150                 155                 160

Tyr Ser Gly Lys Arg Lys Gly Pro Asp Ser Leu Ser Asp Gly Pro Ala
                165                 170                 175

Cys Lys Arg Pro Ala Leu Leu His Ser Gln Phe Leu Thr Pro Pro Gln
            180                 185                 190

Thr Pro Thr Pro Gly Glu Ser Met Glu Asp Val His Leu Asn Glu Pro
        195                 200                 205

Lys Gln Glu Ser Ser Ala Asp Leu Leu Gln Asn Ile Ile Asn Ile Lys
    210                 215                 220

Asn Glu Cys Ser Pro Val Ser Leu Asn Thr Val Gln Val Ser Trp Leu
225                 230                 235                 240

Asn Pro Val Val Val Pro Gln Ser Ser Pro Ala Glu Gln Cys Gln Asp
                245                 250                 255

-continued

Phe His Gly Gly Gln Val Phe Ser Pro Pro Gln Lys Cys Gln Pro Phe
              260                 265                 270

Gln Val Arg Gly Ser Gln Gln Met Ile Asp Gln Ala Ser Leu Tyr Gln
          275                 280                 285

Tyr Ser Pro Gln Asn Gln His Val Glu Gln Gln Pro His Tyr Thr His
    290                 295                 300

Lys Pro Thr Leu Glu Tyr Ser Pro Phe Pro Ile Pro Pro Gln Ser Pro
305                 310                 315                 320

Ala Tyr Glu Pro Asn Leu Phe Asp Gly Pro Glu Ser Gln Phe Cys Pro
                325                 330                 335

Asn Gln Ser Leu Val Ser Leu Leu Gly Asp Gln Arg Glu Ser Glu Asn
            340                 345                 350

Ile Ala Asn Pro Met Gln Thr Ser Ser Ser Val Gln Gln Asn Asp
            355                 360                 365

Ala His Leu His Ser Phe Ser Met Met Pro Ser Ser Ala Cys Glu Ala
    370                 375                 380

Met Val Gly His Glu Met Ala Ser Asp Ser Ser Asn Thr Ser Leu Pro
385                 390                 395                 400

Phe Ser Asn Met Gly Asn Pro Met Asn Thr Thr Gln Leu Gly Lys Ser
                405                 410                 415

Leu Phe Gln Trp Gln Val Glu Gln Glu Ser Lys Leu Ala Asn Ile
            420                 425                 430

Ser Gln Asp Gln Phe Leu Ser Lys Asp Ala Asp Gly Asp Thr Phe Leu
            435                 440                 445

His Ile Ala Val Ala Gln Gly Arg Arg Ala Leu Ser Tyr Val Leu Ala
    450                 455                 460

Arg Lys Met Asn Ala Leu His Met Leu Asp Ile Lys Glu His Asn Gly
465                 470                 475                 480

Gln Ser Ala Phe Gln Val Ala Val Ala Ala Asn Gln His Leu Ile Val
                485                 490                 495

Gln Asp Leu Val Asn Ile Gly Ala Gln Val Asn Thr Thr Asp Cys Trp
            500                 505                 510

Gly Arg Thr Pro Leu His Val Cys Ala Glu Lys Gly His Ser Gln Val
    515                 520                 525

Leu Gln Ala Ile Gln Lys Gly Ala Val Gly Ser Asn Gln Phe Val Asp
530                 535                 540

Leu Glu Ala Thr Asn Tyr Asp Gly Leu Thr Pro Leu His Cys Ala Val
545                 550                 555                 560

Ile Ala His Asn Ala Val Val His Glu Leu Gln Arg Asn Gln Gln Pro
                565                 570                 575

His Ser Pro Glu Val Gln Glu Leu Leu Leu Lys Asn Lys Ser Leu Val
            580                 585                 590

Asp Thr Ile Lys Cys Leu Ile Gln Met Gly Ala Ala Val Glu Ala Lys
            595                 600                 605

Asp Arg Lys Ser Gly Arg Thr Ala Leu His Leu Ala Ala Glu Glu Ala
    610                 615                 620

Asn Leu Glu Leu Ile Arg Leu Phe Leu Glu Leu Pro Ser Cys Leu Ser
625                 630                 635                 640

Phe Val Asn Ala Lys Ala Tyr Asn Gly Asn Thr Ala Leu His Val Ala
                645                 650                 655

Ala Ser Leu Gln Tyr Arg Leu Thr Gln Leu Asp Ala Val Arg Leu Leu
            660                 665                 670

Met Arg Lys Gly Ala Asp Pro Ser Thr Arg Asn Leu Glu Asn Glu Gln

```
                675                 680                 685
Pro Val His Leu Val Pro Asp Gly Pro Val Gly Glu Gln Ile Arg Arg
            690                 695                 700

Ile Leu Lys Gly Lys Ser Ile Gln Gln Arg Ala Pro Pro Tyr
705                 710                 715
```

<210> SEQ ID NO 30
<211> LENGTH: 326
<212> TYPE: PRT
<213> ORGANISM: Homo Sapiens

<400> SEQUENCE: 30

```
Met Glu Lys Asp Gly Leu Cys Arg Ala Asp Gln Gln Tyr Glu Cys Val
1               5                   10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
        35                  40                  45

Thr Gly Glu Glu Gly Met Pro Leu Ser Thr Ile Arg Glu Val Ala Val
    50                  55                  60

Leu Arg His Leu Glu Thr Phe Glu His Pro Asn Val Val Arg Leu Phe
65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
290                 295                 300

Arg Cys Lys Glu Asn Leu Asp Ser His Leu Pro Pro Ser Gln Asn Thr
305                 310                 315                 320

Ser Glu Leu Asn Thr Ala
                325
```

<210> SEQ ID NO 31
<211> LENGTH: 142
<212> TYPE: PRT
<213> ORGANISM: Homo Sapiens

<400> SEQUENCE: 31

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Lys Lys His Ser Ser Gly Cys
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140
```

<210> SEQ ID NO 32
<211> LENGTH: 641
<212> TYPE: PRT
<213> ORGANISM: Homo Sapiens

<400> SEQUENCE: 32

```
Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190
```

```
Arg Asn Val Leu Ile Phe Asp Leu Gly Gly Thr Phe Asp Val Ser
        195                 200                 205

Ile Leu Thr Ile Asp Asp Gly Ile Phe Glu Val Lys Ala Thr Ala Gly
        210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
        340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
                435                 440                 445

Met Thr Lys Asp Asn Asn Leu Leu Gly Arg Phe Glu Leu Ser Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Glu Lys Tyr Lys Ala Glu
                515                 520                 525

Asp Glu Val Gln Arg Glu Arg Val Ser Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
        580                 585                 590

Glu His Lys Arg Lys Glu Leu Glu Gln Val Cys Asn Pro Ile Ile Ser
    595                 600                 605

Gly Leu Tyr Gln Gly Ala Gly Gly Pro Gly Pro Gly Gly Phe Gly Ala
```

-continued

```
                610                 615                 620
Gln Gly Pro Lys Gly Gly Ser Gly Ser Gly Pro Thr Ile Glu Glu Val
625                 630                 635                 640

Asp

<210> SEQ ID NO 33
<211> LENGTH: 732
<212> TYPE: PRT
<213> ORGANISM: Homo Sapiens

<400> SEQUENCE: 33

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Ser Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
            115                 120                 125

Ser Met Ile Gly Gln Phe Gly Val Gly Phe Tyr Ser Ala Tyr Leu Val
        130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
            260                 265                 270

Asp Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
```

```
                340             345             350
Glu Asn Arg Lys Lys Asn Asn Ile Lys Leu Tyr Val Arg Arg Val
            355                 360                 365
Phe Ile Met Asp Asn Cys Glu Glu Leu Ile Pro Glu Tyr Leu Asn Phe
    370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
            420                 425                 430
Asn Tyr Lys Lys Phe Tyr Glu Gln Phe Ser Lys Asn Ile Lys Leu Gly
            435                 440                 445
Ile His Glu Asp Ser Gln Asn Arg Lys Lys Leu Ser Glu Leu Leu Arg
        450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                485                 490                 495
Glu Thr Lys Asp Gln Val Ala Asn Ser Ala Phe Val Glu Arg Leu Arg
            500                 505                 510
Lys His Gly Leu Glu Val Ile Tyr Met Ile Glu Pro Ile Asp Glu Tyr
            515                 520                 525
Cys Val Gln Gln Leu Lys Glu Phe Glu Gly Lys Thr Leu Val Ser Val
        530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
                565                 570                 575
Asp Ile Leu Glu Lys Lys Val Glu Lys Val Val Val Ser Asn Arg Leu
            580                 585                 590
Val Thr Ser Pro Cys Cys Ile Val Thr Ser Thr Tyr Gly Trp Thr Ala
            595                 600                 605
Asn Met Glu Arg Ile Met Lys Ala Gln Ala Leu Arg Asp Asn Ser Thr
        610                 615                 620
Met Gly Tyr Met Ala Ala Lys Lys His Leu Glu Ile Asn Pro Asp His
625                 630                 635                 640
Ser Ile Ile Glu Thr Leu Arg Gln Lys Ala Glu Ala Asp Lys Asn Asp
                645                 650                 655
Lys Ser Val Lys Asp Leu Val Ile Leu Leu Tyr Glu Thr Ala Leu Leu
            660                 665                 670
Ser Ser Gly Phe Ser Leu Glu Asp Pro Gln Thr His Ala Asn Arg Ile
            675                 680                 685
Tyr Arg Met Ile Lys Leu Gly Leu Gly Ile Asp Glu Asp Asp Pro Thr
        690                 695                 700
Ala Asp Asp Thr Ser Ala Ala Val Thr Glu Glu Met Pro Pro Leu Glu
705                 710                 715                 720
Gly Asp Asp Asp Thr Ser Arg Met Glu Glu Val Asp
                725                 730

<210> SEQ ID NO 34
<211> LENGTH: 442
<212> TYPE: PRT
<213> ORGANISM: Homo Sapiens
```

<400> SEQUENCE: 34

```
Met Ala Ser Val Val Leu Pro Ser Gly Ser Gln Cys Ala Ala Ala
1               5                   10                  15

Ala Ala Ala Ala Pro Pro Gly Leu Arg Leu Arg Leu Leu Leu Leu
            20                  25                  30

Phe Ser Ala Ala Ala Leu Ile Pro Thr Gly Asp Gly Gln Asn Leu Phe
        35                  40                  45

Thr Lys Asp Val Thr Val Ile Glu Gly Glu Val Ala Thr Ile Ser Cys
50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
            195                 200                 205

Val His Lys Glu Asp Asp Gly Val Pro Val Ile Cys Gln Val Glu His
210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
            275                 280                 285

Gln His Ala Val Leu Ser Gly Pro Asn Leu Phe Ile Asn Asn Leu Asn
        290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr Thr
            340                 345                 350

Thr Ile Leu Thr Ile Ile Thr Asp Ser Arg Ala Gly Glu Glu Gly Ser
        355                 360                 365

Ile Arg Ala Val Asp His Ala Val Ile Gly Gly Val Val Ala Val Val
            370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
```

```
                        405                 410                 415
Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
            435                 440

<210> SEQ ID NO 35
<211> LENGTH: 329
<212> TYPE: PRT
<213> ORGANISM: Homo Sapiens

<400> SEQUENCE: 35

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
            115                 120                 125

Glu Leu Ser Val Leu Ala Asn Phe Ser Gln Pro Glu Ile Val Pro Ile
130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
            195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
            275                 280                 285

Arg Glu Glu Ser Glu Gln Thr Lys Lys Arg Glu Lys Ile His Ile Pro
290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

<210> SEQ ID NO 36
<211> LENGTH: 445
<212> TYPE: PRT
<213> ORGANISM: Homo Sapiens

<400> SEQUENCE: 36

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Ser Tyr His Gly Asp Ser Asp Leu Gln Leu Glu Arg Ile Asn
        35                  40                  45

Val Tyr Tyr Asn Glu Ala Ala Gly Asn Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ser Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Met Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Ser Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Met Phe Asp Ser Lys Asn Met Met Ala Ala Cys Asp
    290                 295                 300

Pro Arg His Gly Arg Tyr Leu Thr Val Ala Ala Ile Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
        355                 360                 365

Gly Asn Ser Thr Ala Ile Gln Glu Leu Phe Lys Arg Ile Ser Glu Gln
    370                 375                 380

```
Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Asp Glu
            420                 425                 430

Gln Gly Glu Phe Glu Glu Glu Gly Glu Asp Glu Ala
        435                 440                 445
```

<210> SEQ ID NO 37
<211> LENGTH: 451
<212> TYPE: PRT
<213> ORGANISM: Homo Sapiens

<400> SEQUENCE: 37

```
Met Pro Arg Glu Ile Ile Thr Leu Gln Leu Gly Gln Cys Gly Asn Gln
1               5                   10                  15

Ile Gly Phe Glu Phe Trp Lys Gln Leu Cys Ala Glu His Gly Ile Ser
            20                  25                  30

Pro Glu Gly Ile Val Glu Glu Phe Ala Thr Glu Gly Thr Asp Arg Lys
        35                  40                  45

Asp Val Phe Phe Tyr Gln Ala Asp Asp Glu His Tyr Ile Pro Arg Ala
    50                  55                  60

Val Leu Leu Asp Leu Glu Pro Arg Val Ile His Ser Ile Leu Asn Ser
65                  70                  75                  80

Pro Tyr Ala Lys Leu Tyr Asn Pro Glu Asn Ile Tyr Leu Ser Glu His
                85                  90                  95

Gly Gly Gly Ala Gly Asn Asn Trp Ala Ser Gly Phe Ser Gln Gly Glu
            100                 105                 110

Lys Ile His Glu Asp Ile Phe Asp Ile Ile Asp Arg Glu Ala Asp Gly
        115                 120                 125

Ser Asp Ser Leu Glu Gly Phe Val Leu Cys His Ser Ile Ala Gly Gly
    130                 135                 140

Thr Gly Ser Gly Leu Gly Ser Tyr Leu Leu Glu Arg Leu Asn Asp Arg
145                 150                 155                 160

Tyr Pro Lys Lys Leu Val Gln Thr Tyr Ser Val Phe Pro Asn Gln Asp
                165                 170                 175

Glu Met Ser Asp Val Val Gln Pro Tyr Asn Ser Leu Leu Thr Leu
            180                 185                 190

Lys Arg Leu Thr Gln Asn Ala Asp Cys Val Val Leu Asp Asn Thr
        195                 200                 205

Ala Leu Asn Arg Ile Ala Thr Asp Arg Leu His Ile Gln Asn Pro Ser
    210                 215                 220

Phe Ser Gln Ile Asn Gln Leu Val Ser Thr Ile Met Ser Ala Ser Thr
225                 230                 235                 240

Thr Thr Leu Arg Tyr Pro Gly Tyr Met Asn Asn Asp Leu Ile Gly Leu
                245                 250                 255

Ile Ala Ser Leu Ile Pro Thr Pro Arg Leu His Phe Leu Met Thr Gly
            260                 265                 270

Tyr Thr Pro Leu Thr Thr Asp Gln Ser Val Ala Ser Val Arg Lys Thr
        275                 280                 285

Thr Val Leu Asp Val Met Arg Arg Leu Leu Gln Pro Lys Asn Val Met
    290                 295                 300

Val Ser Thr Gly Arg Asp Arg Gln Thr Asn His Cys Tyr Ile Ala Ile
```

```
            305                 310                 315                 320
Leu Asn Ile Ile Gln Gly Glu Val Asp Pro Thr Gln Val His Lys Ser
                325                 330                 335
Leu Gln Arg Ile Arg Glu Arg Lys Leu Ala Asn Phe Ile Pro Trp Gly
                340                 345                 350
Pro Ala Ser Ile Gln Val Ala Leu Ser Arg Lys Ser Pro Tyr Leu Pro
                355                 360                 365
Ser Ala His Arg Val Ser Gly Leu Met Met Ala Asn His Thr Ser Ile
                370                 375                 380
Ser Ser Leu Phe Glu Arg Thr Cys Arg Gln Tyr Asp Lys Leu Arg Lys
385                 390                 395                 400
Arg Glu Ala Phe Leu Glu Gln Phe Arg Lys Glu Asp Met Phe Lys Asp
                405                 410                 415
Asn Phe Asp Glu Met Asp Thr Ser Arg Glu Ile Val Gln Gln Leu Ile
                420                 425                 430
Asp Glu Tyr His Ala Ala Thr Arg Pro Asp Tyr Ile Ser Trp Gly Thr
                435                 440                 445
Gln Glu Gln
    450

<210> SEQ ID NO 38
<211> LENGTH: 2555
<212> TYPE: PRT
<213> ORGANISM: Homo Sapiens

<400> SEQUENCE: 38

Met Pro Pro Leu Leu Ala Pro Leu Leu Cys Leu Ala Leu Leu Pro Ala
1               5                   10                  15
Leu Ala Ala Arg Gly Pro Arg Cys Ser Gln Pro Gly Glu Thr Cys Leu
                20                  25                  30
Asn Gly Gly Lys Cys Glu Ala Ala Asn Gly Thr Glu Ala Cys Val Cys
                35                  40                  45
Gly Gly Ala Phe Val Gly Pro Arg Cys Gln Asp Pro Asn Pro Cys Leu
    50                  55                  60
Ser Thr Pro Cys Lys Asn Ala Gly Thr Cys His Val Val Asp Arg Arg
65                  70                  75                  80
Gly Val Ala Asp Tyr Ala Cys Ser Cys Ala Leu Gly Phe Ser Gly Pro
                85                  90                  95
Leu Cys Leu Thr Pro Leu Asp Asn Ala Cys Leu Thr Asn Pro Cys Arg
                100                 105                 110
Asn Gly Gly Thr Cys Asp Leu Leu Thr Leu Thr Glu Tyr Lys Cys Arg
                115                 120                 125
Cys Pro Pro Gly Trp Ser Gly Lys Ser Cys Gln Gln Ala Asp Pro Cys
    130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
                180                 185                 190
Gly Thr Cys His Asn Glu Val Gly Ser Tyr Arg Cys Val Cys Arg Ala
                195                 200                 205
Thr His Thr Gly Pro Asn Cys Glu Arg Pro Tyr Val Pro Cys Ser Pro
    210                 215                 220
```

```
Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
            245                 250                 255

Asn Ile Asp Asp Cys Pro Gly Asn Asn Cys Lys Asn Gly Gly Ala Cys
                260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
            405                 410                 415

Ser Leu Gly Ala Asn Pro Cys Glu His Ala Gly Lys Cys Ile Asn Thr
        420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
            485                 490                 495

Ser Pro Cys Leu His Asn Gly Arg Cys Leu Asp Lys Ile Asn Glu Phe
        500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
            565                 570                 575

Tyr Gly Ser Cys Lys Asp Gly Val Ala Thr Phe Thr Cys Leu Cys Arg
        580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
        610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
```

-continued

```
                645                 650                 655
Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
                675                 680                 685

Asn Gly Gly Thr Cys Glu Asp Gly Ile Asn Gly Phe Thr Cys Arg Cys
                690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
                755                 760                 765

Lys Asp Met Thr Ser Gly Tyr Val Cys Thr Cys Arg Glu Gly Phe Ser
                770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
                835                 840                 845

Asp Tyr Glu Ser Phe Ser Cys Val Cys Pro Thr Gly Trp Gln Gly Gln
                850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
                915                 920                 925

Ala Phe Cys Asp Cys Leu Pro Gly Phe Arg Gly Thr Phe Cys Glu Glu
                930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
                980                 985                 990

Phe Asn Gly Gly Thr Cys Val Asp Gly Ile Asn Ser Phe Thr Cys Leu
                995                 1000                1005

Cys Pro Pro Gly Phe Thr Gly Ser Tyr Cys Gln His Asp Val Asn
            1010                1015                1020

Glu Cys Asp Ser Gln Pro Cys Leu His Gly Gly Thr Cys Gln Asp
            1025                1030                1035

Gly Cys Gly Ser Tyr Arg Cys Thr Cys Pro Gln Gly Tyr Thr Gly
            1040                1045                1050

Pro Asn Cys Gln Asn Leu Val His Trp Cys Asp Ser Ser Pro Cys
            1055                1060                1065
```

```
Lys Asn Gly Gly Lys Cys Trp Gln Thr His Thr Gln Tyr Arg Cys
1070            1075                1080

Glu Cys Pro Ser Gly Trp Thr Gly Leu Tyr Cys Asp Val Pro Ser
1085            1090                1095

Val Ser Cys Glu Val Ala Ala Gln Arg Gln Gly Val Asp Val Ala
1100            1105                1110

Arg Leu Cys Gln His Gly Gly Leu Cys Val Asp Ala Gly Asn Thr
1115            1120                1125

His His Cys Arg Cys Gln Ala Gly Tyr Thr Gly Ser Tyr Cys Glu
1130            1135                1140

Asp Leu Val Asp Glu Cys Ser Pro Ser Pro Cys Gln Asn Gly Ala
1145            1150                1155

Thr Cys Thr Asp Tyr Leu Gly Gly Tyr Ser Cys Lys Cys Val Ala
1160            1165                1170

Gly Tyr His Gly Val Asn Cys Ser Glu Glu Ile Asp Glu Cys Leu
1175            1180                1185

Ser His Pro Cys Gln Asn Gly Gly Thr Cys Leu Asp Leu Pro Asn
1190            1195                1200

Thr Tyr Lys Cys Ser Cys Pro Arg Gly Thr Gln Gly Val His Cys
1205            1210                1215

Glu Ile Asn Val Asp Asp Cys Asn Pro Pro Val Asp Pro Val Ser
1220            1225                1230

Arg Ser Pro Lys Cys Phe Asn Asn Gly Thr Cys Val Asp Gln Val
1235            1240                1245

Gly Gly Tyr Ser Cys Thr Cys Pro Pro Gly Phe Val Gly Glu Arg
1250            1255                1260

Cys Glu Gly Asp Val Asn Glu Cys Leu Ser Asn Pro Cys Asp Ala
1265            1270                1275

Arg Gly Thr Gln Asn Cys Val Gln Arg Val Asn Asp Phe His Cys
1280            1285                1290

Glu Cys Arg Ala Gly His Thr Gly Arg Arg Cys Glu Ser Val Ile
1295            1300                1305

Asn Gly Cys Lys Gly Lys Pro Cys Lys Asn Gly Gly Thr Cys Ala
1310            1315                1320

Val Ala Ser Asn Thr Ala Arg Gly Phe Ile Cys Lys Cys Pro Ala
1325            1330                1335

Gly Phe Glu Gly Ala Thr Cys Glu Asn Asp Ala Arg Thr Cys Gly
1340            1345                1350

Ser Leu Arg Cys Leu Asn Gly Gly Thr Cys Ile Ser Gly Pro Arg
1355            1360                1365

Ser Pro Thr Cys Leu Cys Leu Gly Pro Phe Thr Gly Pro Glu Cys
1370            1375                1380

Gln Phe Pro Ala Ser Ser Pro Cys Leu Gly Gly Asn Pro Cys Tyr
1385            1390                1395

Asn Gln Gly Thr Cys Glu Pro Thr Ser Glu Ser Pro Phe Tyr Arg
1400            1405                1410

Cys Leu Cys Pro Ala Lys Phe Asn Gly Leu Leu Cys His Ile Leu
1415            1420                1425

Asp Tyr Ser Phe Gly Gly Gly Ala Gly Arg Asp Ile Pro Pro Pro
1430            1435                1440

Leu Ile Glu Glu Ala Cys Glu Leu Pro Glu Cys Gln Glu Asp Ala
1445            1450                1455
```

```
Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830

Leu Asp Asp Gln Thr Asp His Arg Gln Trp Thr Gln Gln His Leu
    1835                1840                1845

Asp Ala Ala Asp Leu Arg Met Ser Ala Met Ala Pro Thr Pro Pro
```

-continued

```
            1850                1855                1860
Gln Gly Glu Val Asp Ala Asp Cys Met Asp Val Asn Val Arg Gly
            1865                1870                1875
Pro Asp Gly Phe Thr Pro Leu Met Ile Ala Ser Cys Ser Gly Gly
            1880                1885                1890
Gly Leu Glu Thr Gly Asn Ser Glu Glu Glu Glu Asp Ala Pro Ala
            1895                1900                1905
Val Ile Ser Asp Phe Ile Tyr Gln Gly Ala Ser Leu His Asn Gln
            1910                1915                1920
Thr Asp Arg Thr Gly Glu Thr Ala Leu His Leu Ala Ala Arg Tyr
            1925                1930                1935
Ser Arg Ser Asp Ala Ala Lys Arg Leu Leu Glu Ala Ser Ala Asp
            1940                1945                1950
Ala Asn Ile Gln Asp Asn Met Gly Arg Thr Pro Leu His Ala Ala
            1955                1960                1965
Val Ser Ala Asp Ala Gln Gly Val Phe Gln Ile Leu Ile Arg Asn
            1970                1975                1980
Arg Ala Thr Asp Leu Asp Ala Arg Met His Asp Gly Thr Thr Pro
            1985                1990                1995
Leu Ile Leu Ala Ala Arg Leu Ala Val Glu Gly Met Leu Glu Asp
            2000                2005                2010
Leu Ile Asn Ser His Ala Asp Val Asn Ala Val Asp Asp Leu Gly
            2015                2020                2025
Lys Ser Ala Leu His Trp Ala Ala Ala Val Asn Asn Val Asp Ala
            2030                2035                2040
Ala Val Val Leu Leu Lys Asn Gly Ala Asn Lys Asp Met Gln Asn
            2045                2050                2055
Asn Arg Glu Glu Thr Pro Leu Phe Leu Ala Ala Arg Glu Gly Ser
            2060                2065                2070
Tyr Glu Thr Ala Lys Val Leu Leu Asp His Phe Ala Asn Arg Asp
            2075                2080                2085
Ile Thr Asp His Met Asp Arg Leu Pro Arg Asp Ile Ala Gln Glu
            2090                2095                2100
Arg Met His His Asp Ile Val Arg Leu Leu Asp Glu Tyr Asn Leu
            2105                2110                2115
Val Arg Ser Pro Gln Leu His Gly Ala Pro Leu Gly Gly Thr Pro
            2120                2125                2130
Thr Leu Ser Pro Pro Leu Cys Ser Pro Asn Gly Tyr Leu Gly Ser
            2135                2140                2145
Leu Lys Pro Gly Val Gln Gly Lys Lys Val Arg Lys Pro Ser Ser
            2150                2155                2160
Lys Gly Leu Ala Cys Gly Ser Lys Glu Ala Lys Asp Leu Lys Ala
            2165                2170                2175
Arg Arg Lys Lys Ser Gln Asp Gly Lys Gly Cys Leu Leu Asp Ser
            2180                2185                2190
Ser Gly Met Leu Ser Pro Val Asp Ser Leu Glu Ser Pro His Gly
            2195                2200                2205
Tyr Leu Ser Asp Val Ala Ser Pro Pro Leu Leu Pro Ser Pro Phe
            2210                2215                2220
Gln Gln Ser Pro Ser Val Pro Leu Asn His Leu Pro Gly Met Pro
            2225                2230                2235
Asp Thr His Leu Gly Ile Gly His Leu Asn Val Ala Ala Lys Pro
            2240                2245                2250
```

```
Glu Met Ala Ala Leu Gly Gly Gly Arg Leu Ala Phe Glu Thr
    2255            2260                2265

Gly Pro Pro Arg Leu Ser His Leu Pro Val Ala Ser Gly Thr Ser
    2270                2275                2280

Thr Val Leu Gly Ser Ser Gly Gly Ala Leu Asn Phe Thr Val
2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 39
<211> LENGTH: 189
<212> TYPE: PRT
<213> ORGANISM: Homo Sapiens

<400> SEQUENCE: 39

Met Leu Gly Met Ile Lys Asn Ser Leu Phe Gly Ser Val Glu Thr Trp
1               5                   10                  15

Pro Trp Gln Val Leu Ser Lys Gly Asp Lys Glu Glu Val Ala Tyr Glu
            20                  25                  30

Glu Arg Ala Cys Glu Gly Gly Lys Phe Ala Thr Val Glu Val Thr Asp
```

```
                35                  40                  45
Lys Pro Val Asp Glu Ala Leu Arg Glu Ala Met Pro Lys Val Ala Lys
 50                  55                  60

Tyr Ala Gly Gly Thr Asn Asp Lys Gly Ile Gly Met Gly Met Thr Val
 65                  70                  75                  80

Pro Ile Ser Phe Ala Val Phe Pro Asn Glu Asp Gly Ser Leu Gln Lys
                 85                  90                  95

Lys Leu Lys Val Trp Phe Arg Ile Pro Asn Gln Phe Gln Ser Asp Pro
                100                 105                 110

Pro Ala Pro Ser Asp Lys Ser Val Lys Ile Glu Glu Arg Glu Gly Ile
                115                 120                 125

Thr Val Tyr Ser Met Gln Phe Gly Gly Tyr Ala Lys Glu Ala Asp Tyr
                130                 135                 140

Val Ala Gln Ala Thr Arg Leu Arg Ala Ala Leu Glu Gly Thr Ala Thr
145                 150                 155                 160

Tyr Arg Gly Asp Ile Tyr Phe Cys Thr Gly Tyr Asp Pro Pro Met Lys
                165                 170                 175

Pro Tyr Gly Arg Arg Asn Glu Ile Trp Leu Leu Lys Thr
                180                 185

<210> SEQ ID NO 40
<211> LENGTH: 272
<212> TYPE: PRT
<213> ORGANISM: Homo Sapiens

<400> SEQUENCE: 40

Met Ala Ala Lys Val Phe Glu Ser Ile Gly Lys Phe Gly Leu Ala Leu
 1               5                  10                  15

Ala Val Ala Gly Gly Val Val Asn Ser Ala Leu Tyr Asn Val Asp Ala
                 20                  25                  30

Gly His Arg Ala Val Ile Phe Asp Arg Phe Arg Gly Val Gln Asp Ile
                 35                  40                  45

Val Val Gly Glu Gly Thr His Phe Leu Ile Pro Trp Val Gln Lys Pro
 50                  55                  60

Ile Ile Phe Asp Cys Arg Ser Arg Pro Arg Asn Val Pro Val Ile Thr
 65                  70                  75                  80

Gly Ser Lys Asp Leu Gln Asn Val Asn Ile Thr Leu Arg Ile Leu Phe
                 85                  90                  95

Arg Pro Val Ala Ser Gln Leu Pro Arg Ile Phe Thr Ser Ile Gly Glu
                100                 105                 110

Asp Tyr Asp Glu Arg Val Leu Pro Ser Ile Thr Thr Glu Ile Leu Lys
                115                 120                 125

Ser Val Val Ala Arg Phe Asp Ala Gly Glu Leu Ile Thr Gln Arg Glu
                130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
                180                 185                 190

Ala Glu Arg Ala Arg Phe Val Val Glu Lys Ala Glu Gln Gln Lys Lys
                195                 200                 205

Ala Ala Ile Ile Ser Ala Glu Gly Asp Ser Lys Ala Ala Glu Leu Ile
                210                 215                 220
```

```
Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
            245                 250                 255

Ile Thr Tyr Leu Pro Ala Gly Gln Ser Val Leu Leu Gln Leu Pro Gln
        260                 265                 270

<210> SEQ ID NO 41
<211> LENGTH: 254
<212> TYPE: PRT
<213> ORGANISM: Homo Sapiens

<400> SEQUENCE: 41

Met Ala Ser Leu Leu Lys Val Asp Gln Glu Val Lys Leu Lys Val Asp
1               5                   10                  15

Ser Phe Arg Glu Arg Ile Thr Ser Glu Ala Glu Asp Leu Val Ala Asn
            20                  25                  30

Phe Phe Pro Lys Lys Leu Leu Glu Leu Asp Ser Phe Leu Lys Glu Pro
        35                  40                  45

Ile Leu Asn Ile His Asp Leu Thr Gln Ile His Ser Asp Met Asn Leu
    50                  55                  60

Pro Val Pro Asp Pro Ile Leu Leu Thr Asn Ser His Asp Gly Leu Asp
65                  70                  75                  80

Gly Pro Thr Tyr Lys Lys Arg Arg Leu Asp Glu Cys Glu Glu Ala Phe
                85                  90                  95

Gln Gly Thr Lys Val Phe Val Met Pro Asn Gly Met Leu Lys Ser Asn
            100                 105                 110

Gln Gln Leu Val Asp Ile Ile Glu Lys Val Lys Pro Glu Ile Arg Leu
        115                 120                 125

Leu Ile Glu Lys Cys Asn Thr Val Lys Met Trp Val Gln Leu Leu Ile
    130                 135                 140

Pro Arg Ile Glu Asp Gly Asn Asn Phe Gly Val Ser Ile Gln Glu Glu
145                 150                 155                 160

Thr Val Ala Glu Leu Arg Thr Val Glu Ser Glu Ala Ala Ser Tyr Leu
                165                 170                 175

Asp Gln Ile Ser Arg Tyr Tyr Ile Thr Arg Ala Lys Leu Val Ser Lys
            180                 185                 190

Ile Ala Lys Tyr Pro His Val Glu Asp Tyr Arg Arg Thr Val Thr Glu
        195                 200                 205

Ile Asp Glu Lys Glu Tyr Ile Ser Leu Arg Leu Ile Ile Ser Glu Leu
    210                 215                 220

Arg Asn Gln Tyr Val Thr Leu His Asp Met Ile Leu Lys Asn Ile Glu
225                 230                 235                 240

Lys Ile Lys Arg Pro Arg Ser Ser Asn Ala Glu Thr Leu Tyr
                245                 250

<210> SEQ ID NO 42
<211> LENGTH: 107
<212> TYPE: DNA
<213> ORGANISM: Homo Sapiens

<400> SEQUENCE: 42
gtgctcactt cggcagcaca tatactaaaa ttggaacgat acagagaaga ttagcatggc      60
ccctgcgcaa ggatgacacg caaattcgtg aagcattcca tattttt                  107

<210> SEQ ID NO 43
```

<211> LENGTH: 211
<212> TYPE: PRT
<213> ORGANISM: Homo Sapiens

<400> SEQUENCE: 43

Met Ala Pro Ser Arg Asn Gly Met Val Leu Lys Pro His Phe His Lys
1               5                   10                  15

Asp Trp Gln Arg Arg Val Ala Thr Trp Phe Asn Gln Pro Ala Arg Lys
            20                  25                  30

Ile Arg Arg Arg Lys Ala Arg Gln Ala Lys Ala Arg Ile Ala Pro
        35                  40                  45

Arg Pro Ala Ser Gly Pro Ile Arg Pro Ile Val Arg Cys Pro Thr Val
    50                  55                  60

Arg Tyr His Thr Lys Val Arg Ala Gly Arg Gly Phe Ser Leu Glu Glu
65                  70                  75                  80

Leu Arg Val Ala Gly Ile His Lys Lys Val Ala Arg Thr Ile Gly Ile
                85                  90                  95

Ser Val Asp Pro Arg Arg Arg Asn Lys Ser Thr Glu Ser Leu Gln Ala
            100                 105                 110

Asn Val Gln Arg Leu Lys Glu Tyr Arg Ser Lys Leu Ile Leu Phe Pro
        115                 120                 125

Arg Lys Pro Ser Ala Pro Lys Lys Gly Asp Ser Ser Ala Glu Glu Leu
    130                 135                 140

Lys Leu Ala Thr Gln Leu Thr Gly Pro Val Met Pro Val Arg Asn Val
145                 150                 155                 160

Tyr Lys Lys Glu Lys Ala Arg Val Ile Thr Glu Glu Lys Asn Phe
                165                 170                 175

Lys Ala Phe Ala Ser Leu Arg Met Ala Arg Ala Asn Ala Arg Leu Phe
            180                 185                 190

Gly Ile Arg Ala Lys Arg Ala Lys Glu Ala Ala Glu Gln Asp Val Glu
        195                 200                 205

Lys Lys Lys
    210

<210> SEQ ID NO 44
<211> LENGTH: 227
<212> TYPE: PRT
<213> ORGANISM: Homo Sapiens

<400> SEQUENCE: 44

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala
        115                 120                 125

```
Pro Ala Glu Ser Ala Ala Pro Ala Gly Glu Pro Ser Lys Glu
        130                 135                 140

Glu Gly Glu Pro Lys Lys Thr Glu Ala Pro Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
210                 215                 220

Val Lys Glu
225

<210> SEQ ID NO 45
<211> LENGTH: 372
<212> TYPE: PRT
<213> ORGANISM: Homo Sapiens

<400> SEQUENCE: 45

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
```

```
                    260                 265                 270
Ser Pro Tyr His Ile Val Ile Phe Leu Asp Thr Leu Ala Arg Leu Lys
            275                 280                 285

Ala Val Asp Asn Thr Cys Lys Leu Asn Gly Ser Leu Pro Val Ala Ile
            290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
            325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
            355                 360                 365

Leu Thr Thr Phe
        370

<210> SEQ ID NO 46
<211> LENGTH: 160
<212> TYPE: PRT
<213> ORGANISM: Homo Sapiens

<400> SEQUENCE: 46

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
    50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
    130                 135                 140

Ala Leu Leu Leu Pro Leu Leu Ser Gly Gly Leu His Leu Leu Leu Lys
145                 150                 155                 160

<210> SEQ ID NO 47
<211> LENGTH: 162
<212> TYPE: PRT
<213> ORGANISM: Homo Sapiens

<400> SEQUENCE: 47

Met Lys Gly Phe Thr Ala Thr Leu Phe Leu Trp Thr Leu Ile Phe Pro
1               5                   10                  15

Ser Cys Ser Gly Gly Gly Gly Lys Ala Trp Pro Thr His Val Val
            20                  25                  30

Cys Ser Asp Ser Gly Leu Glu Val Leu Tyr Gln Ser Cys Asp Pro Leu
        35                  40                  45

Gln Asp Phe Gly Phe Ser Val Glu Lys Cys Ser Lys Gln Leu Lys Ser
```

```
            50                  55                  60
Asn Ile Asn Ile Arg Phe Gly Ile Ile Leu Arg Glu Asp Ile Lys Glu
 65                  70                  75                  80

Leu Phe Leu Asp Leu Ala Leu Met Ser Gln Gly Ser Ser Val Leu Asn
                 85                  90                  95

Phe Ser Tyr Pro Ile Cys Glu Ala Ala Leu Pro Lys Phe Ser Phe Cys
            100                 105                 110

Gly Arg Arg Lys Gly Glu Gln Ile Tyr Tyr Ala Gly Pro Val Asn Asn
        115                 120                 125

Pro Glu Phe Thr Ile Pro Gln Gly Tyr Gln Val Leu Leu Glu Leu
    130                 135                 140

Tyr Thr Glu Lys Arg Ser Thr Val Ala Cys Ala Asn Ala Thr Ile Met
145                 150                 155                 160

Cys Ser
```

<210> SEQ ID NO 48
<211> LENGTH: 811
<212> TYPE: PRT
<213> ORGANISM: Homo Sapiens

<400> SEQUENCE: 48

```
Met Arg Leu Ile Arg Asn Ile Tyr Ile Phe Cys Ser Ile Val Met Thr
 1               5                  10                  15

Ala Glu Gly Asp Ala Pro Glu Leu Pro Glu Arg Glu Leu Met Thr
                 20                  25                  30

Asn Cys Ser Asn Met Ser Leu Arg Lys Val Pro Ala Asp Leu Thr Pro
             35                  40                  45

Ala Thr Thr Thr Leu Asp Leu Ser Tyr Asn Leu Leu Phe Gln Leu Gln
 50                  55                  60

Ser Ser Asp Phe His Ser Val Ser Lys Leu Arg Val Leu Ile Leu Cys
 65                  70                  75                  80

His Asn Arg Ile Gln Gln Leu Asp Leu Lys Thr Phe Glu Phe Asn Lys
                 85                  90                  95

Glu Leu Arg Tyr Leu Asp Leu Ser Asn Asn Arg Leu Lys Ser Val Thr
            100                 105                 110

Trp Tyr Leu Leu Ala Gly Leu Arg Tyr Leu Asp Leu Ser Phe Asn Asp
        115                 120                 125

Phe Asp Thr Met Pro Ile Cys Glu Glu Ala Gly Asn Met Ser His Leu
    130                 135                 140

Glu Ile Leu Gly Leu Ser Gly Ala Lys Ile Gln Lys Ser Asp Phe Gln
145                 150                 155                 160

Lys Ile Ala His Leu His Leu Asn Thr Val Phe Leu Gly Phe Arg Thr
                165                 170                 175

Leu Pro His Tyr Glu Glu Gly Ser Leu Pro Ile Leu Asn Thr Thr Lys
            180                 185                 190

Leu His Ile Val Leu Pro Met Asp Thr Asn Phe Trp Val Leu Leu Arg
        195                 200                 205

Asp Gly Ile Lys Thr Ser Lys Ile Leu Glu Met Thr Asn Ile Asp Gly
    210                 215                 220

Lys Ser Gln Phe Val Ser Tyr Glu Met Gln Arg Asn Leu Ser Leu Glu
225                 230                 235                 240

Asn Ala Lys Thr Ser Val Leu Leu Leu Asn Lys Val Asp Leu Leu Trp
                245                 250                 255

Asp Asp Leu Phe Leu Ile Leu Gln Phe Val Trp His Thr Ser Val Glu
```

```
            260                 265                 270
His Phe Gln Ile Arg Asn Val Thr Phe Gly Gly Lys Ala Tyr Leu Asp
        275                 280                 285
His Asn Ser Phe Asp Tyr Ser Asn Thr Val Met Arg Thr Ile Lys Leu
    290                 295                 300
Glu His Val His Phe Arg Val Phe Tyr Ile Gln Gln Asp Lys Ile Tyr
305                 310                 315                 320
Leu Leu Leu Thr Lys Met Asp Ile Glu Asn Leu Thr Ile Ser Asn Ala
                325                 330                 335
Gln Met Pro His Met Leu Phe Pro Asn Tyr Pro Thr Lys Phe Gln Tyr
            340                 345                 350
Leu Asn Phe Ala Asn Asn Ile Leu Thr Asp Glu Leu Phe Lys Arg Thr
        355                 360                 365
Ile Gln Leu Pro His Leu Lys Thr Leu Ile Leu Asn Gly Asn Lys Leu
    370                 375                 380
Glu Thr Leu Ser Leu Val Ser Cys Phe Ala Asn Asn Thr Pro Leu Glu
385                 390                 395                 400
His Leu Asp Leu Ser Gln Asn Leu Leu Gln His Lys Asn Asp Glu Asn
                405                 410                 415
Cys Ser Trp Pro Glu Thr Val Val Asn Met Asn Leu Ser Tyr Asn Lys
            420                 425                 430
Leu Ser Asp Ser Val Phe Arg Cys Leu Pro Lys Ser Ile Gln Ile Leu
        435                 440                 445
Asp Leu Asn Asn Asn Gln Ile Gln Thr Val Pro Lys Glu Thr Ile His
    450                 455                 460
Leu Met Ala Leu Arg Glu Leu Asn Ile Ala Phe Asn Phe Leu Thr Asp
465                 470                 475                 480
Leu Pro Gly Cys Ser His Phe Ser Arg Leu Ser Val Leu Asn Ile Glu
                485                 490                 495
Met Asn Phe Ile Leu Ser Pro Ser Leu Asp Phe Val Gln Ser Cys Gln
            500                 505                 510
Glu Val Lys Thr Leu Asn Ala Gly Arg Asn Pro Phe Arg Cys Thr Cys
        515                 520                 525
Glu Leu Lys Asn Phe Ile Gln Leu Glu Thr Tyr Ser Glu Val Met Met
    530                 535                 540
Val Gly Trp Ser Asp Ser Tyr Thr Cys Glu Tyr Pro Leu Asn Leu Arg
545                 550                 555                 560
Gly Thr Arg Leu Lys Asp Val His Leu His Glu Leu Ser Cys Asn Thr
                565                 570                 575
Ala Leu Leu Ile Val Thr Ile Val Val Ile Met Leu Val Leu Gly Leu
            580                 585                 590
Ala Val Ala Phe Cys Cys Leu His Phe Asp Leu Pro Trp Tyr Leu Arg
        595                 600                 605
Met Leu Gly Gln Cys Thr Gln Thr Trp His Arg Val Arg Lys Thr Thr
    610                 615                 620
Gln Glu Gln Leu Lys Arg Asn Val Arg Phe His Ala Phe Ile Ser Tyr
625                 630                 635                 640
Ser Glu His Asp Ser Leu Trp Val Lys Asn Glu Leu Ile Pro Asn Leu
                645                 650                 655
Glu Lys Glu Asp Gly Ser Ile Leu Ile Cys Leu Tyr Glu Ser Tyr Phe
            660                 665                 670
Asp Pro Gly Lys Ser Ile Ser Glu Asn Ile Val Ser Phe Ile Glu Lys
        675                 680                 685
```

```
Ser Tyr Lys Ser Ile Phe Val Leu Ser Pro Asn Phe Val Gln Asn Glu
        690                 695                 700

Trp Cys His Tyr Glu Phe Tyr Phe Ala His His Asn Leu Phe His Glu
705                 710                 715                 720

Asn Ser Asp His Ile Ile Leu Ile Leu Leu Glu Pro Ile Pro Phe Tyr
                725                 730                 735

Cys Ile Pro Thr Arg Tyr His Lys Leu Lys Ala Leu Leu Glu Lys Lys
            740                 745                 750

Ala Tyr Leu Glu Trp Pro Lys Asp Arg Arg Lys Cys Gly Leu Phe Trp
        755                 760                 765

Ala Asn Leu Arg Ala Ala Ile Asn Val Asn Val Leu Ala Thr Arg Glu
    770                 775                 780

Met Tyr Glu Leu Gln Thr Phe Thr Glu Leu Asn Glu Glu Ser Arg Gly
785                 790                 795                 800

Ser Thr Ile Ser Leu Met Arg Thr Asp Cys Leu
                805                 810

<210> SEQ ID NO 49
<211> LENGTH: 509
<212> TYPE: PRT
<213> ORGANISM: Homo Sapiens

<400> SEQUENCE: 49

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
    130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
```

```
                        245                 250                 255
Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
        355                 360                 365

Asn Ile Leu Val Ser Asp Thr Leu Ser Cys Lys Ile Ala Asp Phe Gly
    370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
    450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505

<210> SEQ ID NO 50
<211> LENGTH: 847
<212> TYPE: PRT
<213> ORGANISM: Homo Sapiens

<400> SEQUENCE: 50

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110
```

```
Asp Ser Gly Gln Leu Gly Leu Arg Met Glu Ser Lys Thr Glu Lys Trp
            115                 120                 125
Met Glu Arg Ile His Leu Asn Val Ser Glu Arg Pro Phe Pro Pro His
        130                 135                 140
Ile Gln Leu Pro Pro Glu Ile Gln Glu Ser Gln Glu Val Thr Leu Thr
145                 150                 155                 160
Cys Leu Leu Asn Phe Ser Cys Tyr Gly Tyr Pro Ile Gln Leu Gln Trp
                165                 170                 175
Leu Leu Glu Gly Val Pro Met Arg Gln Ala Ala Val Thr Ser Thr Ser
            180                 185                 190
Leu Thr Ile Lys Ser Val Phe Thr Arg Ser Glu Leu Lys Phe Ser Pro
        195                 200                 205
Gln Trp Ser His His Gly Lys Ile Val Thr Cys Gln Leu Gln Asp Ala
210                 215                 220
Asp Gly Lys Phe Leu Ser Asn Asp Thr Val Gln Leu Asn Val Lys His
225                 230                 235                 240
Thr Pro Lys Leu Glu Ile Lys Val Thr Pro Ser Asp Ala Ile Val Arg
                245                 250                 255
Glu Gly Asp Ser Val Thr Met Thr Cys Glu Val Ser Ser Ser Asn Pro
            260                 265                 270
Glu Tyr Thr Thr Val Ser Trp Leu Lys Asp Gly Thr Ser Leu Lys Lys
        275                 280                 285
Gln Asn Thr Phe Thr Leu Asn Leu Arg Glu Val Thr Lys Asp Gln Ser
290                 295                 300
Gly Lys Tyr Cys Cys Gln Val Ser Asn Asp Val Gly Pro Gly Arg Ser
305                 310                 315                 320
Glu Glu Val Phe Leu Gln Val Gln Tyr Ala Pro Glu Pro Ser Thr Val
                325                 330                 335
Gln Ile Leu His Ser Pro Ala Val Glu Gly Ser Gln Val Glu Phe Leu
            340                 345                 350
Cys Met Ser Leu Ala Asn Pro Leu Pro Thr Asn Tyr Thr Trp Tyr His
        355                 360                 365
Asn Gly Lys Glu Met Gln Gly Arg Thr Glu Glu Lys Val His Ile Pro
370                 375                 380
Lys Ile Leu Pro Trp His Ala Gly Thr Tyr Ser Cys Val Ala Glu Asn
385                 390                 395                 400
Ile Leu Gly Thr Gly Gln Arg Gly Pro Gly Ala Glu Leu Asp Val Gln
                405                 410                 415
Tyr Pro Pro Lys Lys Val Thr Thr Val Ile Gln Asn Pro Met Pro Ile
            420                 425                 430
Arg Glu Gly Asp Thr Val Thr Leu Ser Cys Asn Tyr Asn Ser Ser Asn
        435                 440                 445
Pro Ser Val Thr Arg Tyr Glu Trp Lys Pro His Gly Ala Trp Glu Glu
450                 455                 460
Pro Ser Leu Gly Val Leu Lys Ile Gln Asn Val Gly Trp Asp Asn Thr
465                 470                 475                 480
Thr Ile Ala Cys Ala Ala Cys Asn Ser Trp Cys Ser Trp Ala Ser Pro
                485                 490                 495
Val Ala Leu Asn Val Gln Tyr Ala Pro Arg Asp Val Arg Val Arg Lys
            500                 505                 510
Ile Lys Pro Leu Ser Glu Ile His Ser Gly Asn Ser Val Ser Leu Gln
        515                 520                 525
Cys Asp Phe Ser Ser Ser His Pro Lys Glu Val Gln Phe Phe Trp Glu
```

```
                    530                 535                 540
Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                    565                 570                 575

Ile Gly Gln Thr Ala Ser Lys Ala Trp Thr Leu Glu Val Leu Tyr Ala
                    580                 585                 590

Pro Arg Arg Leu Arg Val Ser Met Ser Pro Gly Asp Gln Val Met Glu
                    595                 600                 605

Gly Lys Ser Ala Thr Leu Thr Cys Glu Ser Asp Ala Asn Pro Pro Val
                    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                    645                 650                 655

Tyr Trp Cys Gln Gly Thr Asn Ser Val Gly Lys Gly Arg Ser Pro Leu
                    660                 665                 670

Ser Thr Leu Thr Val Tyr Tyr Ser Pro Glu Thr Ile Gly Arg Arg Val
                    675                 680                 685

Ala Val Gly Leu Gly Ser Cys Leu Ala Ile Leu Ile Leu Ala Ile Cys
                    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                    725                 730                 735

Val Arg Arg Ala Pro Leu Ser Glu Gly Pro His Ser Leu Gly Cys Tyr
                    740                 745                 750

Asn Pro Met Met Glu Asp Gly Ile Ser Tyr Thr Thr Leu Arg Phe Pro
                    755                 760                 765

Glu Met Asn Ile Pro Arg Thr Gly Asp Ala Glu Ser Ser Glu Met Gln
770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                    805                 810                 815

Asp Glu Gly Ile His Tyr Ser Glu Leu Ile Gln Phe Gly Val Gly Glu
                    820                 825                 830

Arg Pro Gln Ala Gln Glu Asn Val Asp Tyr Val Ile Leu Lys His
                    835                 840                 845

<210> SEQ ID NO 51
<211> LENGTH: 807
<212> TYPE: PRT
<213> ORGANISM: Homo Sapiens

<400> SEQUENCE: 51

Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
                20                  25                  30

Arg Gln Ser Thr Lys Tyr Lys Ala Asp Lys Thr Tyr Pro Thr Thr Val
            35                  40                  45

Ala Glu Lys Pro Lys Asn Ile Lys Lys Asn Arg Tyr Lys Asp Ile Leu
50                  55                  60
```

```
Pro Tyr Asp Tyr Ser Arg Val Glu Leu Ser Leu Ile Thr Ser Asp Glu
 65              70                  75                  80

Asp Ser Ser Tyr Ile Asn Ala Asn Phe Ile Lys Gly Val Tyr Gly Pro
                 85                  90                  95

Lys Ala Tyr Ile Ala Thr Gln Gly Pro Leu Ser Thr Thr Leu Leu Asp
                100                 105                 110

Phe Trp Arg Met Ile Trp Glu Tyr Ser Val Leu Ile Ile Val Met Ala
            115                 120                 125

Cys Met Glu Tyr Glu Met Gly Lys Lys Cys Glu Arg Tyr Trp Ala
        130                 135                 140

Glu Pro Gly Glu Met Gln Leu Glu Phe Gly Pro Phe Ser Val Ser Cys
145                 150                 155                 160

Glu Ala Glu Lys Arg Lys Ser Asp Tyr Ile Ile Arg Thr Leu Lys Val
                165                 170                 175

Lys Phe Asn Ser Glu Thr Arg Thr Ile Tyr Gln Phe His Tyr Lys Asn
                180                 185                 190

Trp Pro Asp His Asp Val Pro Ser Ser Ile Asp Pro Ile Leu Glu Leu
                195                 200                 205

Ile Trp Asp Val Arg Cys Tyr Gln Glu Asp Asp Ser Val Pro Ile Cys
210                 215                 220

Ile His Cys Ser Ala Gly Cys Gly Arg Thr Gly Val Ile Cys Ala Ile
225                 230                 235                 240

Asp Tyr Thr Trp Met Leu Leu Lys Asp Gly Ile Ile Pro Glu Asn Phe
                245                 250                 255

Ser Val Phe Ser Leu Ile Arg Glu Met Arg Thr Gln Arg Pro Ser Leu
                260                 265                 270

Val Gln Thr Gln Glu Gln Tyr Glu Leu Val Tyr Asn Ala Val Leu Glu
            275                 280                 285

Leu Phe Lys Arg Gln Met Asp Val Ile Arg Asp Lys His Ser Gly Thr
            290                 295                 300

Glu Ser Gln Ala Lys His Cys Ile Pro Glu Lys Asn His Thr Leu Gln
305                 310                 315                 320

Ala Asp Ser Tyr Ser Pro Asn Leu Pro Lys Ser Thr Thr Lys Ala Ala
                325                 330                 335

Lys Met Met Asn Gln Gln Arg Thr Lys Met Glu Ile Lys Glu Ser Ser
            340                 345                 350

Ser Phe Asp Phe Arg Thr Ser Glu Ile Ser Ala Lys Glu Glu Leu Val
            355                 360                 365

Leu His Pro Ala Lys Ser Ser Thr Ser Phe Asp Phe Leu Glu Leu Asn
    370                 375                 380

Tyr Ser Phe Asp Lys Asn Ala Asp Thr Thr Met Lys Trp Gln Thr Lys
385                 390                 395                 400

Ala Phe Pro Ile Val Gly Glu Pro Leu Gln Lys His Gln Ser Leu Asp
                405                 410                 415

Leu Gly Ser Leu Leu Phe Glu Gly Cys Ser Asn Ser Lys Pro Val Asn
                420                 425                 430

Ala Ala Gly Arg Tyr Phe Asn Ser Lys Val Pro Ile Thr Arg Thr Lys
            435                 440                 445

Ser Thr Pro Phe Glu Leu Ile Gln Gln Arg Glu Thr Lys Glu Val Asp
            450                 455                 460

Ser Lys Glu Asn Phe Ser Tyr Leu Glu Ser Gln Pro His Asp Ser Cys
465                 470                 475                 480

Phe Val Glu Met Gln Ala Gln Lys Val Met His Val Ser Ser Ala Glu
```

```
                    485                 490                 495

Leu Asn Tyr Ser Leu Pro Tyr Asp Ser Lys His Gln Ile Arg Asn Ala
                500                 505                 510

Ser Asn Val Lys His His Asp Ser Ala Leu Gly Val Tyr Ser Tyr
                515                 520                 525

Ile Pro Leu Val Glu Asn Pro Tyr Phe Ser Ser Trp Pro Pro Ser Gly
            530                 535                 540

Thr Ser Ser Lys Met Ser Leu Asp Leu Pro Glu Lys Gln Asp Gly Thr
545                 550                 555                 560

Val Phe Pro Ser Leu Leu Pro Thr Ser Ser Thr Ser Leu Phe Ser
                565                 570                 575

Tyr Tyr Asn Ser His Asp Ser Leu Ser Leu Asn Ser Pro Thr Asn Ile
                580                 585                 590

Ser Ser Leu Leu Asn Gln Glu Ser Ala Val Leu Ala Thr Ala Pro Arg
                595                 600                 605

Ile Asp Asp Glu Ile Pro Pro Pro Leu Pro Val Arg Thr Pro Glu Ser
            610                 615                 620

Phe Ile Val Val Glu Glu Ala Gly Glu Phe Ser Pro Asn Val Pro Lys
625                 630                 635                 640

Ser Leu Ser Ser Ala Val Lys Val Lys Ile Gly Thr Ser Leu Glu Trp
                645                 650                 655

Gly Gly Thr Ser Glu Pro Lys Lys Phe Asp Asp Ser Val Ile Leu Arg
                660                 665                 670

Pro Ser Lys Ser Val Lys Leu Arg Ser Pro Lys Ser Glu Leu His Gln
            675                 680                 685

Asp Arg Ser Ser Pro Pro Pro Leu Pro Glu Arg Thr Leu Glu Ser
            690                 695                 700

Phe Phe Leu Ala Asp Glu Asp Cys Met Gln Ala Gln Ser Ile Glu Thr
705                 710                 715                 720

Tyr Ser Thr Ser Tyr Pro Asp Thr Met Glu Asn Ser Thr Ser Ser Lys
                725                 730                 735

Gln Thr Leu Lys Thr Pro Gly Lys Ser Phe Thr Arg Ser Lys Ser Leu
                740                 745                 750

Lys Ile Leu Arg Asn Met Lys Lys Ser Ile Cys Asn Ser Cys Pro Pro
                755                 760                 765

Asn Lys Pro Ala Glu Ser Val Gln Ser Asn Asn Ser Ser Phe Leu
                770                 775                 780

Asn Phe Gly Phe Ala Asn Arg Phe Ser Lys Pro Lys Gly Pro Arg Asn
785                 790                 795                 800

Pro Pro Pro Thr Trp Asn Ile
                805

<210> SEQ ID NO 52
<211> LENGTH: 706
<212> TYPE: PRT
<213> ORGANISM: Homo Sapiens

<400> SEQUENCE: 52

Met Ala Ser Pro Ala Asp Ser Cys Ile Gln Phe Thr Arg His Ala Ser
1               5                   10                  15

Asp Val Leu Leu Asn Leu Asn Arg Leu Arg Ser Arg Asp Ile Leu Thr
                20                  25                  30

Asp Val Val Ile Val Val Ser Arg Glu Gln Phe Arg Ala His Lys Thr
            35                  40                  45
```

```
Val Leu Met Ala Cys Ser Gly Leu Phe Tyr Ser Ile Phe Thr Asp Gln
 50                  55                  60
Leu Lys Cys Asn Leu Ser Val Ile Asn Leu Asp Pro Glu Ile Asn Pro
 65                  70                  75                  80
Glu Gly Phe Cys Ile Leu Leu Asp Phe Met Tyr Thr Ser Arg Leu Asn
                 85                  90                  95
Leu Arg Glu Gly Asn Ile Met Ala Val Met Ala Thr Ala Met Tyr Leu
                100                 105                 110
Gln Met Glu His Val Val Asp Thr Cys Arg Lys Phe Ile Lys Ala Ser
                115                 120                 125
Glu Ala Glu Met Val Ser Ala Ile Lys Pro Pro Arg Glu Glu Phe Leu
130                 135                 140
Asn Ser Arg Met Leu Met Pro Gln Asp Ile Met Ala Tyr Arg Gly Arg
145                 150                 155                 160
Glu Val Val Glu Asn Asn Leu Pro Leu Arg Ser Ala Pro Gly Cys Glu
                165                 170                 175
Ser Arg Ala Phe Ala Pro Ser Leu Tyr Ser Gly Leu Ser Thr Pro Pro
                180                 185                 190
Ala Ser Tyr Ser Met Tyr Ser His Leu Pro Val Ser Ser Leu Leu Phe
                195                 200                 205
Ser Asp Glu Glu Phe Arg Asp Val Arg Met Pro Val Ala Asn Pro Phe
210                 215                 220
Pro Lys Glu Arg Ala Leu Pro Cys Asp Ser Ala Arg Pro Val Pro Gly
225                 230                 235                 240
Glu Tyr Ser Arg Pro Thr Leu Glu Val Ser Pro Asn Val Cys His Ser
                245                 250                 255
Asn Ile Tyr Ser Pro Lys Glu Thr Ile Pro Glu Glu Ala Arg Ser Asp
                260                 265                 270
Met His Tyr Ser Val Ala Glu Gly Leu Lys Pro Ala Ala Pro Ser Ala
                275                 280                 285
Arg Asn Ala Pro Tyr Phe Pro Cys Asp Lys Ala Ser Lys Glu Glu Glu
290                 295                 300
Arg Pro Ser Ser Glu Asp Glu Ile Ala Leu His Phe Glu Pro Pro Asn
305                 310                 315                 320
Ala Pro Leu Asn Arg Lys Gly Leu Val Ser Pro Gln Ser Pro Gln Lys
                325                 330                 335
Ser Asp Cys Gln Pro Asn Ser Pro Thr Glu Ser Cys Ser Ser Lys Asn
                340                 345                 350
Ala Cys Ile Leu Gln Ala Ser Gly Ser Pro Pro Ala Lys Ser Pro Thr
                355                 360                 365
Asp Pro Lys Ala Cys Asn Trp Lys Lys Tyr Lys Phe Ile Val Leu Asn
370                 375                 380
Ser Leu Asn Gln Asn Ala Lys Pro Glu Gly Pro Glu Gln Ala Glu Leu
385                 390                 395                 400
Gly Arg Leu Ser Pro Arg Ala Tyr Thr Ala Pro Ala Cys Gln Pro
                405                 410                 415
Pro Met Glu Pro Glu Asn Leu Asp Leu Gln Ser Pro Thr Lys Leu Ser
                420                 425                 430
Ala Ser Gly Glu Asp Ser Thr Ile Pro Gln Ala Ser Arg Leu Asn Asn
                435                 440                 445
Ile Val Asn Arg Ser Met Thr Gly Ser Pro Arg Ser Ser Ser Glu Ser
450                 455                 460
His Ser Pro Leu Tyr Met His Pro Pro Lys Cys Thr Ser Cys Gly Ser
```

```
            465                 470                 475                 480
        Gln Ser Pro Gln His Ala Glu Met Cys Leu His Thr Ala Gly Pro Thr
                        485                 490                 495

Phe Pro Glu Glu Met Gly Glu Thr Gln Ser Glu Tyr Ser Asp Ser Ser
                    500                 505                 510

Cys Glu Asn Gly Ala Phe Phe Cys Asn Glu Cys Asp Cys Arg Phe Ser
                515                 520                 525

Glu Glu Ala Ser Leu Lys Arg His Thr Leu Gln Thr His Ser Asp Lys
            530                 535                 540

Pro Tyr Lys Cys Asp Arg Cys Gln Ala Ser Phe Arg Tyr Lys Gly Asn
        545                 550                 555                 560

Leu Ala Ser His Lys Thr Val His Thr Gly Glu Lys Pro Tyr Arg Cys
                        565                 570                 575

Asn Ile Cys Gly Ala Gln Phe Asn Arg Pro Ala Asn Leu Lys Thr His
                    580                 585                 590

Thr Arg Ile His Ser Gly Glu Lys Pro Tyr Lys Cys Glu Thr Cys Gly
                595                 600                 605

Ala Arg Phe Val Gln Val Ala His Leu Arg Ala His Val Leu Ile His
            610                 615                 620

Thr Gly Glu Lys Pro Tyr Pro Cys Glu Ile Cys Gly Thr Arg Phe Arg
        625                 630                 635                 640

His Leu Gln Thr Leu Lys Ser His Leu Arg Ile His Thr Gly Glu Lys
                        645                 650                 655

Pro Tyr His Cys Glu Lys Cys Asn Leu His Phe Arg His Lys Ser Gln
                    660                 665                 670

Leu Arg Leu His Leu Arg Gln Lys His Gly Ala Ile Thr Asn Thr Lys
                675                 680                 685

Val Gln Tyr Arg Val Ser Ala Thr Asp Leu Pro Pro Glu Leu Pro Lys
            690                 695                 700

Ala Cys
        705

<210> SEQ ID NO 53
<211> LENGTH: 263
<212> TYPE: PRT
<213> ORGANISM: Homo Sapiens

<400> SEQUENCE: 53

Met Leu Leu Ala Trp Val Gln Ala Phe Leu Val Ser Asn Met Leu Leu
        1               5                   10                  15

Ala Glu Ala Tyr Gly Ser Gly Gly Cys Phe Trp Asp Asn Gly His Leu
                        20                  25                  30

Tyr Arg Glu Asp Gln Thr Ser Pro Ala Pro Gly Leu Arg Cys Leu Asn
                    35                  40                  45

Trp Leu Asp Ala Gln Ser Gly Leu Ala Ser Ala Pro Val Ser Gly Ala
                50                  55                  60

Gly Asn His Ser Tyr Cys Arg Asn Pro Asp Glu Asp Pro Arg Gly Pro
        65                  70                  75                  80

Trp Cys Tyr Val Ser Gly Glu Ala Gly Val Pro Glu Lys Arg Pro Cys
                        85                  90                  95

Glu Asp Leu Arg Cys Pro Glu Thr Thr Ser Gln Ala Leu Pro Ala Phe
                    100                 105                 110

Thr Thr Glu Ile Gln Glu Ala Ser Glu Gly Pro Gly Ala Asp Glu Val
                115                 120                 125
```

```
Gln Val Phe Ala Pro Ala Asn Ala Leu Pro Ala Arg Ser Glu Ala Ala
    130                 135                 140

Ala Val Gln Pro Val Ile Gly Ile Ser Gln Arg Val Arg Met Asn Ser
145                 150                 155                 160

Lys Glu Lys Lys Asp Leu Gly Thr Leu Gly Tyr Val Leu Gly Ile Thr
                165                 170                 175

Met Met Val Ile Ile Ile Ala Ile Gly Ala Gly Ile Ile Leu Gly Tyr
            180                 185                 190

Ser Tyr Lys Arg Gly Lys Asp Leu Lys Glu Gln His Asp Gln Lys Val
        195                 200                 205

Cys Glu Arg Glu Met Gln Arg Ile Thr Leu Pro Leu Ser Ala Phe Thr
    210                 215                 220

Asn Pro Thr Cys Glu Ile Val Asp Glu Lys Thr Val Val His Thr
225                 230                 235                 240

Ser Gln Thr Pro Val Asp Pro Gln Glu Gly Thr Thr Pro Leu Met Gly
                245                 250                 255

Gln Ala Gly Thr Pro Gly Ala
            260
```

<210> SEQ ID NO 54
<211> LENGTH: 156
<212> TYPE: PRT
<213> ORGANISM: Homo Sapiens

<400> SEQUENCE: 54

```
Met Glu Pro Ala Ala Gly Ser Ser Met Glu Pro Ser Ala Asp Trp Leu
1               5                   10                  15

Ala Thr Ala Ala Ala Arg Gly Arg Val Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
        50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
        130                 135                 140

Ile Asp Ala Ala Glu Gly Pro Ser Asp Ile Pro Asp
145                 150                 155
```

<210> SEQ ID NO 55
<211> LENGTH: 1226
<212> TYPE: PRT
<213> ORGANISM: Homo Sapiens

<400> SEQUENCE: 55

```
Met Asp Ser Phe Asp Leu Ala Leu Leu Gln Glu Trp Asp Leu Glu Ser
1               5                   10                  15

Leu Cys Val Tyr Glu Pro Asp Arg Asn Ala Leu Arg Arg Lys Glu Arg
                20                  25                  30
```

-continued

```
Glu Arg Arg Asn Gln Glu Thr Gln Gln Asp Asp Gly Thr Phe Asn Ser
         35                  40                  45

Ser Tyr Ser Leu Phe Ser Glu Pro Tyr Lys Thr Asn Lys Gly Asp Glu
 50                  55                  60

Leu Ser Asn Arg Ile Gln Asn Thr Leu Gly Asn Tyr Asp Glu Met Lys
 65                  70                  75                  80

Asp Phe Leu Thr Asp Arg Ser Asn Gln Ser His Leu Val Gly Val Pro
                 85                  90                  95

Lys Pro Gly Val Pro Gln Thr Pro Val Asn Lys Ile Asp Glu His Phe
                100                 105                 110

Val Ala Asp Ser Arg Ala Gln Asn Gln Pro Ser Ser Ile Cys Ser Thr
            115                 120                 125

Thr Thr Ser Thr Pro Ala Ala Val Pro Val Gln Gln Ser Lys Arg Gly
        130                 135                 140

Thr Met Gly Trp Gln Lys Ala Gly His Pro Pro Ser Asp Gly Gln Gln
145                 150                 155                 160

Arg Ala Thr Gln Gln Gly Ser Leu Arg Thr Leu Leu Gly Asp Gly Val
                165                 170                 175

Gly Arg Gln Gln Pro Arg Ala Lys Gln Val Cys Asn Val Glu Val Gly
            180                 185                 190

Leu Gln Thr Gln Glu Arg Pro Pro Ala Met Ala Ala Lys His Ser Ser
        195                 200                 205

Ser Gly His Cys Val Gln Asn Phe Pro Pro Ser Leu Ala Ser Lys Pro
    210                 215                 220

Ser Leu Val Gln Gln Lys Pro Thr Ala Tyr Val Arg Pro Met Asp Gly
225                 230                 235                 240

Gln Asp Gln Ala Pro Asp Glu Ser Pro Lys Leu Lys Ser Ser Ser Glu
                245                 250                 255

Thr Ser Val His Cys Thr Ser Tyr Arg Gly Val Pro Ala Ser Lys Pro
            260                 265                 270

Glu Pro Ala Arg Ala Lys Ala Lys Leu Ser Lys Phe Ser Ile Pro Lys
        275                 280                 285

Gln Gly Glu Glu Ser Arg Ser Gly Glu Thr Asn Ser Cys Val Glu Glu
    290                 295                 300

Ile Ile Arg Glu Met Thr Trp Leu Pro Pro Leu Ser Ala Ile Gln Ala
305                 310                 315                 320

Pro Gly Lys Val Glu Pro Thr Lys Phe Pro Phe Pro Asn Lys Asp Ser
                325                 330                 335

Gln Leu Val Ser Ser Gly His Asn Asn Pro Lys Lys Gly Asp Ala Glu
            340                 345                 350

Pro Glu Ser Pro Asp Ser Gly Thr Ser Asn Thr Ser Met Leu Glu Asp
        355                 360                 365

Asp Leu Lys Leu Ser Ser Asp Glu Glu Glu Asn Glu Gln Gln Ala Ala
    370                 375                 380

Gln Arg Thr Ala Leu Arg Ala Leu Ser Asp Ser Ala Val Val Gln Gln
385                 390                 395                 400

Pro Asn Cys Arg Thr Ser Val Pro Ser Ser Lys Gly Ser Ser Ser Ser
                405                 410                 415

Ser Ser Ser Gly Ser Ser Ser Ser Ser Asp Ser Glu Ser Ser Ser Ser
            420                 425                 430

Gly Ser Asp Ser Glu Thr Glu Ser Ser Ser Ser Glu Ser Glu Gly Ser
        435                 440                 445

Lys Pro Pro His Phe Ser Ser Pro Glu Ala Glu Pro Ala Ser Ser Asn
```

```
              450                 455                 460
Lys Trp Gln Leu Asp Lys Trp Leu Asn Lys Val Asn Pro His Lys Pro
465                 470                 475                 480

Pro Ile Leu Ile Gln Asn Glu Ser His Gly Ser Glu Ser Asn Gln Tyr
                485                 490                 495

Tyr Asn Pro Val Lys Glu Asp Val Gln Asp Cys Gly Lys Val Pro Asp
                500                 505                 510

Val Cys Gln Pro Ser Leu Arg Glu Lys Glu Ile Lys Ser Thr Cys Lys
                515                 520                 525

Glu Glu Gln Arg Pro Arg Thr Ala Asn Lys Ala Pro Gly Ser Lys Gly
            530                 535                 540

Val Lys Gln Lys Ser Pro Ala Ala Val Ala Val Ala Val Ser Ala
545                 550                 555                 560

Ala Ala Pro Pro Ala Val Pro Cys Ala Pro Ala Glu Asn Ala Pro
                565                 570                 575

Ala Pro Ala Arg Arg Ser Ala Gly Lys Lys Pro Thr Arg Arg Thr Glu
                580                 585                 590

Arg Thr Ser Ala Gly Asp Gly Ala Asn Cys His Arg Pro Glu Glu Pro
            595                 600                 605

Ala Ala Ala Asp Ala Leu Gly Thr Ser Val Val Pro Pro Glu Pro
            610                 615                 620

Thr Lys Thr Arg Pro Cys Gly Asn Asn Arg Ala Ser His Arg Lys Glu
625                 630                 635                 640

Leu Arg Ser Ser Val Thr Cys Glu Lys Arg Thr Arg Gly Leu Ser
                645                 650                 655

Arg Ile Val Pro Lys Ser Lys Glu Phe Ile Glu Thr Glu Ser Ser Ser
                660                 665                 670

Ser Ser Ser Ser Asp Ser Asp Leu Glu Ser Glu Gln Glu Glu Tyr
            675                 680                 685

Pro Leu Ser Lys Ala Gln Thr Val Ala Ala Ser Ala Ser Ser Gly Asn
            690                 695                 700

Asp Gln Arg Leu Lys Glu Ala Ala Ala Asn Gly Gly Ser Gly Pro Arg
705                 710                 715                 720

Ala Pro Val Gly Ser Ile Asn Ala Arg Thr Thr Ser Asp Ile Ala Lys
                725                 730                 735

Glu Leu Glu Glu Gln Phe Tyr Thr Leu Val Pro Phe Gly Arg Asn Glu
                740                 745                 750

Leu Leu Ser Pro Leu Lys Asp Ser Asp Glu Ile Arg Ser Leu Trp Val
                755                 760                 765

Lys Ile Asp Leu Thr Leu Leu Ser Arg Ile Pro Glu His Leu Pro Gln
770                 775                 780

Glu Pro Gly Val Leu Ser Ala Pro Ala Thr Lys Asp Ser Glu Ser Ala
785                 790                 795                 800

Pro Pro Ser His Thr Ser Asp Thr Pro Ala Glu Lys Ala Leu Pro Lys
                805                 810                 815

Ser Lys Arg Lys Arg Lys Cys Asp Asn Glu Asp Asp Tyr Arg Glu Ile
                820                 825                 830

Lys Lys Ser Gln Gly Glu Lys Asp Ser Ser Arg Leu Ala Thr Ser
            835                 840                 845

Thr Ser Asn Thr Leu Ser Ala Asn His Cys Asn Met Asn Ile Asn Ser
            850                 855                 860

Val Ala Ile Pro Ile Asn Lys Asn Glu Lys Met Leu Arg Ser Pro Ile
865                 870                 875                 880
```

```
Ser Pro Leu Ser Asp Ala Ser Lys His Lys Tyr Thr Ser Glu Asp Leu
            885                 890                 895

Thr Ser Ser Arg Pro Asn Gly Asn Ser Leu Phe Thr Ser Ala Ser
        900                 905                 910

Ser Ser Lys Lys Pro Lys Ala Asp Ser Gln Leu Gln Pro His Gly Gly
        915                 920                 925

Asp Leu Thr Lys Ala Ala His Asn Asn Ser Glu Asn Ile Pro Leu His
    930                 935                 940

Lys Ser Arg Pro Gln Thr Lys Pro Trp Ser Pro Gly Ser Asn Gly His
945                 950                 955                 960

Arg Asp Cys Lys Arg Gln Lys Leu Val Phe Asp Met Pro Arg Ser
            965                 970                 975

Ala Asp Tyr Phe Met Gln Glu Ala Lys Arg Met Lys His Lys Ala Asp
            980                 985                 990

Ala Met Val Glu Lys Phe Gly Lys Ala Leu Asn Tyr Ala Glu Ala Ala
            995                 1000                1005

Leu Ser Phe Ile Glu Cys Gly Asn Ala Met Glu Gln Gly Pro Met
    1010                1015                1020

Glu Ser Lys Ser Pro Tyr Thr Met Tyr Ser Glu Thr Val Glu Leu
    1025                1030                1035

Ile Arg Tyr Ala Met Arg Leu Lys Thr His Ser Gly Pro Asn Ala
    1040                1045                1050

Thr Pro Glu Asp Lys Gln Leu Ala Ala Leu Cys Tyr Arg Cys Leu
    1055                1060                1065

Ala Leu Leu Tyr Trp Arg Met Phe Arg Leu Lys Arg Asp His Ala
    1070                1075                1080

Val Lys Tyr Ser Lys Ala Leu Ile Asp Tyr Phe Lys Asn Ser Ser
    1085                1090                1095

Lys Ala Ala Gln Ala Pro Ser Pro Trp Gly Ala Ser Gly Lys Ser
    1100                1105                1110

Thr Gly Thr Pro Ser Pro Met Ser Pro Asn Pro Ser Pro Ala Ser
    1115                1120                1125

Ser Val Gly Ser Gln Gly Ser Leu Ser Asn Ala Ser Ala Leu Ser
    1130                1135                1140

Pro Ser Thr Ile Val Ser Ile Pro Gln Arg Ile His Gln Met Ala
    1145                1150                1155

Ala Asn His Val Ser Ile Thr Asn Ser Ile Leu His Ser Tyr Asp
    1160                1165                1170

Tyr Trp Glu Met Ala Asp Asn Leu Ala Lys Glu Asn Arg Glu Phe
    1175                1180                1185

Phe Asn Asp Leu Asp Leu Leu Met Gly Pro Val Thr Leu His Ser
    1190                1195                1200

Ser Met Glu His Leu Val Gln Tyr Ser Gln Gln Gly Leu His Trp
    1205                1210                1215

Leu Arg Asn Ser Ala His Leu Ser
    1220                1225

<210> SEQ ID NO 56
<211> LENGTH: 404
<212> TYPE: PRT
<213> ORGANISM: Homo Sapiens

<400> SEQUENCE: 56

Met Pro His Glu Pro His Glu Pro Leu Thr Pro Pro Phe Ser Ala Leu
```

```
              1               5              10              15
        Pro Asp Pro Ala Gly Ala Pro Ser Arg Arg Gln Ser Arg Gln Arg Pro
                         20              25              30

Gln Leu Ser Ser Asp Ser Pro Ser Ala Phe Arg Ala Ser Arg Ser His
                         35              40              45

Ser Arg Asn Ala Thr Arg Ser His Ser His Ser His Ser Pro Arg His
         50                          55              60

Ser Leu Arg His Ser Pro Gly Ser Gly Ser Cys Gly Ser Ser Ser Gly
         65                  70              75                      80

His Arg Pro Cys Ala Asp Ile Leu Glu Val Gly Met Leu Leu Ser Lys
                         85              90              95

Ile Asn Ser Leu Ala His Leu Arg Ala Ala Pro Cys Asn Asp Leu His
                        100             105             110

Ala Thr Lys Leu Ala Pro Gly Lys Glu Lys Glu Pro Leu Glu Ser Gln
                        115             120             125

Tyr Gln Val Gly Pro Leu Leu Gly Ser Gly Phe Gly Ser Val Tyr
                        130             135             140

Ser Gly Ile Arg Val Ser Asp Asn Leu Pro Val Ala Ile Lys His Val
        145                         150             155                 160

Glu Lys Asp Arg Ile Ser Asp Trp Gly Glu Leu Pro Asn Gly Thr Arg
                            165             170             175

Val Pro Met Glu Val Val Leu Leu Lys Lys Val Ser Ser Gly Phe Ser
                        180             185             190

Gly Val Ile Arg Leu Leu Asp Trp Phe Glu Arg Pro Asp Ser Phe Val
                        195             200             205

Leu Ile Leu Glu Arg Pro Glu Pro Val Gln Asp Leu Phe Asp Phe Ile
        210                         215             220

Thr Glu Arg Gly Ala Leu Gln Glu Glu Leu Ala Arg Ser Phe Phe Trp
        225                         230             235                 240

Gln Val Leu Glu Ala Val Arg His Cys His Asn Cys Gly Val Leu His
                        245             250             255

Arg Asp Ile Lys Asp Glu Asn Ile Leu Ile Asp Leu Asn Arg Gly Glu
                        260             265             270

Leu Lys Leu Ile Asp Phe Gly Ser Gly Ala Leu Leu Lys Asp Thr Val
                        275             280             285

Tyr Thr Asp Phe Asp Gly Thr Arg Val Tyr Ser Pro Pro Glu Trp Ile
                        290             295             300

Arg Tyr His Arg Tyr His Gly Arg Ser Ala Ala Val Trp Ser Leu Gly
        305                         310             315                 320

Ile Leu Leu Tyr Asp Met Val Cys Gly Asp Ile Pro Phe Glu His Asp
                        325             330             335

Glu Glu Ile Ile Arg Gly Gln Val Phe Phe Arg Gln Arg Val Ser Ser
                        340             345             350

Glu Cys Gln His Leu Ile Arg Trp Cys Leu Ala Leu Arg Pro Ser Asp
                        355             360             365

Arg Pro Thr Phe Glu Glu Ile Gln Asn His Pro Trp Met Gln Asp Val
                370             375             380

Leu Leu Pro Gln Glu Thr Ala Glu Ile His Leu His Ser Leu Ser Pro
        385                         390             395                 400

Gly Pro Ser Lys

<210> SEQ ID NO 57
<211> LENGTH: 207
```

<212> TYPE: PRT
<213> ORGANISM: Homo Sapiens

<400> SEQUENCE: 57

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Pro Ile Leu Ile Pro
    130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205

<210> SEQ ID NO 58
<211> LENGTH: 736
<212> TYPE: PRT
<213> ORGANISM: Homo Sapiens

<400> SEQUENCE: 58

Met Lys Lys Ser Arg Ser Val Met Thr Val Met Ala Asp Asp Asn Val
1               5                   10                  15

Lys Asp Tyr Phe Glu Cys Ser Leu Ser Lys Ser Tyr Ser Ser Ser Ser
            20                  25                  30

Asn Thr Leu Gly Ile Asp Leu Trp Arg Gly Arg Arg Cys Cys Ser Gly
        35                  40                  45

Asn Leu Gln Leu Pro Pro Leu Ser Gln Arg Gln Ser Glu Arg Ala Arg
    50                  55                  60

Thr Pro Glu Gly Asp Gly Ile Ser Arg Pro Thr Thr Leu Pro Leu Thr
65                  70                  75                  80

Thr Leu Pro Ser Ile Ala Ile Thr Thr Val Ser Gln Glu Cys Phe Asp
                85                  90                  95

Val Glu Asn Gly Pro Ser Pro Gly Arg Ser Pro Leu Asp Pro Gln Ala
            100                 105                 110

Ser Ser Ser Ala Gly Leu Val Leu His Ala Thr Phe Pro Gly His Ser
        115                 120                 125

Gln Arg Arg Glu Ser Phe Leu Tyr Arg Ser Asp Ser Asp Tyr Asp Leu
    130                 135                 140

-continued

```
Ser Pro Lys Ala Met Ser Arg Asn Ser Ser Leu Pro Ser Glu Gln His
145                 150                 155                 160

Gly Asp Asp Leu Ile Val Thr Pro Phe Ala Gln Val Leu Ala Ser Leu
                165                 170                 175

Arg Ser Val Arg Asn Asn Phe Thr Ile Leu Thr Asn Leu His Gly Thr
            180                 185                 190

Ser Asn Lys Arg Ser Pro Ala Ala Ser Gln Pro Pro Val Ser Arg Val
        195                 200                 205

Asn Pro Gln Glu Glu Ser Tyr Gln Lys Leu Ala Met Glu Thr Leu Glu
    210                 215                 220

Glu Leu Asp Trp Cys Leu Asp Gln Leu Glu Thr Ile Gln Thr Tyr Arg
225                 230                 235                 240

Ser Val Ser Glu Met Ala Ser Asn Lys Phe Lys Arg Met Leu Asn Arg
                245                 250                 255

Glu Leu Thr His Leu Ser Glu Met Ser Arg Ser Gly Asn Gln Val Ser
                260                 265                 270

Glu Tyr Ile Ser Asn Thr Phe Leu Asp Lys Gln Asn Asp Val Glu Ile
            275                 280                 285

Pro Ser Pro Thr Gln Lys Asp Arg Glu Lys Lys Lys Gln Gln Leu
        290                 295                 300

Met Thr Gln Ile Ser Gly Val Lys Lys Leu Met His Ser Ser Ser Leu
305                 310                 315                 320

Asn Asn Thr Ser Ile Ser Arg Phe Gly Val Asn Thr Glu Asn Glu Asp
                325                 330                 335

His Leu Ala Lys Glu Leu Glu Asp Leu Asn Lys Trp Gly Leu Asn Ile
                340                 345                 350

Phe Asn Val Ala Gly Tyr Ser His Asn Arg Pro Leu Thr Cys Ile Met
            355                 360                 365

Tyr Ala Ile Phe Gln Glu Arg Asp Leu Leu Lys Thr Phe Arg Ile Ser
            370                 375                 380

Ser Asp Thr Phe Ile Thr Tyr Met Met Thr Leu Glu Asp His Tyr His
385                 390                 395                 400

Ser Asp Val Ala Tyr His Asn Ser Leu His Ala Ala Asp Val Ala Gln
                405                 410                 415

Ser Thr His Val Leu Leu Ser Thr Pro Ala Leu Asp Ala Val Phe Thr
                420                 425                 430

Asp Leu Glu Ile Leu Ala Ala Ile Phe Ala Ala Ala Ile His Asp Val
            435                 440                 445

Asp His Pro Gly Val Ser Asn Gln Phe Leu Ile Asn Thr Asn Ser Glu
    450                 455                 460

Leu Ala Leu Met Tyr Asn Asp Glu Ser Val Leu Glu Asn His His Leu
465                 470                 475                 480

Ala Val Gly Phe Lys Leu Leu Gln Glu Glu His Cys Asp Ile Phe Met
                485                 490                 495

Asn Leu Thr Lys Lys Gln Arg Gln Thr Leu Arg Lys Met Val Ile Asp
            500                 505                 510

Met Val Leu Ala Thr Asp Met Ser Lys His Met Ser Leu Leu Ala Asp
515                 520                 525

Leu Lys Thr Met Val Glu Thr Lys Lys Val Thr Ser Ser Gly Val Leu
            530                 535                 540

Leu Leu Asp Asn Tyr Thr Asp Arg Ile Gln Val Leu Arg Asn Met Val
545                 550                 555                 560

His Cys Ala Asp Leu Ser Asn Pro Thr Lys Ser Leu Glu Leu Tyr Arg
```

```
                        565                 570                 575
Gln Trp Thr Asp Arg Ile Met Glu Glu Phe Phe Gln Gln Gly Asp Lys
                580                 585                 590
Glu Arg Glu Arg Gly Met Glu Ile Ser Pro Met Cys Asp Lys His Thr
            595                 600                 605
Ala Ser Val Glu Lys Ser Gln Val Gly Phe Ile Asp Tyr Ile Val His
        610                 615                 620
Pro Leu Trp Glu Thr Trp Ala Asp Leu Val Gln Pro Asp Ala Gln Asp
625                 630                 635                 640
Ile Leu Asp Thr Leu Glu Asp Asn Arg Asn Trp Tyr Gln Ser Met Ile
                645                 650                 655
Pro Gln Ser Pro Ser Pro Leu Asp Glu Gln Asn Arg Asp Cys Gln
                660                 665                 670
Gly Leu Met Glu Lys Phe Gln Phe Glu Leu Thr Leu Asp Glu Glu Asp
            675                 680                 685
Ser Glu Gly Pro Glu Lys Glu Gly Gly His Ser Tyr Phe Ser Ser
        690                 695                 700
Thr Lys Thr Leu Cys Val Ile Asp Pro Glu Asn Arg Asp Ser Leu Gly
705                 710                 715                 720
Glu Thr Asp Ile Asp Ile Ala Thr Glu Asp Lys Ser Pro Val Asp Thr
                725                 730                 735

<210> SEQ ID NO 59
<211> LENGTH: 500
<212> TYPE: PRT
<213> ORGANISM: Homo Sapiens

<400> SEQUENCE: 59

Met Asn Gln Arg Arg Ser Glu Ser Arg Pro Gly Asn His Arg Leu Gln
1               5                   10                  15
Ala Tyr Ala Glu Pro Gly Lys Gly Asp Ser Gly Gly Ala Gly Pro Leu
            20                  25                  30
Ser Gly Ser Ala Arg Arg Gly Arg Gly Gly Gly Ala Ile Arg Val
        35                  40                  45
Arg Arg Pro Cys Trp Ser Gly Ala Gly Arg Gly Gly Pro Ala
50                  55                  60
Trp Ala Val Arg Leu Pro Thr Val Thr Ala Gly Trp Thr Trp Pro Ala
65                  70                  75                  80
Leu Arg Thr Leu Ser Ser Leu Arg Ala Gly Pro Ser Glu Pro His Ser
                85                  90                  95
Pro Gly Arg Arg Pro Pro Arg Ala Gly Arg Pro Leu Cys Gln Ala Asp
            100                 105                 110
Pro Gln Pro Gly Lys Ala Ala Arg Arg Ser Leu Glu Pro Asp Pro Ala
        115                 120                 125
Gln Thr Gly Pro Arg Pro Ala Arg Ala Ala Gly Met Ser Glu Ala Arg
130                 135                 140
Lys Gly Pro Asp Glu Ala Glu Ser Gln Tyr Asp Ser Gly Ile Glu
145                 150                 155                 160
Ser Leu Arg Ser Leu Arg Ser Leu Pro Glu Ser Thr Ser Ala Pro Ala
                165                 170                 175
Ser Gly Pro Ser Asp Gly Ser Pro Gln Pro Cys Thr His Pro Pro Gly
            180                 185                 190
Pro Val Lys Glu Pro Gln Glu Lys Glu Asp Ala Asp Gly Glu Arg Ala
        195                 200                 205
```

```
Asp Ser Thr Tyr Gly Ser Ser Ser Leu Thr Tyr Thr Leu Ser Leu Leu
    210                 215                 220

Gly Gly Pro Glu Ala Glu Asp Pro Ala Pro Arg Leu Pro Leu Pro His
225                 230                 235                 240

Val Gly Ala Leu Ser Pro Gln Gln Leu Glu Ala Leu Thr Tyr Ile Ser
                245                 250                 255

Glu Asp Gly Asp Thr Leu Val His Leu Ala Val Ile His Glu Ala Pro
                260                 265                 270

Ala Val Leu Leu Cys Cys Leu Ala Leu Leu Pro Gln Glu Val Leu Asp
                275                 280                 285

Ile Gln Asn Asn Leu Tyr Gln Thr Ala Leu His Leu Ala Val His Leu
    290                 295                 300

Asp Gln Pro Gly Ala Val Arg Ala Leu Val Leu Lys Gly Ala Ser Arg
305                 310                 315                 320

Ala Leu Gln Asp Arg His Gly Asp Thr Ala Leu His Val Ala Cys Gln
                325                 330                 335

Arg Gln His Leu Ala Cys Ala Arg Cys Leu Leu Glu Gly Arg Pro Glu
                340                 345                 350

Pro Gly Arg Gly Thr Ser His Ser Leu Asp Leu Gln Leu Gln Asn Trp
                355                 360                 365

Gln Gly Leu Ala Cys Leu His Ile Ala Thr Leu Gln Lys Asn Gln Pro
    370                 375                 380

Leu Met Glu Leu Leu Leu Arg Asn Gly Ala Asp Ile Asp Val Gln Glu
385                 390                 395                 400

Gly Thr Ser Gly Lys Thr Ala Leu His Leu Ala Val Glu Thr Gln Glu
                405                 410                 415

Arg Gly Leu Val Gln Phe Leu Leu Gln Ala Gly Ala Gln Val Asp Ala
                420                 425                 430

Arg Met Leu Asn Gly Cys Thr Pro Leu His Leu Ala Ala Gly Arg Gly
                435                 440                 445

Leu Met Gly Ile Ser Ser Thr Leu Cys Lys Ala Gly Ala Asp Ser Leu
    450                 455                 460

Leu Arg Asn Val Glu Asp Glu Thr Pro Gln Asp Leu Thr Glu Glu Ser
465                 470                 475                 480

Leu Val Leu Leu Pro Phe Asp Asp Leu Lys Ile Ser Gly Lys Leu Leu
                485                 490                 495

Leu Cys Thr Asp
                500

<210> SEQ ID NO 60
<211> LENGTH: 635
<212> TYPE: PRT
<213> ORGANISM: Homo Sapiens

<400> SEQUENCE: 60

Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
                20                  25                  30

Gly Met Ser Asp Gly Leu Tyr Leu Leu Arg Gln Ser Arg Asn Tyr Leu
            35                  40                  45

Gly Gly Phe Ala Leu Ser Val Ala His Gly Arg Lys Ala His His Tyr
        50                  55                  60

Thr Ile Glu Arg Glu Leu Asn Gly Thr Tyr Ala Ile Ala Gly Gly Arg
65              70                  75                  80
```

-continued

```
Thr His Ala Ser Pro Ala Asp Leu Cys His Tyr His Ser Gln Glu Ser
             85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
    210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Thr Trp Ser Ala Gly Gly
        275                 280                 285

Ile Ile Ser Arg Ile Lys Ser Tyr Ser Phe Pro Lys Pro Gly His Arg
    290                 295                 300

Lys Ser Ser Pro Ala Gln Gly Asn Arg Gln Glu Ser Thr Val Ser Phe
305                 310                 315                 320

Asn Pro Tyr Glu Pro Glu Leu Ala Pro Trp Ala Ala Asp Lys Gly Pro
                325                 330                 335

Gln Arg Glu Ala Leu Pro Met Asp Thr Glu Val Tyr Glu Ser Pro Tyr
            340                 345                 350

Ala Asp Pro Glu Glu Ile Arg Pro Lys Glu Val Tyr Leu Asp Arg Lys
        355                 360                 365

Leu Leu Thr Leu Glu Asp Lys Glu Leu Gly Ser Gly Asn Phe Gly Thr
    370                 375                 380

Val Lys Lys Gly Tyr Tyr Gln Met Lys Lys Val Val Lys Thr Val Ala
385                 390                 395                 400

Val Lys Ile Leu Lys Asn Glu Ala Asn Asp Pro Ala Leu Lys Asp Glu
                405                 410                 415

Leu Leu Ala Glu Ala Asn Val Met Gln Gln Leu Asp Asn Pro Tyr Ile
            420                 425                 430

Val Arg Met Ile Gly Ile Cys Glu Ala Glu Ser Trp Met Leu Val Met
        435                 440                 445

Glu Met Ala Glu Leu Gly Pro Leu Asn Lys Tyr Leu Gln Gln Asn Arg
    450                 455                 460

His Val Lys Asp Lys Asn Ile Ile Glu Leu Val His Gln Val Ser Met
465                 470                 475                 480

Gly Met Lys Tyr Leu Glu Glu Ser Asn Phe Val His Arg Asp Leu Ala
                485                 490                 495
```

```
Ala Arg Asn Val Leu Leu Val Thr Gln His Tyr Ala Lys Ile Ser Asp
            500                 505                 510

Phe Gly Leu Ser Lys Ala Leu Arg Ala Asp Glu Asn Tyr Tyr Lys Ala
            515                 520                 525

Gln Thr His Gly Lys Trp Pro Val Lys Trp Tyr Ala Pro Glu Cys Ile
            530                 535                 540

Asn Tyr Tyr Lys Phe Ser Ser Lys Ser Asp Val Trp Ser Phe Gly Val
545                 550                 555                 560

Leu Met Trp Glu Ala Phe Ser Tyr Gly Gln Lys Pro Tyr Arg Gly Met
                565                 570                 575

Lys Gly Ser Glu Val Thr Ala Met Leu Glu Lys Gly Glu Arg Met Gly
            580                 585                 590

Cys Pro Ala Gly Cys Pro Arg Glu Met Tyr Asp Leu Met Asn Leu Cys
            595                 600                 605

Trp Thr Tyr Asp Val Glu Asn Arg Pro Gly Phe Ala Ala Val Glu Leu
            610                 615                 620

Arg Leu Arg Asn Tyr Tyr Tyr Asp Val Val Asn
625                 630                 635

<210> SEQ ID NO 61
<211> LENGTH: 652
<212> TYPE: PRT
<213> ORGANISM: Homo Sapiens

<400> SEQUENCE: 61

Met Ala Glu Ala Pro Gln Val Val Glu Thr Asp Pro Asp Phe Glu Pro
1               5                   10                  15

Leu Pro Arg Gln Arg Ser Cys Thr Trp Pro Leu Pro Arg Pro Glu Phe
            20                  25                  30

Asn Gln Ser Asn Ser Thr Thr Ser Ser Pro Ala Pro Ser Gly Gly Ala
            35                  40                  45

Ala Ala Asn Pro Asp Ala Ala Ala Ser Leu Ala Ser Ala Ser Ala Val
        50                  55                  60

Ser Thr Asp Phe Met Ser Asn Leu Ser Leu Leu Glu Glu Ser Glu Asp
65                  70                  75                  80

Phe Ala Arg Ala Pro Gly Cys Val Ala Val Ala Ala Ala Ala Ala Ala
                85                  90                  95

Ser Arg Gly Leu Cys Gly Asp Phe Gln Gly Pro Glu Ala Gly Cys Val
            100                 105                 110

His Pro Ala Pro Pro Gln Pro Pro Thr Gly Pro Leu Ser Gln Pro
            115                 120                 125

Pro Pro Val Pro Pro Ser Ala Ala Ala Ala Gly Pro Leu Ala Gly
        130                 135                 140

Gln Pro Arg Lys Thr Ser Ser Ser Arg Arg Asn Ala Trp Gly Asn Leu
145                 150                 155                 160

Ser Tyr Ala Asp Leu Ile Thr Lys Ala Ile Glu Ser Ser Ala Glu Lys
                165                 170                 175

Arg Leu Thr Leu Ser Gln Ile Tyr Glu Trp Met Val Lys Ser Val Pro
            180                 185                 190

Tyr Phe Lys Asp Lys Gly Asp Ser Asn Ser Ser Ala Gly Trp Lys Asn
            195                 200                 205

Ser Ile Arg His Asn Leu Ser Leu His Ser Lys Phe Ile Arg Val Gln
        210                 215                 220

Asn Glu Gly Thr Gly Lys Ser Ser Trp Trp Met Leu Asn Pro Glu Gly
225                 230                 235                 240
```

-continued

```
Gly Lys Ser Gly Lys Ser Pro Arg Arg Ala Ala Ser Met Asp Asn
            245                 250                 255

Asn Ser Lys Phe Ala Lys Ser Arg Gly Arg Ala Ala Lys Lys Lys Ala
        260                 265                 270

Ser Leu Gln Ser Gly Gln Glu Gly Pro Gly Asp Ser Pro Gly Ser Gln
            275                 280                 285

Phe Ser Lys Trp Pro Ala Ser Pro Gly Ser His Ser Asn Asp Asp Phe
        290                 295                 300

Asp Asn Trp Ser Thr Phe Arg Pro Arg Thr Ser Ser Asn Ala Ser Thr
305                 310                 315                 320

Ile Ser Gly Arg Leu Ser Pro Ile Met Thr Glu Gln Asp Leu Gly
            325                 330                 335

Asp Gly Asp Val His Ser Leu Val Tyr Pro Ser Ala Ala Lys Met
            340                 345                 350

Ala Ser Thr Leu Pro Ser Leu Ser Glu Ile Ser Asn Pro Glu Asn Met
            355                 360                 365

Glu Asn Leu Leu Asp Asn Leu Asn Leu Ser Ser Pro Thr Ser Leu
        370                 375                 380

Thr Val Ser Thr Gln Ser Ser Pro Gly Ser Met Met Gln Gln Thr Pro
385                 390                 395                 400

Cys Tyr Ser Phe Ala Pro Pro Asn Thr Ser Leu Asn Ser Pro Ser Pro
                405                 410                 415

Asn Tyr Ser Lys Tyr Thr Tyr Gly Gln Ser Ser Met Ser Pro Leu Pro
                420                 425                 430

Gln Met Pro Met Gln Thr Leu Gln Asp Ser Lys Ser Ser Tyr Gly Gly
            435                 440                 445

Leu Asn Gln Tyr Asn Cys Ala Pro Gly Leu Leu Lys Glu Leu Leu Thr
        450                 455                 460

Ser Asp Ser Pro Pro His Asn Asp Ile Met Ser Pro Val Asp Pro Gly
465                 470                 475                 480

Val Ala Gln Pro Asn Ser Arg Val Leu Gly Gln Asn Val Met Met Gly
                485                 490                 495

Pro Asn Ser Val Met Pro Ala Tyr Gly Ser Gln Ala Ser His Asn Lys
            500                 505                 510

Met Met Asn Pro Ser Ser His Thr His Pro Gly His Ala Gln Gln Thr
        515                 520                 525

Ala Ser Val Asn Gly Arg Thr Leu Pro His Val Val Asn Thr Met Pro
        530                 535                 540

His Thr Ser Ala Met Asn Arg Leu Thr Pro Val Lys Thr Pro Leu Gln
545                 550                 555                 560

Val Pro Leu Ser His Pro Met Gln Met Ser Ala Leu Gly Ser Tyr Ser
                565                 570                 575

Ser Val Ser Ser Cys Asn Gly Tyr Gly Arg Met Gly Val Leu His Gln
            580                 585                 590

Glu Lys Leu Pro Ser Asp Leu Asp Gly Met Phe Ile Glu Arg Leu Asp
        595                 600                 605

Cys Asp Met Glu Ser Ile Ile Arg Asn Asp Leu Met Asp Gly Asp Thr
            610                 615                 620

Leu Asp Phe Asn Phe Asp Asn Val Leu Pro Asn Gln Ser Phe Pro His
625                 630                 635                 640

Ser Val Lys Thr Thr Thr His Ser Trp Val Ser Gly
            645                 650
```

<210> SEQ ID NO 62
<211> LENGTH: 226
<212> TYPE: PRT
<213> ORGANISM: Homo Sapiens

<400> SEQUENCE: 62

```
Met Pro Gly Gly Pro Gly Val Leu Gln Ala Leu Pro Ala Thr Ile Phe
1               5                   10                  15
Leu Leu Phe Leu Leu Ser Ala Val Tyr Leu Gly Pro Gly Cys Gln Ala
                20                  25                  30
Leu Trp Met His Lys Val Pro Ala Ser Leu Met Val Ser Leu Gly Glu
            35                  40                  45
Asp Ala His Phe Gln Cys Pro His Asn Ser Ser Asn Ala Asn Val
        50                  55                  60
Thr Trp Trp Arg Val Leu His Gly Asn Tyr Thr Trp Pro Pro Glu Phe
65                  70                  75                  80
Leu Gly Pro Gly Glu Asp Pro Asn Gly Thr Leu Ile Ile Gln Asn Val
                85                  90                  95
Asn Lys Ser His Gly Gly Ile Tyr Val Cys Arg Val Gln Glu Gly Asn
                100                 105                 110
Glu Ser Tyr Gln Gln Ser Cys Gly Thr Tyr Leu Arg Val Arg Gln Pro
            115                 120                 125
Pro Pro Arg Pro Phe Leu Asp Met Gly Glu Gly Thr Lys Asn Arg Ile
        130                 135                 140
Ile Thr Ala Glu Gly Ile Ile Leu Leu Phe Cys Ala Val Val Pro Gly
145                 150                 155                 160
Thr Leu Leu Leu Phe Arg Lys Arg Trp Gln Asn Glu Lys Leu Gly Leu
                165                 170                 175
Asp Ala Gly Asp Glu Tyr Glu Asp Glu Asn Leu Tyr Glu Gly Leu Asn
                180                 185                 190
Leu Asp Asp Cys Ser Met Tyr Glu Asp Ile Ser Arg Gly Leu Gln Gly
            195                 200                 205
Thr Tyr Gln Asp Val Gly Ser Leu Asn Ile Gly Asp Val Gln Leu Glu
        210                 215                 220
Lys Pro
225
```

<210> SEQ ID NO 63
<211> LENGTH: 390
<212> TYPE: PRT
<213> ORGANISM: Homo Sapiens

<400> SEQUENCE: 63

```
Met Gly Ala Thr Thr Met Asp Gln Lys Ser Leu Trp Ala Gly Val Val
1               5                   10                  15
Val Leu Leu Leu Leu Gln Gly Gly Ser Ala Tyr Lys Leu Val Cys Tyr
                20                  25                  30
Phe Thr Asn Trp Ser Gln Asp Arg Gln Glu Pro Gly Lys Phe Thr Pro
            35                  40                  45
Glu Asn Ile Asp Pro Phe Leu Cys Ser His Leu Ile Tyr Ser Phe Ala
        50                  55                  60
Ser Ile Glu Asn Asn Lys Val Ile Ile Lys Asp Lys Ser Glu Val Met
65                  70                  75                  80
Leu Tyr Gln Thr Ile Asn Ser Leu Lys Thr Lys Asn Pro Lys Leu Lys
                85                  90                  95
```

Ile Leu Leu Ser Ile Gly Gly Tyr Leu Phe Gly Ser Lys Gly Phe His
            100                 105                 110

Pro Met Val Asp Ser Ser Thr Ser Arg Leu Glu Phe Ile Asn Ser Ile
        115                 120                 125

Ile Leu Phe Leu Arg Asn His Asn Phe Asp Gly Leu Asp Val Ser Trp
    130                 135                 140

Ile Tyr Pro Asp Gln Lys Glu Asn Thr His Phe Thr Val Leu Ile His
145                 150                 155                 160

Glu Leu Ala Glu Ala Phe Gln Lys Asp Phe Thr Lys Ser Thr Lys Glu
                165                 170                 175

Arg Leu Leu Leu Thr Ala Gly Val Ser Ala Gly Arg Gln Met Ile Asp
            180                 185                 190

Asn Ser Tyr Gln Val Glu Lys Leu Ala Lys Asp Leu Asp Phe Ile Asn
        195                 200                 205

Leu Leu Ser Phe Asp Phe His Gly Ser Trp Glu Lys Pro Leu Ile Thr
    210                 215                 220

Gly His Asn Ser Pro Leu Ser Lys Gly Trp Gln Asp Arg Gly Pro Ser
225                 230                 235                 240

Ser Tyr Tyr Asn Val Glu Tyr Ala Val Gly Tyr Trp Ile His Lys Gly
                245                 250                 255

Met Pro Ser Glu Lys Val Val Met Gly Ile Pro Thr Tyr Gly His Ser
            260                 265                 270

Phe Thr Leu Ala Ser Ala Glu Thr Thr Val Gly Ala Pro Ala Ser Gly
        275                 280                 285

Pro Gly Ala Ala Gly Pro Ile Thr Glu Ser Ser Gly Phe Leu Ala Tyr
    290                 295                 300

Tyr Glu Ile Cys Gln Phe Leu Lys Gly Ala Lys Ile Thr Arg Leu Gln
305                 310                 315                 320

Asp Gln Gln Val Pro Tyr Ala Val Lys Gly Asn Gln Trp Val Gly Tyr
                325                 330                 335

Asp Asp Val Lys Ser Met Glu Thr Lys Val Gln Phe Leu Lys Asn Leu
            340                 345                 350

Asn Leu Gly Gly Ala Met Ile Trp Ser Ile Asp Met Asp Asp Phe Thr
        355                 360                 365

Gly Lys Ser Cys Asn Gln Gly Pro Tyr Pro Leu Val Gln Ala Val Lys
    370                 375                 380

Arg Ser Leu Gly Ser Leu
385                 390

<210> SEQ ID NO 64
<211> LENGTH: 589
<212> TYPE: PRT
<213> ORGANISM: Homo Sapiens

<400> SEQUENCE: 64

Met Ser Gln Arg Val Arg Arg Asn Gly Ser Pro Thr Pro Ala Gly Ser
1               5                   10                  15

Leu Gly Gly Gly Ala Val Ala Thr Ala Gly Gly Pro Gly Ser Arg Leu
            20                  25                  30

Gln Pro Met Arg Ala Thr Val Pro Phe Gln Leu Lys Gln Gln Gln Gln
        35                  40                  45

Gln Gln His Gly Ser Pro Thr Arg Ser Gly Gly Gly Gly Gly Gly Asn
    50                  55                  60

Asn Asn Gly Gly Cys Cys Gly Gly Ala Ser Gly Pro Ala Gly Gly Gly
65                  70                  75                  80

-continued

Gly Gly Gly Gly Pro Arg Thr Ala Ser Arg Ser Thr Ser Pro Thr Arg
                85                  90                  95

Gly Gly Gly Asn Ala Ala Arg Thr Ser Pro Thr Val Ala Thr Gln
            100                 105                 110

Thr Gly Ala Ser Ala Thr Ser Thr Arg Gly Thr Ser Pro Thr Arg Ser
            115                 120                 125

Ala Ala Pro Gly Ala Arg Gly Ser Pro Pro Arg Pro Pro Pro Pro
130                 135                 140

Pro Leu Leu Gly Thr Val Ser Ser Pro Ser Ser Ser Pro Thr His Leu
145                 150                 155                 160

Trp Thr Gly Glu Val Ser Ala Ala Pro Pro Ala Arg Val Arg His
                165                 170                 175

Arg Arg Arg Ser Pro Glu Gln Ser Arg Ser Ser Pro Glu Lys Arg Ser
                180                 185                 190

Pro Ser Ala Pro Val Cys Lys Ala Gly Asp Lys Thr Arg Gln Pro Ser
            195                 200                 205

Ser Ser Pro Ser Ser Ile Ile Arg Arg Thr Ser Ser Leu Asp Thr Leu
    210                 215                 220

Ala Ala Pro Tyr Leu Ala Gly His Trp Pro Arg Asp Ser His Gly Gln
225                 230                 235                 240

Ala Ala Pro Cys Met Arg Asp Lys Ala Thr Gln Thr Glu Ser Ala Trp
                245                 250                 255

Ala Glu Glu Tyr Ser Glu Lys Lys Lys Gly Ser His Lys Arg Ser Ala
                260                 265                 270

Ser Trp Gly Ser Thr Asp Gln Leu Lys Glu Ile Ala Lys Leu Arg Gln
            275                 280                 285

Gln Leu Gln Arg Ser Lys His Ser Ser Arg His His Arg Asp Lys Glu
    290                 295                 300

Arg Gln Ser Pro Phe His Gly Asn His Ala Ala Ile Asn Gln Cys Gln
305                 310                 315                 320

Ala Pro Val Pro Lys Ser Ala Leu Ile Pro Val Pro Ile Thr Lys
                325                 330                 335

Ser Thr Gly Ser Arg Phe Arg Asn Ser Val Glu Gly Leu Asn Gln Glu
            340                 345                 350

Ile Glu Ile Ile Ile Lys Glu Thr Gly Glu Lys Glu Gln Leu Ile
    355                 360                 365

Pro Gln Asp Ile Pro Asp Gly His Arg Ala Pro Pro Leu Val Gln
370                 375                 380

Arg Ser Ser Thr Arg Ser Ile Asp Thr Gln Thr Pro Gly Gly Ala
385                 390                 395                 400

Asp Arg Gly Ser Asn Asn Ser Ser Arg Ser Gln Ser Val Ser Pro Thr
                405                 410                 415

Ser Phe Leu Thr Ile Ser Asn Glu Gly Ser Glu Glu Ser Pro Cys Ser
            420                 425                 430

Ala Asp Asp Leu Leu Val Asp Pro Arg Asp Lys Glu Asn Gly Asn Asn
            435                 440                 445

Ser Pro Leu Pro Lys Tyr Ala Thr Ser Pro Lys Pro Asn Asn Ser Tyr
    450                 455                 460

Met Phe Lys Arg Glu Pro Pro Glu Gly Cys Glu Arg Val Lys Val Phe
465                 470                 475                 480

Glu Glu Cys Ser Pro Lys Gln Leu His Glu Ile Pro Ala Phe Tyr Cys
                485                 490                 495

Pro Asp Lys Asn Lys Val Asn Phe Ile Pro Lys Ser Gly Ser Ala Phe
            500                 505                 510

Cys Leu Val Ser Ile Leu Lys Pro Leu Leu Pro Thr Pro Asp Leu Thr
        515                 520                 525

Leu Lys Gly Ser Gly His Ser Leu Thr Val Thr Thr Gly Met Thr Thr
    530                 535                 540

Thr Leu Leu Gln Pro Ile Ala Val Ala Ser Leu Ser Thr Asn Thr Glu
545                 550                 555                 560

Gln Asp Arg Val Ser Arg Gly Thr Ser Thr Val Met Pro Ser Ala Ser
                565                 570                 575

Leu Leu Pro Pro Pro Glu Pro Ile Glu Glu Ala Glu Gly
            580                 585

<210> SEQ ID NO 65
<211> LENGTH: 372
<212> TYPE: PRT
<213> ORGANISM: Homo Sapiens

<400> SEQUENCE: 65

Met Leu Ala Asn Ser Ser Ser Thr Asn Ser Ser Val Leu Pro Cys Pro
1               5                   10                  15

Asp Tyr Arg Pro Thr His Arg Leu His Leu Val Val Tyr Ser Leu Val
            20                  25                  30

Leu Ala Ala Gly Leu Pro Leu Asn Ala Leu Ala Leu Trp Val Phe Leu
        35                  40                  45

Arg Ala Leu Arg Val His Ser Val Val Ser Val Tyr Met Cys Asn Leu
    50                  55                  60

Ala Ala Ser Asp Leu Leu Phe Thr Leu Ser Leu Pro Val Arg Leu Ser
65                  70                  75                  80

Tyr Tyr Ala Leu His His Trp Pro Phe Pro Asp Leu Leu Cys Gln Thr
                85                  90                  95

Thr Gly Ala Ile Phe Gln Met Asn Met Tyr Gly Ser Cys Ile Phe Leu
            100                 105                 110

Met Leu Ile Asn Val Asp Arg Tyr Ala Ala Ile Val His Pro Leu Arg
        115                 120                 125

Leu Arg His Leu Arg Arg Pro Arg Val Ala Arg Leu Leu Cys Leu Gly
    130                 135                 140

Val Trp Ala Leu Ile Leu Val Phe Ala Val Pro Ala Ala Arg Val His
145                 150                 155                 160

Arg Pro Ser Arg Cys Arg Tyr Arg Asp Leu Glu Val Arg Leu Cys Phe
                165                 170                 175

Glu Ser Phe Ser Asp Glu Leu Trp Lys Gly Arg Leu Leu Pro Leu Val
            180                 185                 190

Leu Leu Ala Glu Ala Leu Gly Phe Leu Leu Pro Leu Ala Val Val Val
        195                 200                 205

Tyr Ser Ser Gly Arg Val Phe Trp Thr Leu Ala Arg Pro Asp Ala Thr
    210                 215                 220

Gln Ser Gln Arg Arg Arg Lys Thr Val Arg Leu Leu Ala Asn Leu
225                 230                 235                 240

Val Ile Phe Leu Leu Cys Phe Val Pro Tyr Asn Ser Thr Leu Ala Val
                245                 250                 255

Tyr Gly Leu Leu Arg Ser Lys Leu Val Ala Ala Ser Val Pro Ala Arg
            260                 265                 270

Asp Arg Val Arg Gly Val Leu Met Val Met Val Leu Leu Ala Gly Ala
        275                 280                 285

```
Asn Cys Val Leu Asp Pro Leu Val Tyr Tyr Phe Ser Ala Glu Gly Phe
        290                 295                 300

Arg Asn Thr Leu Arg Gly Leu Gly Thr Pro His Arg Ala Arg Thr Ser
305                 310                 315                 320

Ala Thr Asn Gly Thr Arg Ala Ala Leu Ala Gln Ser Glu Arg Ser Ala
                325                 330                 335

Val Thr Thr Asp Ala Thr Arg Pro Asp Ala Ala Ser Gln Gly Leu Leu
                340                 345                 350

Arg Pro Ser Asp Ser His Ser Leu Ser Ser Phe Thr Gln Cys Pro Gln
            355                 360                 365

Asp Ser Ala Leu
        370

<210> SEQ ID NO 66
<211> LENGTH: 943
<212> TYPE: PRT
<213> ORGANISM: Homo Sapiens

<400> SEQUENCE: 66

Met Pro Ser Thr Ser Phe Pro Val Pro Ser Lys Phe Pro Leu Gly Pro
1               5                   10                  15

Ala Ala Ala Val Phe Gly Arg Gly Glu Thr Leu Gly Pro Ala Pro Arg
                20                  25                  30

Ala Gly Gly Thr Met Lys Ser Ala Glu Glu His Tyr Gly Tyr Ala
            35                  40                  45

Ser Ser Asn Val Ser Pro Ala Leu Pro Leu Pro Thr Ala His Ser Thr
50                  55                  60

Leu Pro Ala Pro Cys His Asn Leu Gln Thr Ser Thr Pro Gly Ile Ile
65                  70                  75                  80

Pro Pro Ala Asp His Pro Ser Gly Tyr Gly Ala Ala Leu Asp Gly Gly
                85                  90                  95

Pro Ala Gly Tyr Phe Leu Ser Ser Gly His Thr Arg Pro Asp Gly Ala
            100                 105                 110

Pro Ala Leu Glu Ser Pro Arg Ile Glu Ile Thr Ser Cys Leu Gly Leu
        115                 120                 125

Tyr His Asn Asn Asn Gln Phe Phe His Asp Val Glu Val Glu Asp Val
130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Ser Pro Gln Thr Ser Pro Trp Gln Ser Pro
        195                 200                 205

Cys Val Ser Pro Lys Thr Thr Asp Pro Glu Glu Gly Phe Pro Arg Gly
    210                 215                 220

Leu Gly Ala Cys Thr Leu Leu Gly Ser Pro Arg His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
```

```
            275                 280                 285
Gly Ser Pro Arg Val Ser Val Thr Asp Asp Ser Trp Leu Gly Asn Thr
290                 295                 300
Thr Gln Tyr Thr Ser Ser Ala Ile Val Ala Ile Asn Ala Leu Thr
305                 310                 315                 320
Thr Asp Ser Ser Leu Asp Leu Gly Asp Gly Val Pro Val Lys Ser Arg
                325                 330                 335
Lys Thr Thr Leu Glu Gln Pro Pro Ser Val Ala Leu Lys Val Glu Pro
                340                 345                 350
Val Gly Glu Asp Leu Gly Ser Pro Pro Pro Ala Asp Phe Ala Pro
            355                 360                 365
Glu Asp Tyr Ser Ser Phe Gln His Ile Arg Lys Gly Phe Cys Asp
            370                 375                 380
Gln Tyr Leu Ala Val Pro Gln His Pro Tyr Gln Trp Ala Lys Pro Lys
385                 390                 395                 400
Pro Leu Ser Pro Thr Ser Tyr Met Ser Pro Thr Leu Pro Ala Leu Asp
                405                 410                 415
Trp Gln Leu Pro Ser His Ser Gly Pro Tyr Glu Leu Arg Ile Glu Val
                420                 425                 430
Gln Pro Lys Ser His His Arg Ala His Tyr Glu Thr Glu Gly Ser Arg
            435                 440                 445
Gly Ala Val Lys Ala Ser Ala Gly Gly His Pro Ile Val Gln Leu His
450                 455                 460
Gly Tyr Leu Glu Asn Glu Pro Leu Met Leu Gln Leu Phe Ile Gly Thr
465                 470                 475                 480
Ala Asp Asp Arg Leu Leu Arg Pro His Ala Phe Tyr Gln Val His Arg
                485                 490                 495
Ile Thr Gly Lys Thr Val Ser Thr Thr Ser His Glu Ala Ile Leu Ser
            500                 505                 510
Asn Thr Lys Val Leu Glu Ile Pro Leu Leu Pro Glu Asn Ser Met Arg
            515                 520                 525
Ala Val Ile Asp Cys Ala Gly Ile Leu Lys Leu Arg Asn Ser Asp Ile
530                 535                 540
Glu Leu Arg Lys Gly Glu Thr Asp Ile Gly Arg Lys Asn Thr Arg Val
545                 550                 555                 560
Arg Leu Val Phe Arg Val His Val Pro Gln Pro Ser Gly Arg Thr Leu
                565                 570                 575
Ser Leu Gln Val Ala Ser Asn Pro Ile Glu Cys Ser Gln Arg Ser Ala
            580                 585                 590
Gln Glu Leu Pro Leu Val Glu Lys Gln Ser Thr Asp Ser Tyr Pro Val
            595                 600                 605
Val Gly Gly Lys Lys Met Val Leu Ser Gly His Asn Phe Leu Gln Asp
            610                 615                 620
Ser Lys Val Ile Phe Val Glu Lys Ala Pro Asp Gly His His Val Trp
625                 630                 635                 640
Glu Met Glu Ala Lys Thr Asp Arg Asp Leu Cys Lys Pro Asn Ser Leu
                645                 650                 655
Val Val Glu Ile Pro Pro Phe Arg Asn Gln Arg Ile Thr Ser Pro Val
                660                 665                 670
His Val Ser Phe Tyr Val Cys Asn Gly Lys Arg Lys Arg Ser Gln Tyr
            675                 680                 685
Gln Arg Phe Thr Tyr Leu Pro Ala Asn Val Pro Ile Ile Lys Thr Glu
            690                 695                 700
```

```
Pro Thr Asp Asp Tyr Glu Pro Ala Pro Thr Cys Gly Pro Val Ser Gln
705                 710                 715                 720

Gly Leu Ser Pro Leu Pro Arg Pro Tyr Tyr Ser Gln Gln Leu Ala Met
            725                 730                 735

Pro Pro Asp Pro Ser Ser Cys Leu Val Ala Gly Phe Pro Pro Cys Pro
        740                 745                 750

Gln Arg Ser Thr Leu Met Pro Ala Ala Pro Gly Val Ser Pro Lys Leu
            755                 760                 765

His Asp Leu Ser Pro Ala Ala Tyr Thr Lys Gly Val Ala Ser Pro Gly
        770                 775                 780

His Cys His Leu Gly Leu Pro Gln Pro Ala Glu Ala Pro Ala Val
785                 790                 795                 800

Gln Asp Val Pro Arg Pro Val Ala Thr His Pro Gly Ser Pro Gly Gln
                805                 810                 815

Pro Pro Pro Ala Leu Leu Pro Gln Gln Val Ser Ala Pro Pro Ser Ser
            820                 825                 830

Ser Cys Pro Pro Gly Leu Glu His Ser Leu Cys Pro Ser Ser Pro Ser
835                 840                 845

Pro Pro Leu Pro Ala Thr Gln Glu Pro Thr Cys Leu Gln Pro Cys
    850                 855                 860

Ser Pro Ala Cys Pro Pro Ala Thr Gly Arg Pro Gln His Leu Pro Ser
865                 870                 875                 880

Thr Val Arg Arg Asp Glu Ser Pro Thr Ala Gly Pro Arg Leu Leu Pro
                885                 890                 895

Glu Val His Glu Asp Gly Ser Pro Asn Leu Ala Pro Ile Pro Val Thr
                900                 905                 910

Val Lys Arg Glu Pro Glu Glu Leu Asp Gln Leu Tyr Leu Asp Asp Val
            915                 920                 925

Asn Glu Ile Ile Arg Asn Asp Leu Ser Ser Thr Ser Thr His Ser
    930                 935                 940

<210> SEQ ID NO 67

<400> SEQUENCE: 67

000

<210> SEQ ID NO 68
<211> LENGTH: 239
<212> TYPE: PRT
<213> ORGANISM: Homo Sapiens

<400> SEQUENCE: 68

Met Leu Leu Gln Pro Ala Pro Cys Ala Pro Ser Ala Gly Phe Pro Arg
1               5                   10                  15

Pro Leu Ala Ala Pro Gly Ala Met His Gly Ser Gln Lys Asp Thr Thr
            20                  25                  30

Phe Thr Lys Ile Phe Val Gly Gly Leu Pro Tyr His Thr Thr Asp Ala
        35                  40                  45

Ser Leu Arg Lys Tyr Phe Glu Gly Phe Gly Asp Ile Glu Glu Ala Val
    50                  55                  60

Val Ile Thr Asp Arg Gln Thr Gly Lys Ser Arg Gly Tyr Gly Phe Val
65                  70                  75                  80

Thr Met Ala Asp Arg Ala Ala Ala Glu Arg Ala Cys Lys Asp Pro Asn
                85                  90                  95
```

```
Pro Ile Ile Asp Gly Arg Lys Ala Asn Val Asn Leu Ala Tyr Leu Gly
            100                 105                 110

Ala Lys Pro Arg Ser Leu Gln Thr Gly Phe Ala Ile Gly Val Gln Gln
        115                 120                 125

Leu His Pro Thr Leu Ile Gln Arg Thr Tyr Gly Leu Thr Pro His Tyr
    130                 135                 140

Ile Tyr Pro Pro Ala Ile Val Gln Pro Ser Val Val Ile Pro Ala Ala
145                 150                 155                 160

Pro Val Pro Ser Leu Ser Ser Pro Tyr Ile Glu Tyr Thr Pro Ala Ser
                165                 170                 175

Pro Ala Tyr Ala Gln Tyr Pro Pro Ala Thr Tyr Asp Gln Tyr Pro Tyr
            180                 185                 190

Ala Ala Ser Pro Ala Thr Ala Ala Ser Phe Val Gly Tyr Ser Tyr Pro
        195                 200                 205

Ala Ala Val Pro Gln Ala Leu Ser Ala Ala Ala Pro Ala Gly Thr Thr
210                 215                 220

Phe Val Gln Tyr Gln Ala Pro Gln Leu Gln Pro Asp Arg Met Gln
225                 230                 235
```

<210> SEQ ID NO 69
<211> LENGTH: 441
<212> TYPE: PRT
<213> ORGANISM: Homo Sapiens

<400> SEQUENCE: 69

```
Met Ser Leu Arg Gln Arg Leu Ala Gln Leu Val Gly Arg Leu Gln Asp
1               5                   10                  15

Pro Gln Lys Val Ala Arg Phe Gln Arg Leu Cys Gly Val Glu Ala Pro
            20                  25                  30

Pro Arg Arg Ser Ala Asp Arg Arg Glu Asp Glu Lys Ala Glu Ala Pro
        35                  40                  45

Leu Ala Gly Asp Pro Arg Leu Arg Gly Arg Gln Pro Gly Ala Pro Gly
    50                  55                  60

Gly Pro Gln Pro Pro Gly Ser Asp Arg Asn Gln Cys Pro Ala Lys Pro
65                  70                  75                  80

Asp Gly Gly Gly Ala Pro Asn Gly Val Arg Asn Gly Leu Ala Ala Glu
                85                  90                  95

Leu Gly Pro Ala Ser Pro Arg Arg Ala Gly Ala Leu Arg Arg Asn Ser
            100                 105                 110

Leu Thr Gly Glu Glu Gly Gln Leu Ala Arg Val Ser Asn Trp Pro Leu
        115                 120                 125

Tyr Cys Leu Phe Cys Phe Gly Thr Glu Leu Gly Asn Glu Leu Phe Tyr
    130                 135                 140

Ile Leu Phe Phe Pro Phe Trp Ile Trp Asn Leu Asp Pro Leu Val Gly
145                 150                 155                 160

Arg Arg Leu Val Val Ile Trp Val Leu Val Met Tyr Leu Gly Gln Cys
                165                 170                 175

Thr Lys Asp Ile Ile Arg Trp Pro Arg Pro Ala Ser Pro Pro Val Val
            180                 185                 190

Lys Leu Glu Val Phe Tyr Asn Ser Glu Tyr Ser Met Pro Ser Thr His
        195                 200                 205

Ala Met Ser Gly Thr Ala Ile Pro Ile Ser Met Val Leu Leu Thr Tyr
    210                 215                 220

Gly Arg Trp Gln Tyr Pro Leu Ile Tyr Gly Leu Ile Leu Ile Pro Cys
225                 230                 235                 240
```

```
Trp Cys Ser Leu Val Cys Leu Ser Arg Ile Tyr Met Gly Met His Ser
            245                 250                 255

Ile Leu Asp Ile Ile Ala Gly Phe Leu Tyr Thr Ile Leu Ile Leu Ala
            260                 265                 270

Val Phe Tyr Pro Phe Val Asp Leu Ile Asp Asn Phe Asn Gln Thr His
            275                 280                 285

Lys Tyr Ala Pro Phe Ile Ile Ile Gly Leu His Leu Ala Leu Gly Ile
            290                 295                 300

Phe Ser Phe Thr Leu Asp Thr Trp Ser Thr Ser Arg Gly Asp Thr Ala
305                 310                 315                 320

Glu Ile Leu Gly Ser Gly Ala Gly Ile Ala Cys Gly Ser His Val Thr
            325                 330                 335

Tyr Asn Met Gly Leu Val Leu Asp Pro Ser Leu Asp Thr Leu Pro Leu
            340                 345                 350

Ala Gly Pro Pro Ile Thr Val Thr Leu Phe Gly Lys Ala Ile Leu Arg
            355                 360                 365

Ile Leu Ile Gly Met Val Phe Val Leu Ile Ile Arg Asp Val Met Lys
            370                 375                 380

Lys Ile Thr Ile Pro Leu Ala Cys Lys Ile Phe Asn Ile Pro Cys Asp
385                 390                 395                 400

Asp Ile Arg Lys Ala Arg Gln His Met Glu Val Glu Leu Pro Tyr Arg
            405                 410                 415

Tyr Ile Thr Tyr Gly Met Val Gly Phe Ser Ile Thr Phe Phe Val Pro
            420                 425                 430

Tyr Ile Phe Phe Phe Ile Gly Ile Ser
            435                 440

<210> SEQ ID NO 70
<211> LENGTH: 736
<212> TYPE: PRT
<213> ORGANISM: Homo Sapiens

<400> SEQUENCE: 70

Met Lys Thr Glu Ala Gln Pro Ser Thr Ser Leu Leu Ala Asn Thr Ser
1               5                   10                  15

Trp Thr Gly Thr Val Ile Ser Asp Ser Val Pro Gly Ser Gln Thr Trp
            20                  25                  30

Glu Asp Lys Gly Ser Leu Thr Arg Ser Ala Thr Ser Trp Thr Ser Glu
            35                  40                  45

Ala Gln Val Ser Ala Ala Arg Val Ala Glu Ala Gln Ala Arg Thr Ser
50                  55                  60

Gln Pro Lys Gln Ile Ser Val Leu Glu Ala Leu Thr Ala Ser Ala Leu
65                  70                  75                  80

Asn Gln Lys Pro Thr His Glu Lys Val Gln Met Thr Glu Lys Lys Glu
            85                  90                  95

Ser Glu Val Leu Leu Ala Arg Pro Phe Trp Ser Ser Lys Thr Glu Tyr
            100                 105                 110

Ile Leu Ala Gln Val Gly Phe Ser Met Lys Pro Ser Cys Leu Trp Arg
            115                 120                 125

Phe Ala Tyr Leu Trp Leu Asn Ser Gly Gly Cys Ser Phe Ala Ala Ile
            130                 135                 140

Tyr Ile Phe Met Leu Phe Leu Val Gly Val Pro Leu Leu Phe Leu Glu
145                 150                 155                 160

Met Ala Ala Gly Gln Ser Met Arg Gln Gly Gly Met Gly Val Trp Lys
```

```
                    165                 170                 175
Ile Ile Ala Pro Trp Ile Gly Val Gly Tyr Ser Ser Phe Met Val
                180                 185                 190

Cys Phe Ile Leu Gly Leu Tyr Phe Asn Val Val Asn Ser Trp Ile Ile
                195                 200                 205

Phe Tyr Met Ser Gln Ser Gln Phe Pro Val Pro Trp Glu Lys Cys
    210                 215                 220

Pro Leu Thr Met Asn Ser Ser Gly Phe Asp Pro Glu Cys Glu Arg Thr
225                 230                 235                 240

Thr Pro Ser Ile Tyr Phe Trp Tyr Gln Gln Ala Leu Lys Ala Ser Asp
                245                 250                 255

Arg Ile Glu Asp Gly Gly Ser Pro Val Tyr Ser Leu Val Leu Pro Phe
                260                 265                 270

Phe Leu Cys Trp Cys Leu Val Gly Ala Phe Met Ile Asn Gly Leu Lys
                275                 280                 285

Ser Thr Gly Lys Val Ile Tyr Val Leu Val Leu Leu Pro Cys Phe Ile
                290                 295                 300

Ile Val Gly Phe Phe Ile Arg Thr Leu Leu Leu Glu Gly Ala Lys Phe
305                 310                 315                 320

Gly Leu Gln Gln Leu Val Val Ala Lys Ile Ser Asp Val Tyr Asn Met
                325                 330                 335

Ser Val Trp Ser Leu Ala Gly Gly Gln Val Leu Ser Asn Thr Gly Ile
                340                 345                 350

Gly Leu Gly Ser Val Ala Ser Leu Ala Ser Tyr Met Pro Gln Ser Asn
                355                 360                 365

Asn Cys Leu Ser Asp Ala Phe Leu Val Ser Val Ile Asn Leu Leu Thr
                370                 375                 380

Leu Leu Val Phe Thr Ser Phe Asn Phe Cys Val Leu Gly Phe Trp Ala
385                 390                 395                 400

Thr Val Ile Thr His Arg Cys Cys Glu Arg Asn Ala Glu Ile Leu Leu
                405                 410                 415

Lys Leu Ile Asn Leu Gly Lys Leu Pro Pro Asp Ala Lys Pro Pro Val
                420                 425                 430

Asn Leu Leu Tyr Asn Pro Thr Ser Ile Tyr Asn Ala Trp Leu Ser Gly
                435                 440                 445

Leu Pro Gln His Ile Lys Ser Met Val Leu Arg Glu Val Thr Glu Cys
                450                 455                 460

Asn Ile Glu Thr Gln Phe Leu Lys Ala Ser Glu Gly Pro Lys Phe Ala
465                 470                 475                 480

Phe Leu Ser Phe Val Glu Ala Met Ser Phe Leu Pro Pro Ser Val Phe
                485                 490                 495

Trp Ser Phe Ile Phe Phe Leu Met Leu Leu Ala Met Gly Leu Ser Ser
                500                 505                 510

Ala Ile Gly Ile Met Gln Gly Ile Ile Thr Pro Leu Gln Asp Thr Phe
                515                 520                 525

Ser Phe Phe Arg Lys His Thr Lys Leu Leu Ile Val Gly Val Phe Leu
                530                 535                 540

Leu Met Phe Val Cys Gly Leu Phe Phe Thr Arg Pro Ser Gly Ser Tyr
545                 550                 555                 560

Phe Ile Arg Leu Leu Ser Asp Tyr Trp Ile Val Phe Pro Ile Ile Val
                565                 570                 575

Val Val Val Phe Glu Thr Met Ala Val Ser Trp Ala Tyr Gly Ala Arg
                580                 585                 590
```

-continued

```
Arg Phe Leu Ala Asp Leu Thr Ile Leu Leu Gly His Pro Ile Ser Pro
        595                 600             605

Ile Phe Gly Trp Leu Trp Pro His Leu Cys Pro Val Val Leu Leu Ile
        610             615             620

Ile Phe Val Thr Met Met Val His Leu Cys Met Lys Pro Ile Thr Tyr
625             630             635                     640

Met Ser Trp Asp Ser Ser Thr Ser Lys Glu Val Leu Arg Pro Tyr Pro
                645             650                 655

Pro Trp Ala Leu Leu Leu Met Ile Thr Leu Phe Ala Ile Val Ile Leu
            660             665             670

Pro Ile Pro Ala Tyr Phe Val Tyr Cys Arg Ile His Arg Ile Pro Phe
        675             680             685

Arg Pro Lys Ser Gly Asp Gly Pro Met Thr Ala Ser Thr Ser Leu Pro
        690             695             700

Leu Ser His Gln Leu Thr Pro Ser Lys Glu Val Gln Lys Glu Glu Ile
705             710             715                     720

Leu Gln Val Asp Glu Thr Lys Tyr Pro Ser Thr Cys Asn Val Thr Ser
                725             730             735
```

METHODS FOR IMPROVING ANTI-CD37 IMMUNOCONJUGATE THERAPY

CROSS REFERENCE TO RELATED APPLICATIONS

This application is a national phase entry of International Application No. PCT/IB2017/056841, filed Nov. 2, 2017, which claims the priority benefit of U.S. Provisional Application No. 62/416,376, filed Nov. 2, 2016, each of which is hereby incorporated by reference herein in its entirety.

REFERNCE TO A SEQUENCE LISTING SUBMITTED ELECTRONICALLY VIA EFS-WEB

The content of the electronically submitted sequence listing (Name: 4018_0050001_SeqListing_ST25.txt; Size: 241,183 bytes; and Date of Creation: Apr. 30, 2019) is herein incorporated by reference in its entirety.

FIELD OF THE INVENTION

The field of the invention generally relates to identifying and treating patients who are likely to respond to treatment with an anti-CD37 immunoconjugate (e.g., IMGN529).

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime.

IMGN529 (naratuximab emtansine) is an immunoconjugate containing an anti-CD37 antibody with direct anti-tumor activity conjugated via a thio-ether based linker to the cytotoxic anti-microtubule agent maytansinoid DM1. IMGN529 has shown clinical activity in lymphomas.

However, there is a need for means to determine which patients are likely to respond to treatment with such an anti-CD37 immunoconjugate and for incorporating such determinations into effective treatment regimens for patients. Measuring expression levels of biomarkers can be an effective means to identify patients and patient populations that are likely to respond to therapies, but it is unknown what defines patients who are likely to respond to anti-CD37 immunoconjugates.

It is clear that there is a need for methods to identify and treat patients that are more likely to benefit from CD37-targeting therapies.

BRIEF SUMMARY OF THE INVENTION

Methods of identifying patients who are likely to respond to anti-CD37 immunoconjugate therapy (e.g., IMGN529), and of improving the efficacy of anti-CD37 immunoconjugate therapy (e.g., IMGN529) are provided herein.

In one instance, a method for treating a patient having cancer, or a method of improving the efficacy of cancer therapy, comprises administering an anti-CD37 immunoconjugate (e.g., IMGN529) to the patient wherein an increased expression level has been detected in a cancer sample obtained from the patient for at least one gene selected from the group consisting of: SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP1.

In one instance, a method for treating a patient having cancer, or a method of improving the efficacy of cancer therapy, comprises administering an anti-CD37 immunoconjugate (e.g., IMGN529) to the patient wherein an absence of an increased expression level of at least one gene has been detected in a cancer sample obtained from the patient, and wherein the at least one gene is selected from the group consisting of: CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13.

In one instance, a method of treating a patient having cancer with an anti-CD37 immunoconjugate (e.g., IMGN529) comprises: (a) detecting the expression level of at least one gene selected from the group consisting of: SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP1, in a cancer sample obtained from the patient; (b) determining the expression level of the at least one gene, wherein an increased expression level of the at least one gene indicates that the patient is likely to respond to treatment with the anti-CD37 immunoconjugate (e.g., IMGN529); and (c) administering the anti-CD37 immunoconjugate (e.g., IMGN529) to the patient if the expression level of the at least one gene indicates that the patient is likely to respond to treatment with the anti-CD37 immunoconjugate (e.g., IMGN529).

In one instance, a method of treating a patient having cancer with a anti-CD37 immunoconjugate (e.g., IMGN529) comprises: (a) detecting the expression level of at least one gene selected from the group consisting of: CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13, in a cancer sample obtained from the patient; (b) determining the expression level of the at least one gene, wherein an absence of increased expression level of the at least one gene indicates that the patient is likely to respond to treatment with the anti-CD37 immunoconjugate (e.g., IMGN529); and (c) administering the anti-CD37 immunoconjugate to the patient if the expression level of the at least one gene indicates that the patient is likely to respond to treatment with the anti-CD37 immunoconjugate (e.g., IMGN529).

In some instances, an increased expression level of CD37 (e.g., CD37 nucleic acid or protein) has also been detected in a cancer sample from the patient. In some instances, CD37 protein is detected using immunohistochemistry.

In some instances, an increased expression level of at least 2, 3, 4, or 5 genes selected from the group consisting of: SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP1 has been detected in a cancer sample obtained from the patient. In another instance, an increased expression level has been detected in a cancer sample obtained from the patient for at least one gene selected from the group consisting of: SLC6A16, CD79A, CHI3L2, FAM117B, LPAR5, NFATC1, PTPN22, RBM38, and SGPP1.

In some instances, an increased expression level has been detected in a cancer sample obtained from the patient for at least one gene selected from the group consisting of:

SLC6A16, CD79A, CXCR5, PTPN22, LCK, CD22, and PDE4B. In some instances, an increased expression level has been detected in a cancer sample obtained from the patient for at least one gene selected from the group consisting of: CXCR5, LCK, CD22, PTPN22, BASP1, BIK, LY86, TLR10, CD86, BCL6, PIK3IP1, and CDKN2A. In some instances, an increased expression level has been detected in a cancer sample obtained from the patient for at least one gene selected from the group consisting of: PDE4B, AFF3, PIM1, MGMT, NFKBIE, SYK, and FOXO1.

In some instances, the anti-CD37 immunoconjugate comprises an antibody or antigen-binding fragment thereof that competitively inhibits the binding of an antibody with the sequences of SEQ ID NOs: 12 and 15 to CD37. In some instances, the anti-CD37 immunoconjugate comprises an antibody or antigen-binding fragment thereof that binds to the same epitope as an antibody with the sequences of SEQ ID NOs: 12 and 15. In some instances, the anti-CD37 immunoconjugate comprises an antibody or antigen-binding fragment thereof that binds to the same epitope as an antibody with the sequences of SEQ ID NOs: 12 and 15 and competitively inhibits the binding of an antibody with the sequences of SEQ ID NOs: 12 and 15 to CD37.

In some instances, the anti-CD37 immunoconjugate comprises an antibody or antigen-binding fragment thereof having the variable heavy chain sequence of SEQ ID NO: 12. In some instances, the anti-CD37 immunoconjugate comprises an antibody or antigen-binding fragment thereof having the variable light chain sequence of SEQ ID NO: 15. In some instances, the anti-CD37 immunoconjugate comprises an antibody or antigen-binding fragment thereof having the variable heavy chain sequence of SEQ ID NO: 12 and the variable light chain sequence of SEQ ID NO: 15. In some instances, the anti-CD37 immunoconjugate comprises an antibody or antigen-binding fragment thereof having the full-length heavy chain amino acid sequence of SEQ ID NO:18. In some instances, the anti-CD37 immunoconjugate comprises an antibody or antigen-binding fragment thereof having the full-length light chain amino acid sequence of SEQ ID NO:21. In some instances, the anti-CD37 immunoconjugate comprises an antibody or antigen-binding fragment thereof having the full-length heavy chain amino acid sequence of SEQ ID NO:18 and the full-length light chain amino acid sequence of SEQ ID NO:21.

In some instances, the anti-CD37 immunoconjugate comprises the maytansinoid DM1. In another instance, the anti-CD37 immunoconjugate comprises a linker that is SMCC.

In some instances, the anti-CD37 immunoconjugate comprises an antibody or antigen-binding fragment thereof having the variable heavy chain sequence of SEQ ID NO: 12 and the variable light chain sequence of SEQ ID NO: 15, and a maytansinoid. In some instances, the anti-CD37 immunoconjugate comprises an antibody or antigen-binding fragment thereof having the variable heavy chain sequence of SEQ ID NO: 12 and the variable light chain sequence of SEQ ID NO: 15, and the cytotoxic agent DM1. In some instances, the anti-CD37 immunoconjugate comprises an antibody or antigen-binding fragment thereof having the variable heavy chain sequence of SEQ ID NO: 12 and the variable light chain sequence of SEQ ID NO: 15, the cytotoxic agent DM1, and a non-cleavable linker. In some instances, the anti-CD37 immunoconjugate comprises an antibody or antigen-binding fragment thereof having the variable heavy chain sequence of SEQ ID NO: 12 and the variable light chain sequence of SEQ ID NO: 15, the cytotoxic agent DM1, and the linker SMCC.

In some instances, the anti-CD37 immunoconjugate comprises an antibody or antigen-binding fragment thereof having the full-length heavy chain amino acid sequence of SEQ ID NO:18 and the full-length light chain amino acid sequence of SEQ ID NO:21 and a maytansinoid. In some instances, the anti-CD37 immunoconjugate comprises an antibody or antigen-binding fragment thereof having the full-length heavy chain amino acid sequence of SEQ ID NO:18 and the full-length light chain amino acid sequence of SEQ ID NO:21 and the cytotoxic agent DM1. In some instances, the anti-CD37 immunoconjugate comprises an antibody or antigen-binding fragment thereof having the full-length heavy chain amino acid sequence of SEQ ID NO:18 and the full-length light chain amino acid sequence of SEQ ID NO:21, the cytotoxic agent DM1, and a non-cleavable linker. In some instances, the anti-CD37 immunoconjugate comprises an antibody or antigen-binding fragment thereof having the full-length heavy chain amino acid sequence of SEQ ID NO:18 and the full-length light chain amino acid sequence of SEQ ID NO:21, the cytotoxic agent DM1, and the linker SMCC.

In some instances, the anti-CD37 immunoconjugate comprises an antibody or antigen-binding fragment thereof that comprises heavy chain and light chain variable region CDR sequences of SEQ ID NOs: 4-6 and SEQ ID NOs: 7-9, respectively, and a maytansinoid. In some instances, the anti-CD37 immunoconjugate comprises an antibody or antigen-binding fragment thereof that comprises heavy chain and light chain variable region CDR sequences of SEQ ID NOs: 4-6 and SEQ ID NOs: 7-9, respectively, and the cytotoxic agent DM1. In some instances, the anti-CD37 immunoconjugate comprises an antibody or antigen-binding fragment thereof that comprises heavy chain and light chain variable region CDR sequences of SEQ ID NOs: 4-6 and SEQ ID NOs: 7-9, respectively, the cytotoxic agent DM1, and a non-cleavable linker. In some instances, the anti-CD37 immunoconjugate comprises an antibody or antigen-binding fragment thereof that comprises heavy chain and light chain variable region CDR sequences of SEQ ID NOs: 4-6 and SEQ ID NOs: 7-9, respectively, the cytotoxic agent DM1, and the linker SMCC.

In some instances, the anti-CD37 immunoconjugate comprises an antibody or antigen-binding fragment thereof that contains the same heavy chain and light chain variable region sequences of the antibody produced by the hybridoma of ATCC Deposit Designation PTA-10664, deposited with the ATCC on Feb. 18, 2010. In some instances, the anti-CD37 immunoconjugate comprises an antibody or antigen-binding fragment thereof that contains the same heavy chain and light chain variable region sequences of the antibody produced by the hybridoma of ATCC Deposit Designation PTA-10664 and a maytansinoid. In some instances, the anti-CD37 immunoconjugate comprises an antibody or antigen-binding fragment thereof that contains the same heavy chain and light chain variable region sequences of the antibody produced by the hybridoma of ATCC Deposit Designation PTA-10664 and the cytotoxic agent DM1. In some instances, the anti-CD37 immunoconjugate comprises an antibody or antigen-binding fragment thereof that contains the same heavy chain and light chain variable region sequences of the antibody produced by the hybridoma of ATCC Deposit Designation PTA-10664, the cytotoxic agent DM1, and a non-cleavable linker. In some instances, the anti-CD37 immunoconjugate comprises an antibody or antigen-binding fragment thereof that contains the same heavy chain and light chain variable region sequences of the antibody produced by the hybridoma of ATCC Deposit Designation PTA-10664, the cytotoxic agent DM1, and the linker SMCC.

In some instances, the anti-CD37 immunoconjugate comprises an antibody or antigen-binding fragment thereof that contains the same heavy chain and light chain sequences of the antibody produced by the hybridoma of ATCC Deposit Designation PTA-10664. In some instances, the anti-CD37 immunoconjugate comprises an antibody or antigen-binding fragment thereof that contains the same heavy chain and light chain sequences of the antibody produced by the hybridoma of ATCC Deposit Designation PTA-10664 and a maytansinoid. In some instances, the anti-CD37 immunoconjugate comprises an antibody or antigen-binding fragment thereof that contains the same heavy chain and light chain sequences of the antibody produced by the hybridoma of ATCC Deposit Designation PTA-10664 and the cytotoxic agent DM1. In some instances, the anti-CD37 immunoconjugate comprises an antibody or antigen-binding fragment thereof that contains the same heavy chain and light chain sequences of the antibody produced by the hybridoma of ATCC Deposit Designation PTA-10664, the cytotoxic agent DM1, and a non-cleavable linker. In some instances, the anti-CD37 immunoconjugate comprises an antibody or antigen-binding fragment thereof that contains the same heavy chain and light chain sequences of the antibody produced by the hybridoma of ATCC Deposit Designation PTA-10664, the cytotoxic agent DM1, and the linker SMCC.

In some instances, the immunoconjugate is IMGN529.

In some instances, the method further comprises detecting the expression level in the cancer sample obtained from the patient prior to administering the anti-CD37 immunoconjugate.

In some instances, the detection method used to detect the expression level of the at least one gene is cytofluorometry, flow cytometry, protein microarray, immunoassay, mass spectrometry, fluorescence activated cell sorting (FACS), ELISA, SDS-PAGE, or dot blot. In some instances, the detection method used to detect the expression level of the at least one gene is nucleotide microarray, quantitative PCR, semi-quantitative PCR, RNase protection assay, in situ hybridization, or RNA-Seq.

In some instances, the increased expression or decreased expression has been detected by comparing the expression level of the at least one gene to the expression level of at least one reference gene selected from the group consisting of: ACTB, GAPDH, GUSB, HPRT1, and 18S rRNA. In some instances, the increased expression is an increase that is at least 1.5-fold greater than the change in expression level of the reference gene. In some instances, the increased expression is an increase that is at least 2-fold greater than the change in expression level of the reference gene. In some instances, the increased expression is at least 3-fold greater than the change in expression level of the reference gene. In some instances, wherein the increased expression is at least 5-fold greater than the change in expression level of the reference gene. In some instances, the increased expression is at least 10-fold greater than the change in expression level of the reference gene. In some instances, the increased expression is 2-fold to 500-fold greater than the change in expression level of the reference gene. In some instances, the increased expression is 3-fold to 400-fold greater than the change in expression level of the reference gene. In some instances, the increased expression is 4-fold to 300-fold greater than the change in expression level of the reference gene.

In some instance, the increased expression level is increased mRNA. In some instances, the increased expression level is increased protein.

In some instances, the cancer sample is tissue, blood, plasma, bone marrow, or lymph.

In some instances, the anti-CD37 immunoconjugate (e.g., IMGN529) is administered at a dose of about 0.1 mg of anti-CD37 immunoconjugate per kg of body weight (mg/kg) to about 3 mg/kg. In some instances, the anti-CD37 immunoconjugate (e.g., IMGN529) is administered at a dose of about 1 mg/kg to about 3 mg/kg. In some instances, the anti-CD37 immunoconjugate (e.g., IMGN529) is administered at a dose of about 1 mg/kg to about 2.8 mg/kg. In some instances, the anti-CD37 immunoconjugate (e.g., IMGN529) is administered at a dose of about 0.4 mg/kg to about 0.8 mg/kg. In some instances, the anti-CD37 immunoconjugate (e.g., IMGN529) is administered at a dose of about 0.8 mg/kg to about 1.4 mg/kg. In some instances, the anti-CD37 immunoconjugate (e.g., IMGN529) is administered at a dose of about 1 mg/kg to about 1.4 mg/kg. In some instances, the anti-CD37 immunoconjugate (e.g., IMGN529) is administered at a dose of about 1.4 mg/kg to about 2 mg/kg. In some instances, the anti-CD37 immunoconjugate (e.g., IMGN529) is administered at a dose of about 1.4 mg/kg to about 3 mg/kg. In some instances, the anti-CD37 immunoconjugate (e.g., IMGN529) is administered at a dose of about 1.4 mg/kg to about 2.8 mg/kg. In some instances, the anti-CD37 immunoconjugate (e.g., IMGN529) is administered at a dose of about 2 mg/kg to about 2.8 mg/kg. In some instances, the anti-CD37 immunoconjugate (e.g., IMGN529) is administered at a dose of about 2 mg/kg to about 3 mg/kg. In some instances, the anti-CD37 immunoconjugate (e.g., IMGN529) is administered at a dose of 0.7 mg/kg (e.g., once every three weeks). In some instances, the anti-CD37 immunoconjugate (e.g., IMGN529) is administered at a dose of 1.0 mg/kg (e.g., once every three weeks). In some instances, the anti-CD37 immunoconjugate (e.g., IMGN529) is administered at a dose of 1.4 mg/kg (e.g., once every three weeks wherein G-CSF is also administered).

According to the methods described herein, the anti-CD37 immunoconjugate (e.g., IMGN529) can be administered about once every 3 weeks. In some instances, the anti-CD37 immunoconjugate (e.g., IMGN529) is administered on day 1 of a 21 day cycle.

In some instances, the anti-CD37 immunoconjugate (e.g., IMGN529) is administered intravenously.

In some instances, the method further comprises administering a corticosteroid (e.g., to reduce or prevent side effects). In some instances, the corticosteroid is administered to reduce hematological adverse events including, for example, neutropenia and febrile neutropenia. Thus, in some instances, the corticosteroid is administered to decrease, shorten, or prevent neutropenia or febrile neutropenia. In some instances, the neutropenia presents early in the dosing cycle. In some instances, the neutropenia is febrile neutropenia.

In some instances, the corticosteroid is administered prior to administration of the anti-CD37 immunoconjugate (e.g., IMGN529). In some instances, the corticosteroid is administered 30 to 60 minutes prior to administration of anti-CD37 immunoconjugate (e.g., IMGN529). In some instances, the corticosteroid is administered during the administration of the anti-CD37 immunoconjugate (e.g., IMGN529). In some instances, the corticosteroid is administered at least one additional time from about one day to about four days after administration of the immunoconjugate. In some instances, the corticosteroid is administered at least one additional time from about one day to about three days after administration of the immunoconjugate. In some instances, the corticosteroid is administered at least two additional times. In some instances, the corticosteroid is further administered on day two and day three after administration of the immunoconjugate. In some instances, the corticosteroid is administered after the administration of the immunoconjugate.

In some instances, the corticosteroid is selected from the group consisting of prednisone, prednisolone, methylprednisolone, beclamethasone, betamethasone, dexamethasone, fludrocortisone, hydrocortisone, and triamcinolone. In some instances, the corticosteroid is dexamethasone. In some instance, the corticosteroid is administered peri-infusionally.

In some instances, the method further comprises administering a growth factor.

In some instances, the growth factor is selected from the group consisting of granulocyte colony-stimulating factor (G-CSF), granulocyte-macrophage colony-stimulating factor (GM-CSF), macrophage colony-stimulating factor (M-CSF), filgrastim, and pegfilgrastim. In some instances, the growth factor is G-CSF.

In some instances, the growth factor is administered early to mid-cycle (e.g., of a 21-day cycle). In some instances, the growth factor is administered at least once from day one to day twelve after administration of the immunoconjugate. In some instances, the growth factor is administered at least one from day 15 to day 21 after administration of the immunoconjugate.

In some instances, the administration of corticosteroids and/or G-CSF to the dosing protocol allows a higher dose to be administered, longer duration of treatment, less neutropenia, and/or more clinical benefit.

The methods described herein can be used to treat cancer. In certain instances, the cancer is a B-cell malignancy. In certain instances, the cancer is a leukemia or lymphoma. In some instances, the cancer is selected from the group consisting of B-cell lymphomas including non-Hodgkin's lymphoma (NHL), precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal type, and splenic marginal zone lymphoma (SMZL)), hairy cell leukemia, diffuse large B-cell lymphoma (DLBCL), activated B cell like diffuse large B-cell lymphoma (ABC-DLBCL), germinal center B cell like diffuse B-cell lymphoma (GCB-DLBCL), Burkitt's lymphoma, plasmacytoma, plasma cell myeloma, post-transplant lymphoproliferative disorder, Waldenstrom's macroglobulinemia, anaplastic large-cell lymphoma (ALCL), and primary mediastinal large B-cell lymphoma (PMBCL). In certain instances, the cancer is a T-cell malignancy.

In some instances, the cancer is germinal center B cell like diffuse B-cell lymphoma (GCB-DLBCL). In some instances, an increased expression level has been detected in a cancer sample obtained from the patient having GCB-DLBCL for at least one gene selected from the group consisting of: CXCR5, LCK, CD22, PTPN22, BASP1, BIK, LY86, TLR10, CD86, BCL6, PIK3IP1, and CDKN2A.

In some instances, the cancer is activated B cell like diffuse large B-cell lymphoma (ABC-DLBCL). In some instances, an increased expression level has been detected in a cancer sample obtained from the patient having ABC-DLBCL for at least one gene selected from the group consisting of: PDE4B, AFF3, PIM1, MGMT, NFKBIE, SYK, and FOXO1.

A kit for determining whether a patient having cancer may benefit from treatment with an anti-CD37 immunoconjugate (e.g., IMGN529) is provided herein. In one instance, the kit comprises: (a) polypeptides or polynucleotides capable of determining the expression level of at least one gene selected from the group consisting of: SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP1; (b) instructions for use of the polypeptides or polynucleotides to determine the expression level of at least one gene selected from the group consisting of: SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP1; and (c) instructions for use of the polypeptides or polynucleotides to compare the expression level of the at least one gene to a reference expression level of the at least one gene; wherein an increase in the expression level of the at least one gene relative to a reference expression level indicates that the patient may benefit from treatment with an anti-CD37 immunoconjugate (e.g., IMGN529).

A combination diagnostic and pharmaceutical kit is also provided herein. In one instance, the combination diagnostic and pharmaceutical kit comprises: (a) a polypeptide, polynucleotide, or antibody capable of determining the expression level of at least one gene selected from the group consisting of: SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP1; and (b) an anti-CD37 immunoconjugate (e.g., IMGN529).

BRIEF DESCRIPTION OF THE DRAWINGS/FIGURES

DETAILED DESCRIPTION OF THE INVENTION

Figure 1:
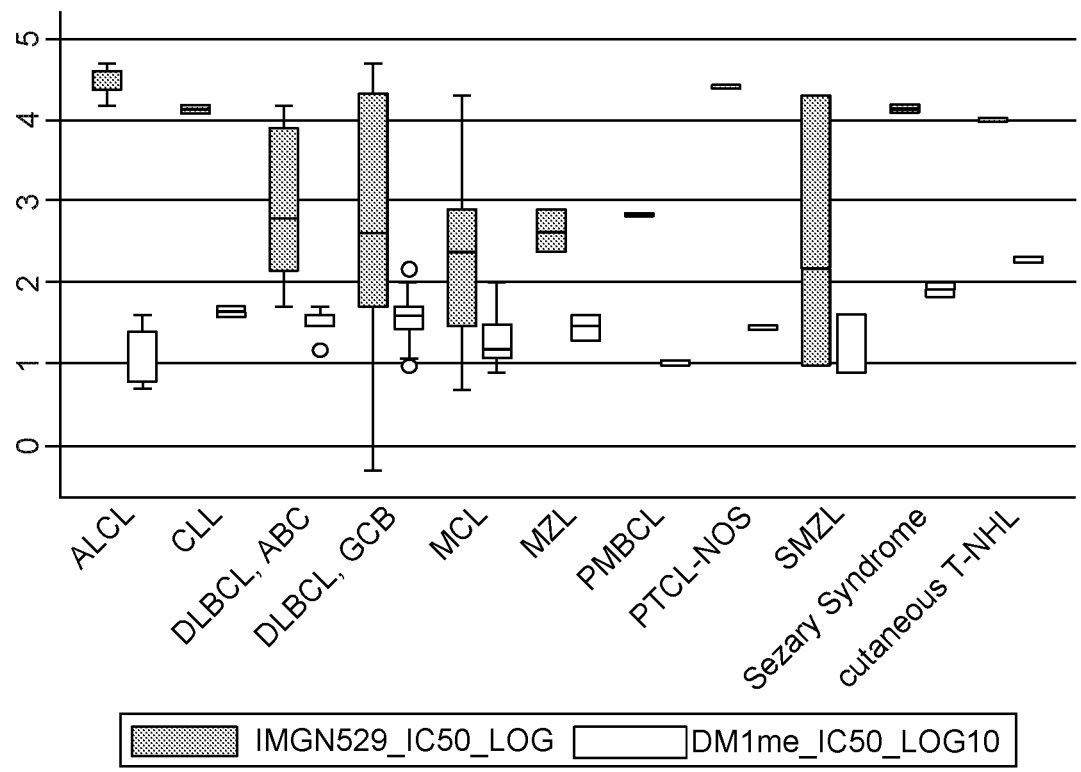
FIG. 1 shows the anti-proliferative activity of IMGN529 and the unconjugated cytotoxic payload DM1 in various non-Hodgkin lymphoma cell lines.

The present invention provides for identifying and treating patients whose cancers are sensitive or responsive to treatment with an anti-CD37 immunoconjugate (e.g., IMGN529).

I. Definitions

To facilitate an understanding of the present invention, a number of terms and phrases are defined below.

The term "CD37" as used herein, refers to any native CD37, unless otherwise indicated. CD37 is also referred to as GP52-40, leukocyte antigen CD37, and Tetraspanin-26. The term "CD37" encompasses "full-length", unprocessed CD37 as well as any form of CD37 that results from processing in the cell. The term also encompasses naturally occurring variants of CD37, e.g., splice variants, allelic variants, and isoforms. The CD37 polypeptides described herein can be isolated from a variety of sources, such as from human tissue types or from another source, or prepared by recombinant or synthetic methods. Where specifically indicated, "CD37" can be used to refer to a nucleic acid that encodes a CD37 polypeptide. As used herein, the term "human CD37" refers to the protein with the amino acid sequence of SEQ ID NO:1.

The term "anti-CD37 immunoconjugate" refers to immunoconjugates that specifically bind to CD37.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, multispecific antibodies such as bispecific antibodies generated from at least two intact antibodies, chimeric antibodies, humanized antibodies, human antibodies, fusion proteins comprising an antibody, and any other modified immunoglobulin molecule so long as the antibodies exhibit the desired biological activity. An antibody can be of any of the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. A "blocking" antibody or an "antagonist" antibody is one which inhibits or reduces biological activity of the antigen it binds, such as CD37. In some instances, blocking antibodies or antagonist antibodies substantially or completely inhibits the biological activity of the antigen. The biological activity can be reduced by 10%, 20%, 30%, 50%, 70%, 80%, 90%, 95%, or even 100%.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein can be less than about 10% of the binding of the antibody to CD37 as measured, e.g., by a radioimmunoassay (RIA). In certain instances, an antibody that binds to CD37 has a dissociation constant (Kd) of ≤1 µM, ≤100 nM, ≤10 nM, ≤1 nM, or ≤0.1 nM.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal" can refer to both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized" antibody refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539, Roguska et al., Proc. Natl. Acad. Sci., USA, 91(3):969-973 (1994), and Roguska et al., Protein Eng. 9(10):895-904 (1996). In some instances, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The term "human," when referring to an antibody, means an antibody produced by a human or an antibody having an amino acid sequence corresponding to an antibody produced by a human made using any technique known in the art. This definition of a "human" antibody or antigen-binding fragment thereof includes intact or full-length antibodies, fragments thereof, and/or antibodies comprising at least one human heavy and/or light chain polypeptide such as, for example, an antibody comprising murine light chain and human heavy chain polypeptides.

The term "chimeric" antibodies refer to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd) Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative instances are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to at least a portion of that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some instances, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or antigen-binding fragment thereof) and is defined by a generic formula: C-L-A, wherein C=cytotoxin, L=linker, and A=anti-CD37 antibody or antibody fragment. Immunoconjugates can also be defined by the generic formula in reverse order: A-L-C.

The term "IMGN529" refers to the immunoconjugate described herein containing the huCD37-3 antibody (i.e., an antibody with the amino acid sequence of the antibody produced by the hybridoma of ATCC Deposit Designation PTA-10664, comprising the CDRs represented by SEQ ID NOs:4-9, the VH of SEQ ID NO:12 and the VL of SEQ ID NO:15), the SMCC linker, and the DM1 maytansinoid. IMGN529 is also referred to as naratuximab emtansine.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and known in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal type, and splenic marginal zone lymphoma (SMZL)), hairy cell leukemia, diffuse large B-cell lymphoma, Burkitt's lymphoma, plasmacytoma, plasma cell myeloma, post-transplant lymphoproliferative disorder, Waldenstrom's macroglobulinemia, anaplastic large-cell lymphoma (ALCL), and primary mediastinal large B-cell lymphoma (PMBCL).

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody or immunoconjugate as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100 in a model of animals implanted with a tumor. A favorable response can be assessed also in the clinic, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof.

PFS, DFS, and OS can be measured by standards set by the National Cancer Institute and the U.S. Food and Drug Administration for the approval of new drugs. See Johnson et al, (2003) J. Clin. Oncol. 21(7):1404-1411.

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

"Time to Tumor Progression" (TTP) is defined as the time from enrollment to disease progression. TTP is generally measured using the RECIST 1.1 criteria.

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20 percent since treatment began, either due to increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

The term "overexpression" of CD37 in a particular tumor, tissue, or cell sample refers to CD37 (a CD37 polypeptide or a nucleic acid encoding such a polypeptide) that is present at a level higher than that which is present in non-diseased tissue or cells of the same type or origin. Such overexpression can be caused, for example, by mutation, gene amplification, increased transcription, or increased translation.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain instances, a subject is successfully "treated" for cancer according to the methods of the present invention if the patient shows one or more of the following: a reduction in the number of or complete absence of cancer cells; a reduction in the tumor burden; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

Prophylactic or preventative measures refer to measures that prevent and/or slow the development of a targeted pathological condition or disorder. Thus, those in need of prophylactic or preventative measures include those prone to have the disorder and those in whom the disorder is to be prevented.

The terms "pre-treat" and "pre-treatment" refer to therapeutic measures that occur prior to the administration of an anti-CD37 therapeutic. For example, as described in more detail herein, a prophylactic such as a steroid (e.g., corticosteroid) can be administered within about a week, about five days, about three days, about two days, or about one day or 24 hours prior to the administration of the anti-CD37 therapeutic. The prophylactic can also be administered prior to the anti-CD37 therapeutic on the same day as the anti-CD37 therapeutic.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain instances, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, Proc. Natl. Acad. Sci., 87:2264-2268, as modified in Karlin et al., 1993, Proc. Natl. Acad. Sci., 90:5873-5877, and incorporated into the NBLAST and XBLAST programs (Altschul et al., 1991, Nucleic Acids Res., 25:3389-3402). In certain instances, Gapped BLAST can be used as described in Altschul et al., 1997, Nucleic Acids Res. 25:3389-3402. BLAST-2, WU-BLAST-2 (Altschul et al., 1996, Methods in Enzymology, 266:460-480), ALIGN, ALIGN-2 (Genentech, South San Francisco, Calif.) or Megalign (DNASTAR) are additional publicly available software programs that can be used to align sequences. In certain instances, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative instances, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain instances, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain instances, the default parameters of the alignment software are used. In certain instances, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some instances, at least 95%, 96%, 97%, 98%, or 99% identical) to a reference sequence can, in certain instances, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some instances, two nucleic acids or polypeptides of the invention are substantially identical, meaning they have at least 70%, at least 75%, at least 80%, at least 85%, at least 90%, and in some instances at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some instances, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some instances, conservative substitutions in the sequences of the polypeptides and antibodies of the invention do not abrogate the binding of the polypeptide or antibody containing the amino acid sequence, to the antigen(s), i.e., the CD37 to which the polypeptide or antibody binds. Methods of identifying nucleotide and amino acid conservative substitutions which do not eliminate antigen binding are well-known in the art (see, e.g., Brummell et al., Biochem. 32: 1180-1187 (1993); Kobayashi et al. Protein Eng. 12(10):879-884 (1999); and Burks et al. Proc. Natl. Acad. Sci. USA 94:412-417 (1997)).

Increased expression level, an absence of increased expression level, or decreased expression level of a "gene" as used herein can refer to DNA, RNA, or protein, the expression or presence of which in a subject's or patient's sample can be detected by standard methods (or methods disclosed herein) and is useful for monitoring the responsiveness or sensitivity of a subject to a anti-CD37 immunoconjugate (e.g., IMGN529). Such genes include, but are not limited to CD79A, CHI3L2, FAM117B, LPAR5, NFATC1, PTPN22, RBM38, SGPP1, SLC6A16, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CD44, VIM, ANXA2, BCL2, ANXA2P1, HSP90B1, NFKBIZ, CDK6, BIRC5, NOTCH1, HEBP1, PHB, PSME3, RNU6-15, RPL13, CADM1, TUBB2A, and TUBG1.

"Increased expression level" refers to an expression level that is greater in a cancer sample than in a control sample, and wherein the change in the expression level between the cancer sample and the control sample is larger than the change in the expression level of a reference gene between the cancer sample and the control sample. In some instances, an increased expression level refers to an increase in expression level that is at least 1.5-fold, at least 2-fold, at least 3-fold, at least 5-fold, or at least 10-fold greater than the change in the expression level of the reference gene. In some instances, an increased expression level refers to an increase in expression level that is 1.5-fold to 500-fold, 2-fold to 500-fold, 3-fold to 400-fold, 4-fold to 300-fold, 1.5-fold to 250-fold, 2-fold to 250-fold, 1.5-fold to 100-fold, or 2-fold to 100-fold greater than the change in the expression level of the reference gene. An "absence of increased expression level" refers to an expression level that is not greater in a cancer sample than in a control sample, i.e., an expression level that is equivalent to or decreased as compared to the expression level in the control sample. "Decreased expression level" refers to an expression level that is less in a cancer sample than a control sample, and wherein the change in the expression level between the cancer sample and the control sample is larger than the change in the expression level of a reference gene between the cancer sample and the control sample. In some instances, a decreased expression level refers to an expression level that is at least 1.5 fold, at lease 2-fold, at least 3-fold, at least 5-fold, or at least 10-fold less than the change in expression level of the reference gene. In some instances, a decreased expression level refers to a decrease in expression level that is 1.5-fold to 500-fold, 2-fold to 500-fold, 3-fold to 400-fold, 4-fold to 300-fold, 1.5-fold to 250-fold, 2-fold to 250-fold, 1.5-fold to 100-fold, or 2-fold to 100-fold less than the change in the expression level of a reference gene. In some instances, increased expression level refers to an expression level that is greater than the expression of an internal reference gene or external reference standard (e.g., an artificial DNA or RNA construct in a cell line).

The term "control sample" refers to a non-cancerous sample.

The term "reference gene" as used herein refers to any gene or genes constitutively expressed in a cell in normal and/or pathological states. Such a gene can be used as a reference because its expression is detectable at a consistent amount across different physiological conditions. In some instances, the average of three or sometimes five reference genes can be used. In some instances, the reference gene is a housekeeping gene. In some instances, a housekeeping gene encodes a protein required for basic cellular function and/or maintenance. Examples of such reference genes include, but are not limited to, beta actin (ACTB), glyceraldeyde-3-phosphate dehydrogenase (GAPDH), beta glucuronidase (GUSB), hypoxanthine guanine phosphoribosyl transferase (HPRT1), and ribosome small subunit (18S) ribosomal RNA (18S rRNA). In another instance, a reference gene can be any gene disclosed in Eli Eisenberg and Erez Lavanon (2013) (Human housekeeping genes, revisited. *Trends Genet.* 29(10):569-74.

The terms "sample" and "biological sample" are used interchangeably to refer to any biological sample obtained from an individual including body fluids, body tissue (e.g., tumor tissue), cells, or other sources. Any such sample may be fresh or frozen, and if relevant also fixed (e.g. FFPE). Body fluids are, e.g., lymph, sera, whole fresh blood, peripheral blood mononuclear cells, frozen whole blood, plasma (including fresh or frozen), urine, saliva, semen, synovial fluid and spinal fluid. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art. A biological sample can be a "cancer sample". The term "cancer sample" refers to a sample obtained from a cancer in an individual.

The terms "tissue sample" or "cell sample" refer to a collection of similar cells obtained from a tissue of a subject. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

As used herein, a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to protein or nucleic acid.

By "detecting the expression level" of a gene is meant determining, in any way, the amount of DNA, RNA, or protein associated with the gene. One may use the results of a detection assay in carrying out a second protocol, e.g., the administration of an anti-CD37 immunoconjugate (e.g., IMGN529), and/or one may use the results of a detection assay to determine whether CD37-binding agent (e.g., IMGN529) should be administered.

An "effective response" of a patient or a patient's "responsiveness" or "sensitivity" to treatment with an anti-CD37 immunoconjugate (e.g., IMGN529) refers to the clinical or therapeutic benefit imparted to a patient at risk for or suffering from a disease or disorder, such as cancer. Such benefit includes cellular or biological responses, an objective response (including a complete response or a partial response), a stable disease (without progression or relapse), or extended survival (including overall survival and progression free survival) of the patient from or as a result of the treatment with the antagonist. Such benefit also includes improving signs or symptoms of cancer. For example, an effective response can be reduced tumor size or progression-free survival in a patient with a tumor sample showing a particular expression level of a gene as described herein, versus a patient not showing the particular expression level of the gene as described herein. The expression of a gene or combination of genes provided herein can effectively predict, or predicts with high sensitivity, an effective response.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival and progression free survival; and/or (9) decreased mortality at a given point of time following treatment.

The term "detection" includes any means of detecting, including direct and indirect detection.

The "amount" or "level" of a gene associated with an increased clinical benefit to an individual is a detectable level in a biological or cancer sample. These can be measured by methods known to one skilled in the art and also disclosed herein. The expression level or amount of gene assessed can be used to determine the response to the treatment.

The term "reference sample" refers to a sample corresponding to normal tissue or cells taken from the same individual or a different individual. For example, the reference sample may be taken from a disease-free area of the cancer containing tissue in the subject of interest or the reference sample may be taken from disease-free tissue of the subject of interest that does not correspond to the diseased-tissue. In another example, the reference sample may be taken from the tissue of a disease-free subject, either from tissue that corresponds to the diseased-tissue of the subject of interest or other normal tissue of the disease-free subject. Reference samples can be cells (e.g., cell lines, cell pellets) or tissue. The expression level of a biomarker in the "reference sample" can be an absolute or relative amount, a range of amount, a minimum and/or maximum amount, a mean amount, and/or a median amount of the biomarker. The methods of the invention involve a comparison between expression levels of biomarker in a test sample and a "reference value."

The term "reference value" can be the expression level of a biomarker in a reference sample. A reference value can be a predetermined value and can also be determined from reference samples (e.g., control biological samples) tested in parallel with the test samples. A reference value can be a single cut-off value, such as a median or mean or a range of values, such as a confidence interval. Reference values can be established for various subgroups of individuals, such as individuals predisposed to cancer, individuals having early or late stage cancer, male and/or female individuals, or individuals undergoing cancer therapy.

As used in the present disclosure and claims, the singular forms "a", "an", and "the" include plural forms unless the context clearly dictates otherwise.

It is understood that wherever instances are described herein with the language "comprising," otherwise analogous instances described in terms of "consisting of" and/or "consisting essentially of" are also provided.

The term "and/or" as used in a phrase such as "A and/or B" herein is intended to include both "A and B", "A or B", "A", and "B". Likewise, the term "and/or" as used in a phrase such as "A, B, and/or C" is intended to encompass each of the following instances: A, B, and C; A, B, or C; A or C; A or B; B or C; A and C; A and B; B and C; A (alone); B (alone); and C (alone).

II. Anti-CD37-Immunoconjugates

The methods described herein provide methods of administering anti-CD37 immunoconjugates. Anti-CD37 immunoconjugates specifically bind to CD37. The full-length amino acid sequences for human, macaque, and murine CD37 are known in the art and also provided herein as represented by SEQ ID NOs:1-3, respectively.

Human CD37 (NP_001765.1):
(SEQ ID NO: 1)
MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNLSATNDSTILDKVILPQ

LSRLGHLARSRHSADICAVPAESHIYREGCAQGLQKWLHNNLISIVGICL

GVGLLELGFMTLSIFLCRNLDHVYNRLARYR

Macaque CD37:
(SEQ ID NO: 2)
MSAQESCLSLIKYFLFVFNLFFFVILGSLIFCFGIWILIDKTSFVSFVGL

AFVPLQIWSKVLAISGVFTMGLALLGCVGALKELRCLLGLYFGMLLLLFA

TQITLGILISTQRAQLERSLQDIVEKTIQRYHTNPEETAAEESWDYVQFQ

LRCCGWHSPQDWFQVLTLRGNGSEAHRVPCSCYNLSATNDSTILDKVILP

QLSRLGQLARSRHSTDICAVPANSHIYREGCARSLQKWLHNNLISIVGIC

LGVGLLELGFMTLSIFLCRNLDHVYNRLRYR

Murine CD37 (NP_031671):
(SEQ ID NO: 3)
MSAQESCLSLIKYFLFVFNLFFFVLGGLIFCFGTWILIDKTSFVSFVGLS

FVPLQTWSKVLAVSGVLTMALALLGCVGALKELRCLLGLYFGMLLLLFAT

QITLGILISTQRVRLERRVQELVLRTIQSYRTNPDETAAEESWDYAQFQL

RCCGWQSPRDWNKAQMLKANESEEPFVPCSCYNSTATNDSTVFDKLFFSQ

LSRLGPRAKLRQTADICALPAKAHIYREGCAQSLQKWLHNNIISIVGICL

GVGLLELGFMTLSIFLCRNLDHVYDRLARYR

In some instances, the anti-CD37 immunoconjugates comprise humanized antibodies.

In certain instances, the anti-CD37 immunoconjugates (e.g., IMGN529) have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells. In certain instances, the anti-CD37 immunoconjugates (e.g., IMGN529) trigger cell death via a cytotoxic agent. In certain instances, the anti-CD37 immunoconjugates (e.g., IMGN529) are capable of inhibiting tumor growth. In certain instances, the anti-CD37 immunoconjugates (e.g., IMGN529) are capable of inhibiting tumor growth in vivo (e.g., in a xenograft mouse model and/or in a human having cancer). The anti-CD37 immunoconjugates (e.g., IMGN529) can comprise the antibody huCD37-3 or fragments, variants and derivatives thereof, as described previously in U.S. Publication No. 2011/0256153, which is herein incorporated by reference in its entirety. The anti-CD37 immunoconjugates (e.g., IMGN529) can also comprise anti-CD37 antibodies or fragments that specifically bind to the same CD37 epitope as huCD37-3 and/or that competitively inhibit huCD37-3 binding to CD37.

In some instances, the anti-CD37 immunoconjugates (e.g., IMGN529) comprise the heavy chain and light chain variable region CDR sequences of huCD37-3. The CDR sequences of huCD37-3 are described in Tables 1 and 2 below.

TABLE 1

Variable heavy chain CDR amino acid sequences

| Antibody | VH-CDR1 | VH-CDR2 | VH-CDR3 |
|---|---|---|---|
| CD37-3 | TSGVS (SEQ ID NO: 4) | VIWGDGSTN (SEQ ID NO: 5) | GGYSLAH (SEQ ID NO: 6) |

TABLE 2

Variable light chain CDR amino acid sequences

| Antibody | VL-CDR1 | VL-CDR2 | VL-CDR3 |
|---|---|---|---|
| CD37-3 | RASENIRSNLA (SEQ ID NO: 7) | VATNLAD (SEQ ID NO: 8) | QHYWGTTWT (SEQ ID NO: 9) |

In some instances, the anti-CD37 immunoconjugates (e.g., IMGN529) comprise variable heavy chain CDR1, CDR2, and CDR3 sequences comprising SEQ ID NOs: 4, 5, and 6 and variable light chain CDR1, CDR2, and CDR3 sequences comprising SEQ ID NOs: 7, 8, and 9, respectively.

In some instances, the anti-CD37 immunoconjugates (e.g., IMGN529) comprise polypeptides comprising the variable light chains or variable heavy chains described herein. In other instances, the anti-CD37 immunoconjugates (e.g., IMGN529) comprise polypeptides comprising both a variable light chain and a variable heavy chain. The variable light chain and variable heavy chain sequences of murine, chimeric, and humanized CD37-3 antibodies are provided in Tables 3 and 4 below.

TABLE 3

Variable heavy chain amino acid sequences

| Antibody | VH Amino Acid Sequence (SEQ ID NO) |
|---|---|
| muCD37-3 | QVQVKESGPGLVAPSQSLSITCTVSGFSLTTSGVSWVRQPPGKGLEWLGVIWGDGSTNYHSALKSRLSIKKDHSKSQVFLKLNSLQTDDTATYYCAKGGYSLAHWGQGTLVTVSA (SEQ ID NO:10) |
| chCD37-3 | QVQVKESGPGLVAPSQSLSITCTVSGFSLTTSGVSWVRQPPGKGLEWLGVIWGDGSTNYHSALKSRLSIKKDHSKSQVFLKLNSLQTDDTATYYCAKGGYSLAHWGQGTLVTVSA (SEQ ID NO: 11) |
| huCD37-3 (version 1.0) | QVQVQESGPGLVAPSQTLSITCTVSGFSLTTSGVSWVRQPPGKGLEWLGVIWGDGSTNYHPSLKSRLSIKKDHSKSQVFLKLNSLTAADTATYYCAKGGYSLAHWGQGTLVTVSS (SEQ ID NO: 12) |
| huCD37-3 (version 1.1) | QVQVQESGPGLVAPSQTLSITCTVSGFSLTTSGVSWVRQPPGKGLEWLGVIWGDGSTNYHSSLKSRLSIKKDHSKSQVFLKLNSLTAADTATYYCAKGGYSLAHWGQGTLVTVSS (SEQ ID NO: 22) |

TABLE 4

Variable light chain amino acid sequences

| Antibody | VL Amino Acid Sequence (SEQ ID NO) |
|---|---|
| muCD37-3 | DIQMTQSPASLSVSVGETVTITCRASENIRSNLAWYQQKQGKSPQLLVNVATNLADGVPSRFSGSGSGTQYSLKINSLQSEDFGTYYCQHYWGTTWTFGGGTKLEIKR (SEQ ID NO: 13) |
| chCD37-3 | DIQMTQSPASLSVSVGETVTITCRASENIRSNLAWYQQKQGKSPQLLVNVATNLADGVPSRFSGSGSGTQYSLKINSLQSEDFGTYYCQHYWGTTWTFGGGTKLEIKR (SEQ ID NO: 14) |
| huCD37-3 | DIQMTQSPS SLSVSVGERVTITCRASENIRSNLAWYQQKPGKSPKLLVNVATNLADGVPSRFSGSGSGTDYSLKINSLQPEDFGTYYCQHYWGTTWTFGQGTKLEIKR (SEQ ID NO: 15) |

Also provided herein are anti-CD37 immunoconjugates (e.g., IMGN529) comprising an antibody or antigen-binding fragment thereof that specifically binds CD37. In certain instances, the antibody or antigen-binding fragment thereof that specifically binds CD37 is a murine, chimeric, or humanized antibody. In certain instances, the anti-CD37 immunoconjugate comprises an antibody or antigen-binding fragment thereof comprising: (a) a VH polypeptide having at least about 90% sequence identity to one of SEQ ID NOs: 10-12 and 22; and/or (b) a VL polypeptide having at least about 90% sequence identity to one of SEQ ID NOs:13-15, e.g., wherein the VH and VL polypeptides comprise the VH and VL CDRs in Tables 1 and 2. In certain instances, the antibody or antigen-binding fragment thereof comprises (a) a VH polypeptide having at least about 95%, at least about 96%, at least about 97%, at least about 98%, or at least about 99% sequence identity to one of SEQ ID NOs:10-12 and 22 and (b) a VL polypeptide having at least about 95%, at least about 96%, at least about 97%, at least about 98%, or at least about 99% sequence identity to one of SEQ ID NOs:13-15, e.g., wherein the VH and VL polypeptides comprise the VH and VL CDRs in Tables 1 and 2. In certain instances, the antibody or antigen-binding fragment thereof comprises (a) a VH polypeptide having at least about 95% sequence identity to one of SEQ ID NOs:10-12 and 22, and (b) a VL polypeptide having at least about 95% sequence identity to one of SEQ ID NOs:13-15. In certain instances, the antibody or antigen-binding fragment comprises (a) a VH polypeptide having the amino acid sequence of one of SEQ ID NOs:10-12 and 22; and (b) a VL polypeptide having the amino acid sequence of one of SEQ ID NOs:13-15, e.g., wherein the VH and VL polypeptides comprise the VH and VL CDRs in Tables 1 and 2. In certain instances, the antibodies or antigen-binding fragments thereof contains polypeptides that have a certain percentage of sequence identity to SEQ ID NOs:10-12 and 22 and 13-15 or differ from SEQ ID NOs:10-12 and 13-15 by conservative amino acid substitutions only, e.g., wherein the VH and VL polypeptides comprise the VH and VL CDRs in Tables 1 and 2.

The anti-CD37 immunoconjugates (e.g., IMGN529) provided herein can also comprise anti-CD37 antibodies or antigen-binding fragments thereof comprising a full-length light chain or a full-length heavy chain. In certain instances, the anti-CD37 immunoconjugates (e.g., IMGN529) can also comprise anti-CD37 antibodies or antigen-binding fragments thereof comprising both a full-length light chain and a full-length heavy chain. The full-length light chain and heavy chain sequences of murine, chimeric, and humanized CD37-3 antibodies are provided in Tables 5 and 6 below.

TABLE 5

Full-length heavy chain amino acid sequences

| Antibody | Full-Length Heavy Chain Amino Acid Sequence (SEQ ID NO) |
|---|---|
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAAKTTAPSVYPLAPVCGDTTGSSVTLGCLVKGYFPEPVTL TWNSGSLSSGVHTFPAVLQSDLYTLSSSVTVTSSTWPSQSITCNVAHPASSTK VDKKIEPRGPTIKPCPPCKCPAPNLLGGPSVFIFPPKIKDVLMISLSPIVTCVVV DVSEDDPDVQISWFVNNVEVHTAQTQTHREDYNSTLRVVSALPIQHQDWM SGKEFKCKVNNKDLPAPIERTISKPKGSVRAPQVYVLPPPEEEMTKKQVTLT CMVTDFMPEDIYVEWTNNGKTELNYKNTEPVLDSDGSYFMYSKLRVEKKN WVERNSYSCSVVHEGLHNHEITTKSFSRTPGK (SEQ ID NO: 16) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPGK (SEQ ID NO: 17) |
| huCD37-3 | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 18) |

TABLE 6

Full-length light chain amino acid sequences

| Antibody | Full-length Light Chain Amino Acid Sequence (SEQ ID NO) |
|---|---|
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKS FNRNEC (SEQ ID NO: 19) |

TABLE 6-continued

Full-length light chain amino acid sequences

| Antibody | Full-length Light Chain Amino Acid Sequence (SEQ ID NO) |
|---|---|
| chCD37-3 | DIQMTQSPASLSVSVGETVTITCRASENIRSNLAWYQQKQGKSPQLLVNVAT<br>NLADGVPSRFSGSGSGTQYSLKINSLQSEDFGTYYCQHYWGTTWTFGGGTK<br>LEIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTK<br>SFNRGEC (SEQ ID NO: 20) |
| huCD37-3 | DIQMTQSPSSLSVSVGERVTITCRASENIRSNLAWYQQKPGKSPKLLVNVAT<br>NLADGVPSRFSGSGSGTDYSLKINSLQPEDFGTYYCQHYWGTTWTFGQGTK<br>LEIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTK<br>SFNRGEC (SEQ ID NO: 21) |

Also provided herein are anti-CD37 immunoconjugates (e.g., IMGN529) comprising antibodies and antigen-binding fragments thereof that comprise: (a) a polypeptide having at least about 90% sequence identity to one of SEQ ID NOs: 16-18; and (b) a polypeptide having at least about 90% sequence identity to one of SEQ ID NOs:19-21, e.g., wherein the VH and VL polypeptides comprise the VH and VL CDRs in Tables 1 and 2. In certain instances, the antibody or antigen-binding fragment thereof comprises a polypeptide having at least about 95%, at least about 96%, at least about 97%, at least about 98%, or at least about 99% sequence identity to one of SEQ ID NOs:16-18 and a polypeptide having at least about 95%, at least about 96%, at least about 97%, at least about 98%, or at least about 99% sequence identity to one of SEQ ID NOs:19-21, e.g., wherein the VH and VL polypeptides comprise the VH and VL CDRs in Tables 1 and 2. Thus, in certain instances, the antibody or antigen-binding fragment comprises (a) a polypeptide having at least about 95% sequence identity to one of SEQ ID NOs:16-18, and/or (b) a polypeptide having at least about 95% sequence identity to one of SEQ ID NOs: 19-21, e.g., wherein the VH and VL polypeptides comprise the VH and VL CDRs in Tables 1 and 2. In certain instances, the antibody or antigen-binding fragment comprises (a) a polypeptide having the amino acid sequence of one of SEQ ID NOs:16-18; and/or (b) a polypeptide having the amino acid sequence of one of SEQ ID NOs:19-21. In certain instances, the antibody or antigen-binding fragment thereof is a murine, chimeric, or humanized antibody or fragment that specifically binds CD37. In certain instances, the antibody or antigen-binding fragment thereof comprises polypeptides differing from SEQ ID NOs:16-18 and 19-21 by conservative amino acid substitutions only, e.g., wherein the VH and VL polypeptides comprise the VH and VL CDRs in Tables 1 and 2.

In certain instances, the anti-CD37 immunoconjugate (e.g., IMGN529) comprises the anti-CD37 antibody produced from a hybridoma selected from the group consisting of consisting of ATCC Deposit Designation PTA-10664, deposited with the ATCC on Feb. 18, 2010. In certain instances, the anti-CD37 immunoconjugate (e.g., IMGN529) comprises the antibody or antigen-binding fragment thereof comprising the same amino acid sequences as the VH-CDRs and the VL-CDRs of the antibody produced from a hybridoma selected from the group consisting of PTA-10664. In certain instances, the antibody or antigen-binding fragment thereof comprises a VH with the same amino acid sequences as the VH of the antibody produced from a hybridoma selected from the group consisting of PTA-10664. In certain instances, the antibody or antigen-binding fragment comprises a VL with the same amino acid sequences as the VL of the antibody produced from a hybridoma selected from the group consisting of PTA-10664. In certain instances, the antibody or antigen-binding fragment comprises a VH and a VL with the same amino acid sequences as the VH and the VL of the antibody produced from a hybridoma selected from the group consisting of PTA-10664.

In certain instances, the anti-CD37 immunoconjugate (e.g., IMGN529) can comprise an anti-CD37 antibody or antigen-binding fragment thereof comprising a light chain or light chain variable region having the same amino acid sequence as the amino acid sequence encoded by the recombinant plasmid DNA phuCD37-3LC (ATCC Deposit Designation PTA-10722, deposited with the ATCC on Mar. 18, 2010). In certain instances, the anti-CD37 antibody or antigen-binding fragment thereof can comprise a heavy chain or heavy chain variable region comprising the same amino acid sequence as the amino acid sequence encoded by the recombinant plasmid DNA phuCD37-3HCv.1.0 (ATCC Deposit Designation PTA-10723, deposited with the ATCC on Mar. 18, 2010). In certain instances, the anti-CD37 antibody or antigen-binding fragment thereof can comprise a light chain or light chain variable region comprising the same amino acid sequence as the amino acid sequence encoded by the recombinant plasmid DNA phuCD37-3LC (PTA-10722) and a heavy chain or heavy chain variable region comprising the same amino acid sequence as the amino acid sequence encoded by the recombinant plasmid DNA phuCD37-3HCv.1.0 (PTA-10723). In certain instances, the anti-CD37 antibody or antigen-binding fragment thereof can comprise (i) VL-CDRs comprising the same amino acid sequences as the VL-CDRs encoded by the recombinant plasmid DNA phuCD37-3LC (PTA-10722) and (ii) VH-CDRs comprising the same amino acid sequences as the VH-CDRs encoded by the recombinant plasmid DNA phuCD37-3HCv.1.0 (PTA-10723).

Also provided herein are anti-CD37 immunoconjugates containing the anti-CD37 antibodies or antigen-binding fragments thereof linked to a maytansinoid drug.

The present invention includes aspects wherein about 2 to about 8 drug molecules ("drug load"), for example, maytansinoid, are linked to an anti-CD37 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-CD37 antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) can be used.

The anti-CD37 antibody or fragment thereof can be modified by reacting a bifunctional crosslinking reagent with the anti-CD37 antibody or fragment thereof, thereby resulting in the covalent attachment of a linker molecule to the anti-CD37 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

Thus, in one aspect, an immunoconjugate comprises 1 maytansinoid per antibody. In another aspect, an immunoconjugate comprises 2 maytansinoids per antibody. In another aspect, an immunoconjugate comprises 3 maytansinoids per antibody. In another aspect, an immunoconjugate comprises 4 maytansinoids per antibody. In another aspect, an immunoconjugate comprises 5 maytansinoids per antibody. In another aspect, an immunoconjugate comprises 6 maytansinoids per antibody. In another aspect, an immunoconjugate comprises 7 maytansinoids per antibody. In another aspect, an immunoconjugate comprises 8 maytansinoids per antibody.

In one aspect, an immunoconjugate comprises about 1 to about 8 maytansinoids per antibody. In another aspect, an immunoconjugate comprises about 2 to about 7 maytansinoids per antibody. In another aspect, an immunoconjugate comprises about 2 to about 6 maytansinoids per antibody. In another aspect, an immunoconjugate comprises about 2 to about 5 maytansinoids per antibody. In another aspect, an immunoconjugate comprises about 3 to about 5 maytansinoids per antibody. In another aspect, an immunoconjugate comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g., maytansinoids) per antibody.

In one aspect, a composition comprising immunoconjugates has an average of about 2±0.5, about 3±0.5, about 4±0.5, about 5±0.5, about 6±0.5, about 7±0.5, or about 8±0.5 drug molecules (e.g., maytansinoids) attached per antibody. In one aspect, a composition comprising immunoconjugates has an average of about 3.5±0.5 drug molecules (e.g., maytansinoids) per antibody.

The drug molecules can also be linked to the antibody molecules through an intermediary carrier molecule such as serum albumin.

As used herein, the expression "linked to a cell-binding agent" or "linked to an anti-CD37 antibody or fragment" refers to the conjugate molecule comprising at least one drug derivative bound to a cell-binding agent anti-CD37 antibody or fragment via a suitable linking group, or a precursor thereof. One linking group is SMCC.

In certain instances, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain instance, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

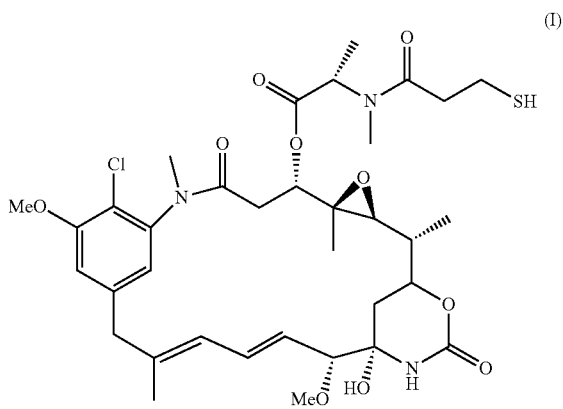 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

In another instance, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (II):

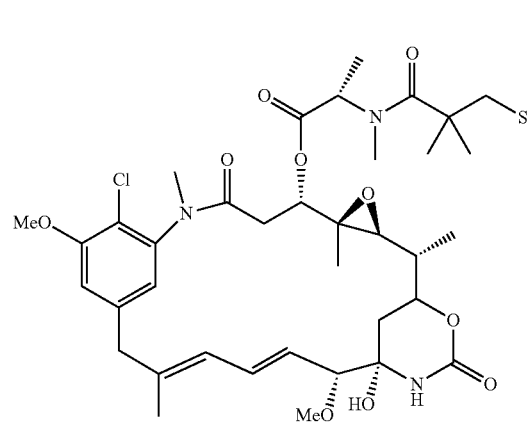
(II)
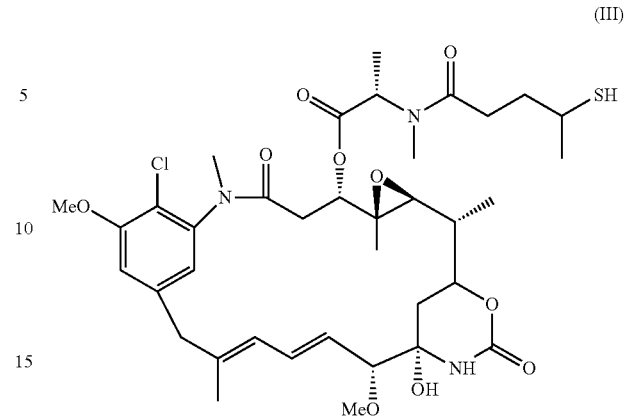
(III)
Another maytansinoid comprising a side chain that contains a sterically hindered thiol bond is $N^{2'}$-deacetyl-N-$2'$(4-mercapto-1-oxopentyl)-maytansine (termed DM3), represented by the following structural formula (III):
Structural representations of some conjugates are shown below:
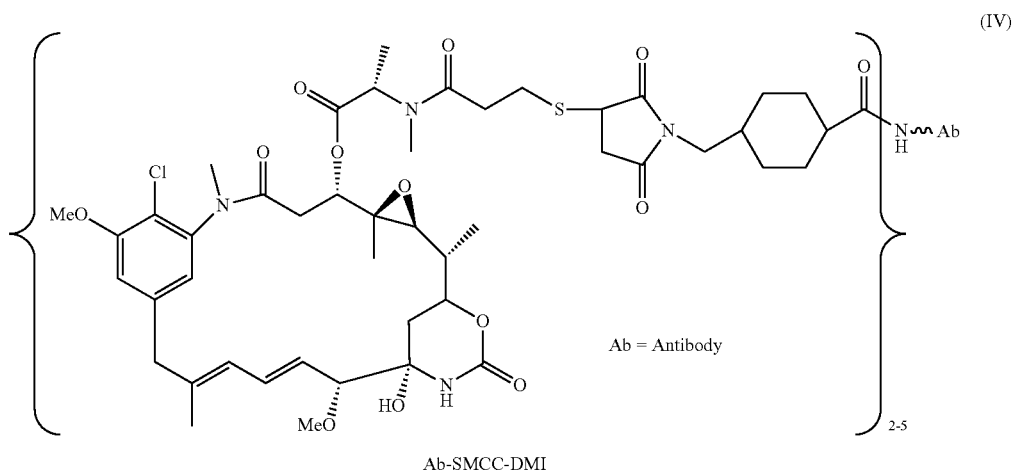
(IV)
Ab-SMCC-DM1
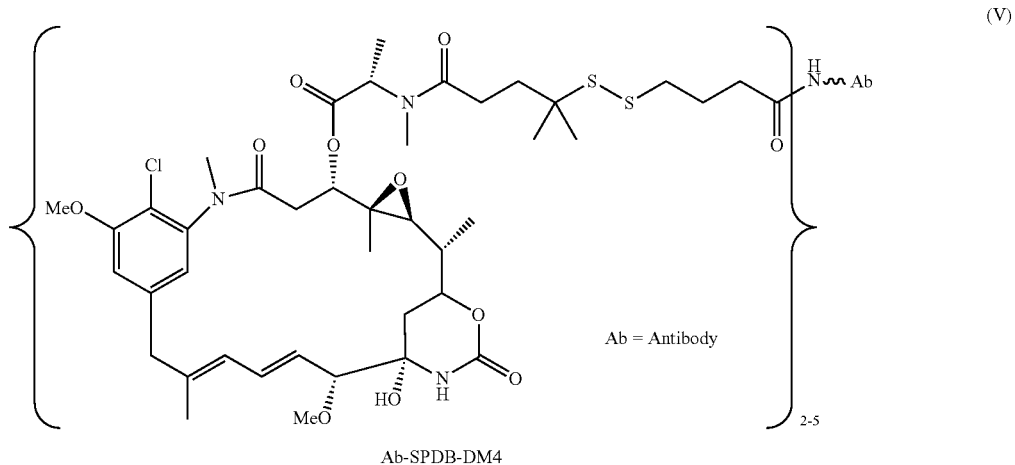
(V)
Ab-SPDB-DM4

-continued

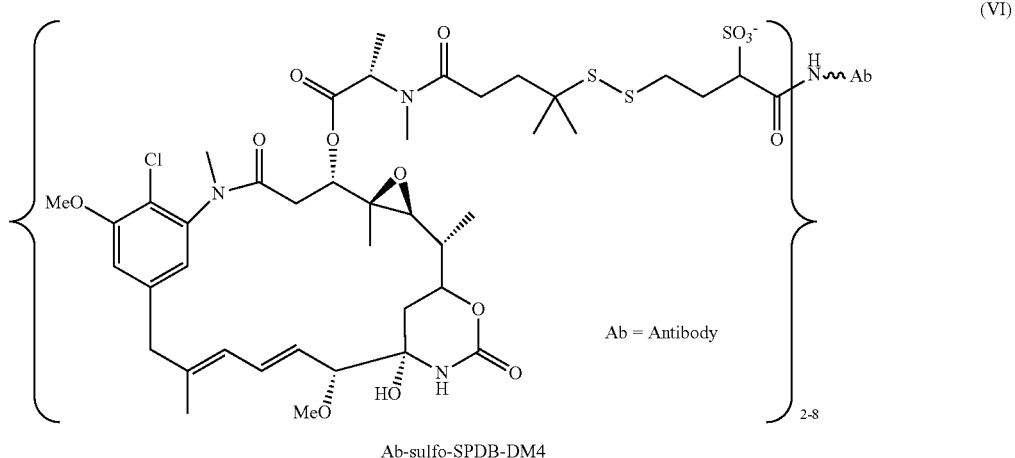

Ab-sulfo-SPDB-DM4

Also included in the present invention are any stereoisomers and mixtures thereof for any compounds or conjugates depicted by any structures above.

The immunoconjugates can, according to some instances described herein, be internalized into cells. The immunoconjugate, therefore, can exert a therapeutic effect when it is taken up by, or internalized, by a CD37-expressing cell. In some particular instances, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a CD37-expressing cell.

III. Identification of Patients Responsive to Anti-CD37 Immunoconjugates

The present invention provides methods for identifying and/or treating patients likely to be responsive to anti-CD37 immunoconjugate (e.g., IMGN529) therapy. The methods are useful, for example, for increasing the likelihood that administration of an anti-CD37 immunoconjugate (e.g., IMGN529) to a patient will be efficacious. The methods comprise detecting expression of one or more genes (e.g., DNA, RNA, or protein) in a cancer sample from a patient, wherein the expression of one or more such genes is indicative of whether the patient is sensitive or responsive, or on the contrary—resistant, to an anti-CD37 immunoconjugate (e.g., IMGN529).

More particularly, determining the expression level of at least one gene selected from the group consisting of: (i) SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP or (ii) CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13 in a sample from a patient is useful for monitoring whether the patient is responsive or sensitive to an anti-CD37 immunoconjugate (e.g., IMGN529). For any of the methods described herein, one could, for example, determine the expression levels of any combination of genes (i) selected from the group consisting of SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP and/or (ii) selected from the group consisting of CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13. Alternatively, for any of the methods described herein, the expression level of all genes (e.g., SLC6A16, CD79A, BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CHI3L2, FAM117B, LPAR5, NFATC1, PTPN22, RBM38, and SGPP and/or CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13) can be determined.

The methods and kits of this invention provide for convenient, efficient, and potentially cost-effective means to obtain data and information useful in assessing appropriate or effective therapies for treating patients. For example, a patient can provide a biological sample (e.g., tissue, blood, plasma, bone marrow, or lymph) before treatment with an anti-CD37 immunoconjugate (e.g., IMGN529) and the sample can be examined by way of various in vitro assays to determine whether the patient is likely to respond to or benefit from treatment comprising an anti-CD37 immunoconjugate (e.g., IMGN529).

The invention also provides methods for identifying the sensitivity or responsiveness of a patient to an anti-CD37 immunoconjugate (e.g., IMGN529). The methods can be conducted in a variety of assay formats, including assays detecting genetic or protein expression (such as PCR and immunoassays) and biochemical assays detecting appropriate activity. Determination of expression or the presence of such gene expression levels in patient samples is predictive of whether a patient is sensitive to the biological effects of an anti-CD37 immunoconjugate (e.g., IMGN529). The invention herein is that the expression level (e.g., an increase or an absence of an increase (e.g., a decrease)) of a gene or combination of genes listed in Table 7 in a cancer sample from a patient correlates with the outcome of such a patient treated with an anti-CD37 immunoconjugate (e.g., IMGN529). The accession numbers for sequences of the genes (polynucleotides or polypeptides) are provided in Table 7. The sequences (polypeptides or polynucleotides) are provided below Table 7. The detection of the expression of these genes can be detection of nucleic acids or proteins, as described in detail below. Example 1 shows that response to an anti-CD37 immunoconjugate correlates with the expression levels of at least one gene as described in Table 7 and thus in various instances detection of such levels in the methods described herein are included in the invention.

As provided herein, an increase in expression level of certain genes is associated with sensitivity or responsiveness to treatment with an anti-CD37 immunoconjugate (e.g., IMGN529). Typically, an increase of at least 1.5-fold to 500-fold, 2-fold to 500-fold, 3-fold to 400-fold, 4-fold to 300-fold, 1.5-fold to 250-fold, 2-fold to 250-fold, 1.5-fold to 100-fold, or 2-fold to 100-fold in expression in at least one of the genes higher than the expression level of a reference gene indicates that a patient is likely to respond to or be sensitive to treatment with an anti-CD37 immunoconjugate (e.g., IMGN529).

As provided herein, an absence of an increase in expression level (e.g., a decrease in expression level) of certain genes is associated with sensitivity or responsiveness to treatment with an anti-CD37 immunoconjugate (e.g., IMGN529). Typically, no change or a decrease of at least 1.5-fold to 500-fold, 2-fold to 500-fold, 3-fold to 400-fold, 4-fold to 300-fold, 1.5-fold to 250-fold, 2-fold to 250-fold, 1.5-fold to 100-fold, or 2-fold to 100-fold in expression in at least one of the genes than the expression level of a reference gene indicates that a patient is likely to respond to or be sensitive to treatment with an anti-CD37 immunoconjugate (e.g., IMGN529).

TABLE 7

Genes correlated with sensitivity to an anti-CD37 immunoconjugate

| Cancer type | Gene (Accession No.) |
|---|---|
| Absence Of An Increased Expression Level Correlates to Sensitivity to CD37 Binding Agent | |
| GCB DLBCL | CD44 (UniProtKB P16070, SEQ ID NO: 23), VIM (UniProtKB P08670, SEQ ID NO: 24), ANXA2 (UniProtKB P07355, SEQ ID NO: 25), BCL2 (UniProtKB P10415, SEQ ID NO: 26), ANXA2P1 (UniProtKB A6NMY6, SEQ ID NO: 27), HSP90B1 (UniProtKB P08238, SEQ ID NO: 28), NFKBIZ (UniprotKB Q9BYH8, SEQ ID NO: 29), CDK6 (UniProtKB Q00534, SEQ ID NO: 30), BIRC5 (UniProtKB O15392, SEQ ID NO: 31) |
| ABC DLBCL | HSPA1B (UniProtKB P0DMV9, SEQ ID NO: 32), HSP90AA1 (UniProtKB P07900, SEQ ID NO: 33), CADM1 (UniProtKB Q9BY67, SEQ ID NO: 34), CD86 (UniProtKB P42081, SEQ ID NO: 35), TUBB2A (UniProtKB Q13885, SEQ ID NO: 36), TUBG1 (UniProtKB P23258, SEQ ID NO: 37), NOTCH1 (UniProtKB P46531, SEQ ID NO: 38) |
| ABC and GCB DLBCL | HEBP1 (UniProtKB Q9NRV9, SEQ ID NO: 39), PHB (UniProtKB P35232, SEQ ID NO: 40), PSME3 (UniProtKB P61289, SEQ ID NO: 41), RNU6-15 (NCBI RefSeq NR_028372.1, SEQ ID NO: 42), RPL13 (UniProt P26373, SEQ ID NO: 43) |
| Increased Expression Level Correlates to Sensitive to CD37 Binding Agent | |
| GCB DLBCL | BASP1 (UniProtKB P80723, SEQ ID NO: 44), CXCR5 (UniProtKB P32302, SEQ ID NO: 45), BIK (UniProtKB Q13323, SEQ ID NO: 46), LY86 (UniProtKB O95711, SEQ ID NO: 47), TLR10 (UniProtKB Q9BXR5, SEQ ID NO: 48), CD86 (UniProtKB P42081, SEQ ID NO: 35), LCK (UniProtKB P06239, SEQ ID NO: 49), CD22 (UniProtKB P20273, SEQ ID NO: 50), PTPN22 (UniProtKB Q9Y2R2, SEQ ID NO: 51), BCL6 (UniProtKB P41182, SEQ ID NO: 52), PIK3IP1 (UniProtKB Q96FE7, SEQ ID NO: 53), CDKN2A (UniProtKB P42771, SEQ ID NO: 54) |
| ABC DLBCL | AFF3 (UniProtKB P51826, SEQ ID NO: 55), PIM1 (UniProtKB P11309, SEQ ID NO: 56), MGMT (UniProtKB P16455, SEQ ID NO: 57), PDE4B (UniProtKB Q07343, SEQ ID NO: 58), NFKBIE (UniProtKB O00221, SEQ ID NO: 59), SYK (UniProtKB P43405, SEQ ID NO: 60), FOXO1 (UniProtKB Q9R1E0, SEQ ID NO: 61) |
| ABC and GCB DLBCL | CD37 (NCBI RefSeq NP_001765.1, SEQ ID NO: 1), CD79A (UniProtKB P11912, SEQ ID NO: 62), CHI3L2 (UniProtKB Q15782, SEQ ID NO: 63), FAM117B (UniProtKB Q6P1L5, SEQ ID NO: 64), LPAR5 (UniProtKB Q9H1C0, SEQ ID NO: 65), NFATC1 (UniProtKB O95644, SEQ ID NO: 66), PTPN22 (UniProtKB Q9Y2R2, SEQ ID NO: 67), RBM38 (UniProtKB Q9H0Z9, SEQ ID NO: 68), SGPP1 (UniProtKB Q9BX95, SEQ ID NO: 69), SLC6A16 (UniProtKB Q9GZN6, SEQ ID NO: 70) |

Nucleotide sequences of the genes or sequences of the proteins encoded by the genes listed in Table 7 are provided below.

CD44
(UniProtKB P16070, SEQ ID NO: 23)
MDKFWWHAAWGLCLVPLSLAQIDLNITCRFAGVFHVEKNGRYSISRTEAADLCKAFNSTLP

TMAQMEKALSIGFETCRYGFIEGHVVIPRIHPNSICAANNTGVYILTSNTSQYDTYCFNAS

APPEEDCTSVIDLPNAFDGPITITIVNRDGTRYVQKGEYRTNPEDIYPSNPTDDDVSSGSS

SERSSTSGGYIFYTFSTVHPIPDEDSPWITDSTDRIPATTLMSTSATATETATKRQETWDW

-continued

```
FSWLFLPSESKNHLHITTQMAGTSSNTISAGWEPNEENEDERDRHLSFSGSGIDDDEDFIS

STISTTPRAFDHTKQNQDWTONNPSHSNPEVLLQTTTRMTDVDRNGTTAYEGNWNPEAHPP

LIHHEHHEEEETPHSTSTIQATPSSTTEETATQKEQWFGNRWHEGYRQTPKEDSHSTIGTA

AASAHTSHPMQGRTTPSPEDSSWTDFFNPISHPMGRGHQAGRRMDMDSSHSITLQPTANPN

TGLVEDLDRTGPLSMITQQSNSQSFSTSHEGLEEDKDHPITSTLTSSNRNDVTGGRRDPNH

SEGSTILLEGYISHYPHTKESRIFIPVISAKTGSFGVTAVTVGDSNSNVNRSLSGDQDTFH

PSGGSHITHGSESDGHSHGSQEGGANTTSGPIRTPQIPEWLIILASLLALALILAVCIAVN

SRRRCGQKKKLVINSGNGAVEDRKPSGLNGEASKSQEMVHLVNKESSETPDQFMTADETRN

LQNVDMKIGV
```

VIM
(UniProtKB P08670, SEQ ID NO: 24)
```
MSTRSVSSSYRRMFGGPGTASRPSSSRSYVTTSTRTYSLGSALRPSTSRSLYASSPGGV

YATRSSAVRLRSSVPGVRLLQDSVDFSLADAINTEFKNTRINEKVELQELNDRFANYIDK

VRFLEQQNKILLAELEQLKGQGKSRLGDLYEEEMRELRRQVDQLTNDKARVEVERDNLAE

DIMRLREKLQEEMLQREEAENTLQSFRQDVDNASLARLDLERKVESLQEEIAFLKKLHEE

EIQELQAQIQEQHVQIDVDVSKPDLTAALRDVRQQYESVAAKNLQEAEEWYKSKFADLSE

AANRNNDALRQAKQESTEYRRQVQSLTCEVDALKGTNESLERQMREMEENFAVEAANYQD

TIGRLQDEIQNMKEEMARHLREYQDLLNVKMALDIEIATYRKLLEGEESRISLPLPNFSS

LNLRETNLDSLPLVDTHSKRTLLIKTVETRDGQVINETSQHHDDLE
```

ANXA2
(UniProtKB P07355, SEQ ID NO: 25)
```
MSTVHEILCKLSLEGDHSTPPSAYGSVKAYTNFDAERDALNIETAIKTKGVDEVTIVNIL

TNRSNAQRQDIAFAYQRRTKKELASALKSALSGHLETVILGLLKTPAQYDASELKASMKG

LGTDEDSLIEIICSRTNQELQEINRVYKEMYKTDLEKDIISDTSGDFRKLMVALAKGRRA

EDGSVIDYELIDQDARDLYDAGVKRKGTDVPKWISIMTERSVPHLQKVFDRYKSYSPYDM

LESIRKEVKGDLENAFLNLVQCIQNKPLYFADRLYDSMKGKGTRDKVLIRIMVSRSEVDM

LKIRSEFKRKYGKSLYYYIQQDTKGDYQKALLYLCGGDD
```

BCL2
(UniProtKB P10415, SEQ ID NO: 26)
```
MAHAGRTGYDNREIVMKYIHYKLSQRGYEWDAGDVGAAPPGAAPAPGIFSSQPGHTPHPA

ASRDPVARTSPLQTPAAPGAAAGPALSPVPPVVHLTLRQAGDDFSRRYRRDFAEMSSQLH

LTPFTARGRFATVVEELFRDGVNWGRIVAFFEFGGVMCVESVNREMSPLVDNIALWMTEY

LNRHLHTTNIQDNGGWDAFVELYGPSMRPLFDFSWLSLKTLLSLALVGACITLGAYLGHK
```

ANXA2P1
(UniProtKB A6NMY6, SEQ ID NO: 27)
```
MSTVHEILCKLSLEGDHSTPPSAYGSVKAYTNFDAERDALNIETAIKTKGVDEVTIVNIV

TNRDNAQRQDIVFSYQRRTKKELASALKSALSGHLETVILGLLKTPAQYDASELKASMKG

LGTDEDSLIEIICSRTNQELQEINRVYKEMYKTDLEKDIISDTSGDFRKLMVALAKGRRA

EDGSVIDYELIDQDAQDLYDAGVKRKGTDVPKWISIMTERSVPHLQKVFDRYKSYSPYDM

LESIRKEVKGDLENAFLNLVQRIQNKPLYFADQLYDSMKGKGTRDKVLIRIMVSRSEVDM

LKIRSEFKRKYGKSLYYYIQQDTKGDYQKALLYLCGGDD
```

HSP90B1
(UniProtKB P08238, SEQ ID NO: 28)
```
MPEEVHHGEEEVETFAFQAEIAQLMSLIINTFYSNKEIFLRELISNASDALDKIRYESLT

DPSKLDSGKELKIDIIPNPQERTLTLVDTGIGMTKADLINNLGTIAKSGTKAFMEALQAG

ADISMIGQFGVGFYSAYLVAEKVVVITKHNDDEQYAWESSAGGSFTVRADHGEPIGRGTK
```

-continued

VILHLKEDQTEYLEERRVKEVVKKHSQFIGYPITLYLEKEREKEISDDEAEEEKGEKEEE

DKDDEEKPKIEDVGSDEEDDSGKDKKKKTKKIKEKYIDQEELNKTKPIWTRNPDDITQEE

YGEFYKSLTNDWEDHLAVKHFSVEGQLEFRALLFIPRRAPFDLFENKKKKNNIKLYVRRV

FIMDSCDELIPEYLNFIRGVVDSEDLPLNISREMLQQSKILKVIRKNIVKKCLELFSELA

EDKENYKKFYEAFSKNLKLGIHEDSTNRRRLSELLRYHTSQSGDEMTSLSEYVSRMKETQ

KSIYYITGESKEQVANSAFVERVRKRGFEVVYMTEPIDEYCVQQLKEFDGKSLVSVTKEG

LELPEDEEEKKKMEESKAKFENLCKLMKEILDKKVEKVTISNRLVSSPCCIVISTYGWTA

NMERIMKAQALRDNSTMGYMMAKKHLEINPDHPIVETLRQKAEADKNDKAVKDLVVLLFE

TALLSSGFSLEDPQTHSNRIYRMIKLGLGIDEDEVAAEEPNAAVPDEIPPLEGDEDASRM

EEVD

NFKBIZ
(UniprotKB Q9BYH8, SEQ ID NO: 29)
MIVDKLLDDSRGGEGLRDAAGGCGLMTSPLNLSYFYGASPPAAAPGACDASCSVLGPSAP

GSPGSDSSDFSSASSVSSCGAVESRSRGGARAERQPVEPHMGVGRQQRGPFQGVRVKNSV

KELLLHIRSHKQKASGQAVDDFKTQGVNIEQFRELKNTVSYSGKRKGPDSLSDGPACKRP

ALLHSQFLTPPQTPTPGESMEDVHLNEPKQESSADLLQNIINIKNECSPVSLNTVQVSWL

NPVVVPQSSPAEQCQDFHGGQVFSPPQKCQPFQVRGSQQMIDQASLYQYSPQNQHVEQQP

HYTHKPTLEYSPFPIPPQSPAYEPNLFDGPESQFCPNQSLVSLLGDQRESENIANPMQTS

SSVQQQNDAHLHSFSMMPSSACEAMVGHEMASDSSNTSLPFSNMGNPMNTTQLGKSLFQW

QVEQEESKLANISQDQFLSKDADGDTFLHIAVAQGRRALSYVLARKMNALHMLDIKEHNG

QSAFQVAVAANQHLIVQDLVNIGAQVNTTDCWGRTPLHVCAEKGHSQVLQAIQKGAVGSN

QFVDLEATNYDGLTPLHCAVIAHNAVVHELQRNQQPHSPEVQELLLKNKSLVDTIKCLIQ

MGAAVEAKDRKSGRTALHLAAEEANLELIRLFLELPSCLSFVNAKAYNGNTALHVAASLQ

YRLTQLDAVRLLMRKGADPSTRNLENEQPVHLVPDGPVGEQIRRILKGKSIQQRAPPY

CDK6
(UniProtKB Q00534, SEQ ID NO: 30)
MEKDGLCRADQQYECVAEIGEGAYGKVFKARDLKNGGRFVALKRVRVQTGEEGMPLSTIR

EVAVLRHLETFEHPNVVRLFDVCTVSRTDRETKLTLVFEHVDQDLTTYLDKVPEPGVPTE

TIKDMMFQLLRGLDFLHSHRVVHRDLKPQNILVTSSGQIKLADFGLARIYSFQMALTSVV

VTLWYRAPEVLLQSSYATPVDLWSVGCIFAEMFRRKPLFRGSSDVDQLGKILDVIGLPGE

EDWPRDVALPRQAFHSKSAQPIEKFVTDIDELGKDLLLKCLTFNPAKRISAYSALSHPYF

QDLERCKENLDSHLPPSQNTSELNTA

BIRC5
(UniProtKB O15392, SEQ ID NO: 31)
MGAPTLPPAWQPFLKDHRISTFKNWPFLEGCACTPERMAEAGFIHCPTENEPDLAQCFFC

FKELEGWEPDDDPIEEHKKHSSGCAFLSVKKQFEELTLGEFLKLDRERAKNKIAKETNNK

KKEFEETAKKVRRAIEQLAAMD

HSPA1B
(UniProtKB P0DMV9, SEQ ID NO: 32)
MAKAAAIGIDLGTTYSCVGVFQHGKVEIIANDQGNRTTPSYVAFTDTERLIGDAAKNQVA

LNPQNTVFDAKRLIGRKFGDPVVQSDMKHWPFQVINDGDKPKVQVSYKGETKAFYPEEIS

SMVLTKMKEIAEAYLGYPVTNAVITVPAYFNDSQRQATKDAGVIAGLNVLRIINEPTAAA

IAYGLDRTGKGERNVLIFDLGGGTFDVSILTIDDGIFEVKATAGDTHLGGEDFDNRLVNH

FVEEFKRKHKKDISQNKRAVRRLRTACERAKRTLSSSTQASLEIDSLFEGIDFYTSITRA

-continued

RFEELCSDLFRSTLEPVEKALRDAKLDKAQIHDLVLVGGSTRIPKVQKLLQDFFNGRDLN

KSINPDEAVAYGAAVQAAILMGDKSENVQDLLLLDVAPLSLGLETAGGVMTALIKRNSTI

PTKQTQIFTTYSDNQPGVLIQVYEGERAMTKDNNLLGRFELSGIPPAPRGVPQIEVTFDI

DANGILNVTATDKSTGKANKITITNDKGRLSKEEIERMVQEAEKYKAEDEVQRERVSAKN

ALESYAFNMKSAVEDEGLKGKISEADKKKVLDKCQEVISWLDANTLAEKDEFEHKRKELE

QVCNPIISGLYQGAGGPGPGGFGAQGPKGGSGSGPTIEEVD

HSP90AA1
                                          (UniProtKB P07900, SEQ ID NO: 33)
MPEETQTQDQPMEEEEVETFAFQAEIAQLMSLIINTFYSNKEIFLRELISNSSDALDKIR

YESLTDPSKLDSGKELHINLIPNKQDRTLTIVDTGIGMTKADLINNLGTIAKSGTKAFME

ALQAGADISMIGQFGVGFYSAYLVAEKVTVITKHNDDEQYAWESSAGGSFTVRTDTGEPM

GRGTKVILHLKEDQTEYLEERRIKEIVKKHSQFIGYPITLFVEKERDKEVSDDEAEEKED

KEEEKEKEEKESEDKPEIEDVGSDEEEEKKDGDKKKKKKIKEKYIDQEELNKTKPIWTRN

PDDITNEEYGEFYKSLTNDWEDHLAVKHFSVEGQLEFRALLFVPRRAPFDLFENRKKKNN

IKLYVRRVFIMDNCEELIPEYLNFIRGVVDSEDLPLNISREMLQQSKILKVIRKNLVKKC

LELFTELAEDKENYKKFYEQFSKNIKLGIHEDSQNRKKLSELLRYYTSASGDEMVSLKDY

CTRMKENQKHIYYITGETKDQVANSAFVERLRKHGLEVIYMIEPIDEYCVQQLKEFEGKT

LVSVIKEGLELPEDEEEKKKQEEKKTKFENLCKIMKDILEKKVEKVVVSNRLVISPCCIV

TSTYGWTANMERIMKAQALRDNSTMGYMAAKKHLEINPDHSIIETLRQKAEADKNDKSVK

DLVILLYETALLSSGFSLEDPQTHANRIYRMIKLGLGIDEDDPTADDTSAAVTEEMPPLE

GDDDTSRMEEVD

CADM1
                                          (UniProtKB Q9BY67, SEQ ID NO: 34)
MASVVLPSGSQCAAAAAAAAPPGLRLRLLLLLFSAAALIPTGDGQNLFTKDVTVIEGEVA

TISCQVNKSDDSVIQLLNPNRQTIYFRDFRPLKDSRFQLLNFSSSELKVSLTNVSISDEG

RYFCQLYTDPPQESYTTITVLVPPRNLMIDIQKDTAVEGEEIEVNCTAMASKPATTIRWF

KGNTELKGKSEVEEWSDMYTVTSQLMLKVHKEDDGVPVICQVEHPAVTGNLQTQRYLEVQ

YKPQVHIQMTYPLQGLTREGDALELTCEAIGKPQPVMVTWVRVDDEMPQHAVLSGPNLFI

NNLNKTDNGTYRCEASNIVGKAHSDYMLYVYDPPTTIPPPTITTITTITTITTILTIITD

SRAGEEGSIRAVDHAVIGGVVAVVVFAMLCLLIILGRYFARHKGTYFTHEAKGADDAADA

DTAIINAEGGQNNSEEKKEYFI

CD86
                                          (UniProtKB P42081, SEQ ID NO: 35)
MDPQCTMGLSNILFVMAFLLSGAAPLKIQAYFNETADLPCQFANSQNQSLSELVVFWQDQ

ENLVLNEVYLGKEKFDSVHSKYMGRTSFDSDSWILRLHNLQIKDKGLYQCIIHHKKPTGM

IRIHQMNSELSVLANFSQPEIVPISNITENVYINLTCSSIHGYPEPKKMSVLLRTKNSTI

EYDGVMQKSQDNVTELYDVSISLSVSFPDVTSNMTIFCILETDKTRLLSSPFSIELEDPQ

PPPDHIPWITAVLPTVIICVMVFCLILWKWKKKKRPRNSYKCGTNTMEREESEQTKKREK

IHIPERSDEAQRVFKSSKTSSCDKSDTCF

TUBB2A
                                          (UniProtKB Q13885, SEQ ID NO: 36)
MREIVHIQAGQCGNQIGAKFWEVISDEHGIDPTGSYHGDSDLQLERINVYYNEAAGNKYV

PRAILVDLEPGTMDSVRSGPFGQIFRPDNFVFGQSGAGNNWAKGHYTEGAELVDSVLDVV

RKESESCDCLQGFQLTHSLGGGIGSGMGILLISKIREEYPDRIMNTFSVMPSPKVSDTVV

EPYNATLSVHQLVENTDETYSIDNEALYDICFRILKLITPTYGDLNHLVSATMSGVTTCL

-continued

RFPGQLNADLRKLAVNMVPFPRLHFFMPGFAPLTSRGSQQYRALTVPELTQQMFDSKNMM

AACDPRHGRYLTVAAIFRGRMSMKEVDEQMLNVQNKNSSYFVEWIPNNVKTAVCDIPPRG

LKMSATFIGNSTAIQELFKRISEQFTAMFRRKAFLHWYTGEGMDEMEFTEAESNMNDLVS

EYQQYQDATADEQGEFEEEEGEDEA

TUBG1

(UniProtKB P23258, SEQ ID NO: 37)

MPREIITLQLGQCGNQIGFEFWKQLCAEHGISPEGIVEEFATEGTDRKDVFFYQADDEHY

IPRAVLLDLEPRVIHSILNSPYAKLYNPENIYLSEHGGGAGNNWASGFSQGEKIHEDIFD

IIDREADGSDSLEGFVLCHSIAGGTGSGLGSYLLERLNDRYPKKLVQTYSVFPNQDEMSD

VVVQPYNSLLTLKRLTQNADCVVVLDNTALNRIATDRLHIQNPSFSQINQLVSTIMSAST

TTLRYPGYMNNDLIGLIASLIPTPRLHFLMTGYTPLITDQSVASVRKTTVLDVMRRLLQP

KNVMVSTGRDRQTNHCYIAILNIIQGEVDPTQVHKSLQRIRERKLANFIPWGPASIQVAL

SRKSPYLPSAHRVSGLMMANHTSISSLFERTCRQYDKLRKREAFLEQFRKEDMFKDNFDE

MDTSREIVQQLIDEYHAATRPDYISWGTQEQ

NOTCH1

(UniProtKB P46531, SEQ ID NO: 38)

MPPLLAPLLCLALLPALAARGPRCSQPGETCLNGGKCEAANGTEACVCGGAFVGPRCQDP

NPCLSTPCKNAGTCHVVDRRGVADYACSCALGFSGPLCLTPLDNACLINPCRNGGICDLL

TLTEYKCRCPPGWSGKSCQQADPCASNPCANGGQCLPFEASYICHCPPSFHGPTCRQDVN

ECGQKPGLCRHGGTCHNEVGSYRCVCRATHTGPNCERPYVPCSPSPCQNGGTCRPTGDVT

HECACLPGFTGQNCEENIDDCPGNNCKNGGACVDGVNTYNCRCPPEWTGQYCTEDVDECQ

LMPNACQNGGTCHNTHGGYNCVCVNGWTGEDCSENIDDCASAACFHGATCHDRVASFYCE

CPHGRTGLLCHLNDACISNPCNEGSNCDTNPVNGKAICTCPSGYTGPACSQDVDECSLGA

NPCEHAGKCINTLGSFECQCLQGYTGPRCEIDVNECVSNPCQNDATCLDQIGEFQCICMP

GYEGVHCEVNTDECASSPCLHNGRCLDKINEFQCECPTGFTGHLCQYDVDECASTPCKNG

AKCLDGPNTYTCVCTEGYTGTHCEVDIDECDPDPCHYGSCKDGVATFTCLCRPGYIGHHC

ETNINECSSQPCRHGGTCQDRDNAYLCFCLKGTTGPNCEINLDDCASSPCDSGTCLDKID

GYECACEPGYTGSMCNINIDECAGNPCHNGGICEDGINGFTCRCPEGYHDPTCLSEVNEC

NSNPCVHGACRDSLNGYKCDCDPGWSGINCDINNNECESNPCVNGGICKDMTSGYVCTCR

EGFSGPNCQTNINECASNPCLNQGTCIDDVAGYKCNCLLPYTGATCEVVLAPCAPSPCRN

GGECRQSEDYESFSCVCPTGWQGQTCEVDINECVLSPCRHGASCQNTHGGYRCHCQAGYS

GRNCETDIDDCRPNPCHNGGSCTDGINTAFCDCLPGFRGTFCEEDINECASDPCRNGANC

TDCVDSYTCTCPAGFSGIHCENNTPDCTESSCFNGGTCVDGINSFTCLCPPGFTGSYCQH

DVNECDSQPCLHGGICQDGCGSYRCTCPQGYTGPNCQNLVHWCDSSPCKNGGKCWQTHIQ

YRCECPSGWTGLYCDVPSVSCEVAAQRQGVDVARLCQHGGLCVDAGNTHHCRCQAGYTGS

YCEDLVDECSPSPCQNGATCTDYLGGYSCKCVAGYHGVNCSEEIDECLSHPCQNGGTCLD

LPNTYKCSCPRGTQGVHCEINVDDCNPPVDPVSRSPKCFNNGTCVDQVGGYSCTCPPGFV

GERCEGDVNECLSNPCDARGTQNCVQRVNDFHCECRAGHTGRRCESVINGCKGKPCKNGG

TCAVASNTARGFICKCPAGFEGATCENDARTCGSLRCLNGGTCISGPRSPTCLCLGPFTG

PECQFPASSPCLGGNPCYNQGTCEPTSESPFYRCLCPAKFNGLLCHILDYSFGGGAGRDI

PPPLIEEACELPECQEDAGNKVCSLQCNNHACGWDGGDCSLNFNDPWKNCTQSLQCWKYF

SDGHCDSQCNSAGCLFDGFDCQRAEGQCNPLYDQYCKDHFSDGHCDQGCNSAECEWDGLD

-continued

```
CAEHVPERLAAGTLVVVVLMPPEQLRNSSFHFLRELSRVLHTNVVFKRDAHGQQMIFPYY

GREEELRKHPIKRAAEGWAAPDALLGQVKASLLPGGSEGGRRRRELDPMDVRGSIVYLEI

DNRQCVQASSQCFQSATDVAAFLGALASLGSLNIPYKIEAVQSETVEPPPPAQLHFMYVA

AAAFVLLFFVGCGVLLSRKRRRQHGQLWFPEGFKVSEASKKKRREPLGEDSVGLKPLKNA

SDGALMDDNQNEWGDEDLETKKFRFEEPVVLPDLDDQTDHRQWTQQHLDAADLRMSAMAP

TPPQGEVDADCMDVNVRGPDGFTPLMIASCSGGGLETGNSEEEEDAPAVISDFIYQGASL

HNQTDRTGETALHLAARYSRSDAAKRLLEASADANIQDNMGRTPLHAAVSADAQGVFQIL

IRNRATDLDARMHDGTTPLILAARLAVEGMLEDLINSHADVNAVDDLGKSALHWAAAVNN

VDAAVVLLKNGANKDMQNNREETPLFLAAREGSYETAKVLLDHFANRDITDHMDRLPRDI

AQERMHHDIVRLLDEYNLVRSPQLHGAPLGGTPTLSPPLCSPNGYLGSLKPGVQGKKVRK

PSSKGLACGSKEAKDLKARRKKSQDGKGCLLDSSGMLSPVDSLESPHGYLSDVASPPLLP

SPFQQSPSVPLNHLPGMPDTHLGIGHLNVAAKPEMAALGGGGRLAFETGPPRLSHLPVAS

GTSTVLGSSSGGALNFTVGGSTSLNGQCEWLSRLQSGMVPNQYNPLRGSVAPGPLSTQAP

SLQHGMVGPLHSSLAASALSQMMSYQGLPSTRLATQPHLVQTQQVQPQNLQMQQQNLQPA

NIQQQQSLQPPPPPPQPHLGVSSAASGHLGRSFLSGEPSQADVQPLGPSSLAVHTILPQE

SPALPTSLPSSLVPPVTAAQFLTPPSQHSYSSPVDNTPSHQLQVPEHPFLTPSPESPDQW

SSSSPHSNVSDWSEGVSSPPTSMQSQIARIPEAFK

HEBP1
                           (UniProtKB Q9NRV9, SEQ ID NO: 39)
MLGMIKNSLFGSVETWPWQVLSKGDKEEVAYEERACEGGKFATVEVTDKPVDEALREAMP

KVAKYAGGTNDKGIGMGMTVPISFAVFPNEDGSLQKKLKVWFRIPNQFQSDPPAPSDKSV

KIEEREGITVYSMQFGGYAKEADYVAQATRLRAALEGTATYRGDIYFCTGYDPPMKPYGR

RNEIWLLKT

PHB
                           (UniProtKB P35232, SEQ ID NO: 40)
MAAKVFESIGKFGLALAVAGGVVNSALYNVDAGHRAVIFDRFRGVQDIVVGEGTHFLIPW

VQKPIIFDCRSRPRNVPVITGSKDLQNVNITLRILFRPVASQLPRIFTSIGEDYDERVLP

SITTEILKSVVARFDAGELITQRELVSRQVSDDLTERAATFGLILDDVSLTHLTFGKEFT

EAVEAKQVAQQEAERARFVVEKAEQQKKAAIISAEGDSKAAELIANSLATAGDGLIELRK

LEAAEDIAYQLSRSRNITYLPAGQSVLLQLPQ

PSME3
                           (UniProtKB P61289, SEQ ID NO: 41)
MASLLKVDQEVKLKVDSFRERITSEAEDLVANFFPKKLLELDSFLKEPILNIHDLTQIHS

DMNLPVPDPILLTNSHDGLDGPTYKKRRLDECEEAFQGTKVFVMPNGMLKSNQQLVDIIE

KVKPEIRLLIEKCNTVKMWVQLLIPRIEDGNNFGVSIQEETVAELRTVESEAASYLDQIS

RYYITRAKLVSKIAKYPHVEDYRRTVTEIDEKEYISLRLIISELRNQYVTLHDMILKNIE

KIKRPRSSNAETLY

RNU6-15
                           (NCBI RefSeq NR_028372.1, SEQ ID NO: 42)
GTGCTCACTT CGGCAGCACA TATACTAAAA TTGGAACGAT ACAGAGAAGA TTAGCATGGC

CCCTGCGCAA GGATGACACG CAAATTCGTG AAGCATTCCA TATTTTT

RPL13
                           (UniProt P26373, SEQ ID NO: 43)
MAPSRNGMVLKPHFHKDWQRRVATWFNQPARKIRRRKARQAKARRIAPRPASGPIRPIVR

CPTVRYHTKVRAGRGFSLEELRVAGIHKKVARTIGISVDPRRRNKSTESLQANVQRLKEY
```

```
RSKLILFPRKPSAPKKGDSSAEELKLATQLTGPVMPVRNVYKKEKARVITEEEKNFKAFA

SLRMARANARLFGIRAKRAKEAAEQDVEKKK

BASP1
                                        (UniProtKB P80723, SEQ ID NO: 44)
MGGKLSKKKKGYNVNDEKAKEKDKKAEGAATEEEGTPKESEPQAAAEPAEAKEGKEKPDQ

DAEGKAEEKEGEKDAAAAKEEAPKAEPEKTEGAAEAKAEPPKAPEQEQAAPGPAAGGEAP

KAAEAAAAPAESAAPAAGEEPSKEEGEPKKTEAPAAPAAQETKSDGAPASDSKPGSSEAA

PSSKETPAATEAPSSTPKAQGPAASAEEPKPVEAPAANSDQTVTVKE

CXCR5
                                        (UniProtKB P32302, SEQ ID NO: 45)
MNYPLTLEMDLENLEDLFWELDRLDNYNDTSLVENHLCPATEGPLMASFKAVFVPVAYSL

IFLLGVIGNVLVLVILERHRQTRSSTETFLFHLAVADLLLVFILPFAVAEGSVGWVLGTF

LCKTVIALHKVNFYCSSLLLACIAVDRYLAIVHAVHAYRHRRLLSIHITCGTIWLVGFLL

ALPEILFAKVSQGHHNNSLPRCTFSQENQAETHAWFTSRFLYHVAGFLLPMLVMGWCYVG

VVHRLRQAQRRPQRQKAVRVAILVTSIFFLCWSPYHIVIFLDTLARLKAVDNICKLNGSL

PVAITMCEFLGLAHCCLNPMLYTFAGVKFRSDLSRLLTKLGCTGPASLCQLFPSWRRSSL

SESENATSLTTF

BIK
                                        (UniProtKB Q13323, SEQ ID NO: 46)
MSEVRPLSRDILMETLLYEQLLEPPTMEVLGMTDSEEDLDPMEDFDSLECMEGSDALALR

LACIGDEMDVSLRAPRLAQLSEVAMHSLGLAFIYDQTEDIRDVLRSFMDGFTTLKENIMR

FWRSPNPGSWVSCEQVLLALLLLLALLLPLLSGGLHLLLK

LY86
                                        (UniProtKB O95711, SEQ ID NO: 47)
MKGFTATLFLWTLIFPSCSGGGGGKAWPTHVVCSDSGLEVLYQSCDPLQDFGFSVEKCSK

QLKSNININRFGIILREDIKELFLDLALMSQGSSVLNFSYPICEAALPKFSFCGRRKGEQI

YYAGPVNNPEFTIPQGEYQVLLELYTEKRSTVACANATIMCS

TLR10
                                        (UniProtKB Q9BXR5, SEQ ID NO: 48)
MRLIRNIYIFCSIVMTAEGDAPELPEERELMINCSNMSLRKVPADLTPATTILDLSYNLL

FQLQSSDFHSVSKLRVLILCHNRIQQLDLKTFEFNKELRYLDLSNNRLKSVTWYLLAGLR

YLDLSFNDFDTMPICEEAGNMSHLEILGLSGAKIQKSDFQKIAHLHLNTVFLGFRTLPHY

EEGSLPILNTTKLHIVLPMDTNFWVLLRDGIKTSKILEMTNIDGKSQFVSYEMQRNLSLE

NAKTSVLLLNKVDLLWDDLFLILQFVWHTSVEHFQIRNVTFGGKAYLDHNSFDYSNTVMR

TIKLEHVHFRVFYIQQDKIYLLLTKMDIENLTISNAQMPHMLFPNYPTKFQYLNFANNIL

TDELFKRTIQLPHLKTLILNGNKLETLSLVSCFANNTPLEHDLSQNLLQHKNDENCSWP

ETVVNMNLSYNKLSDSVFRCLPKSIQILDLNNNQIQTVPKETIHLMALRELNIAFNFLTD

LPGCSHFSRLSVLNIEMNFILSPSLDFVQSCQEVKTLNAGRNPFRCTCELKNFIQLETYS

EVMMVGWSDSYTCEYPLNLRGTRLKDVHLHELSCNTALLIVTIVVIMLVLGLAVAFCCLH

FDLPWYLRMLGQCTQTWHRVRKTTQEQLKRNVRFHAFISYSEHDSLWVKNELIPNLEKED

GSILICLYESYFDPGKSISENIVSFIEKSYKSIFVLSPNFVQNEWCHYEFYFAHHNLFHE

NSDHIILILLEPIPFYCIPTRYHKLKALLEKKAYLEWPKDRRKCGLFWANLRAAINVNVL

ATREMYELQTFTELNEESRGSTISLMRTDCL
```

-continued

LCK
(UniProtKB P06239, SEQ ID NO: 49)
MGCGCSSHPEDDWMENIDVCENCHYPIVPLDKGTLLIRNGSEVRDPLVTYEGSNPPASP

LQDNLVIALHSYEPSHDGDLGFEKGEQLRILEQSGEWWKAQSLTTGQEGFIPFNFVAKAN

SLEPEPWFFKNLSRKDAERQLLAPGNTHGSFLIRESESTAGSFSLSVRDFDQNQGEVVKH

YKIRNLDNGGFYISPRITFPGLHELVRHYTNASDGLCTRLSRPCQTQKPQKPWWEDEWEV

PRETLKLVERLGAGQFGEVWMGYYNGHTKVAVKSLKQGSMSPDAFLAEANLMKQLQHQRL

VRLYAVVTQEPIYIITEYMENGSLVDFLKTPSGIKLTINKLLDMAAQIAEGMAFIEERNY

IHRDLRAANILVSDTLSCKIADFGLARLIEDNEYTAREGAKFPIKWTAPEAINYGTFT1K

SDVWSFGILLTEIVTHGRIPYPGMTNPEVIQNLERGYRMVRPDNCPEELYQLMRLCWKER

PEDRPTFDYLRSVLEDFFTATEGQYQPQP

CD22
(UniProtKB P20273, SEQ ID NO: 50)
MHLLGPWLLLLVLEYLAFSDSSKWVFEHPETLYAWEGACVWIPCTYRALDGDLESFILFH

NPEYNKNTSKFDGTRLYESTKDGKVPSEQKRVQFLGDKNKNCTLSIHPVHLNDSGQLGLR

MESKTEKWMERIHLNVSERPFPPHIQLPPEIQESQEVTLICLLNFSCYGYPIQLWLLEG

VPMRQAAVTSTSLTIKSVFTRSELKFSPQWSHHGKIVTCQLQDADGKFLSNDTVQLNVKH

TPKLEIKVTPSDAIVREGDSVTMTCEVSSSNPEYTTVSWLKDGTSLKKQNTFTLNLREVT

KDQSGKYCCQVSNDVGPGRSEEVFLQVQYAPEPSTVQILHSPAVEGSQVEFLCMSLANPL

PTNYTWYHNGKEMQGRTEEKVHIPKILPWHAGTYSCVAENILGTGQRGPGAELDVQYPPK

KVITVIQNPMPIREGDTVTLSCNYNSSNPSVTRYEWKPHGAWEEPSLGVLKIQNVGWDNT

TIACAACNSWCSWASPVALNVQYAPRDVRVRKIKPLSEIHSGNSVSLQCDFSSSHPKEVQ

FFWEKNGRLLGKESQLNFDSISPEDAGSYSCWVNNSIGQTASKAWTLEVLYAPRRLRVSM

SPGDQVMEGKSATLTCESDANPPVSHYTWFDWNNQSLPYHSQKLRLEPVKVQHSGAYWCQ

GTNSVGKGRSPLSTLTVYYSPETIGRRVAVGLGSCLAILILAICGLKLQRRWKRTQSQQG

LQENSSGQSFFVRNKKVRRAPLSEGPHSLGCYNPMMEDGISYTTLRFPEMNIPRTGDAES

SEMQRPPPDCDDTVTYSALHKRQVGDYENVIPDFPEDEGIHYSELIQFGVGERPQAQENV

DYVILKH

PTPN22
(UniProtKB Q9Y2R2, SEQ ID NO: 51)
MDQREILQKFLDEAQSKKITKEEFANEFLKLKRQSTKYKADKTYPTTVAEKPKNIKKNRY

KDILPYDYSRVELSLITSDEDSSYINANFIKGVYGPKAYIATQGPLSTTLLDFWRMIWEY

SVLIIVMACMEYEMGKKKCERYWAEPGEMQLEFGPFSVSCEAEKRKSDYIIRTLKVKFNS

ETRTIYQFHYKNWPDHDVPSSIDPILELIWDVRCYQEDDSVPICIHCSAGCGRTGVICAI

DYTWMLLKDGIIPENFSVFSLIREMRTQRPSLVQTQEQYELVYNAVLELFKRQMDVIRDK

HSGTESQAKHCIPEKNHTLQADSYSPNLPKSTTKAAKMMNQQRTKMEIKESSSFDFRTSE

ISAKEELVLHPAKSSTSFDFLELNYSFDKNADTTMKWQTKAFPIVGEPLQKHQSLDLGSL

LFEGCSNSKPVNAAGRYFNSKVPITRTKSTPFELIQQRETKEVDSKENFSYLESQPHDSC

FVEMQAQKVMHVSSAELNYSLPYDSKHQIRNASNVKHHDSSALGVYSYIPLVENPYFSSW

PPSGTSSKMSLDLPEKQDGTVFPSSLLPTSSTSLFSYYNSHDSLSLNSPTNISSLLNQES

AVLATAPRIDDEIPPPLPVRTPESFIVVEEAGEFSPNVPKSLSSAVKVKIGTSLEWGGTS

EPKKFDDSVILRPSKSVKLRSPKSELHQDRSSPPPPLPERTLESFFLADEDCMQAQSIET

YSTSYPDTMENSSSKQTLKTPGKSFTRSKSLKILRNMKKSICNSCPPNKPAESVQSNNS

SSFLNFGFANRFSKPKGPRNPPPTTNNI

BCL6

(UniProtKB P41182, SEQ ID NO: 52)
MASPADSCIQFTRHASDVLLNLNRLRSRDILTDVVIVVSREQFRAHKTVLMACSGLFYSI

FTDQLKCNLSVINLDPEINPEGFCILLDFMYTSRLNLREGNIMAVMATAMYLQMEHVVDT

CRKFIKASEAEMVSAIKPPREEFLNSRMLMPQDIMAYRGREVVENNLPLRSAPGCESRAF

APSLYSGLSTPPASYSMYSHLPVSSLLFSDEEFRDVRMPVANPFPKERALPCDSARPVPG

EYSRPTLEVSPNVCHSNIYSPKETIPEEARSDMHYSVAEGLKPAAPSARNAPYFPCDKAS

KEEERPSSEDEIALHFEPPNAPLNRKGLVSPQSPQKSDCQPNSPTESCSSKNACILQASG

SPPAKSPTDPKACNWKKYKFIVLNSLNQNAKPEGPEQAELGRLSPRAYTAPPACQPPMEP

ENLDLQSPTKLSASGEDSTIPQASRLNNIVNRSMTGSPRSSSESHSPLYMHPPKCTSCGS

QSPQHAEMCLHTAGPTFPEEMGETQSEYSDSSCENGAFFCNECDCRFSEEASLKRHTLQT

HSDKPYKCDRCQASFRYKGNLASHKTVHTGEKPYRCNICGAQFNRPANLKTHTRIHSGEK

PYKCETCGARFVQVAHLRAHVLIHTGEKPYPCEICGTRFRHLQTLKSHLRIHTGEKPYHC

EKCNLHFRHKSQLRLHLRQKHGAITNTKVQYRVSATDLPPELPKAC

PIK3IP1

(UniProtKB Q96FE7, SEQ ID NO: 53)
MLLAWVQAFLVSNMLLAEAYGSGGCFWDNGHLYREDQTSPAPGLRCLNWLDAQSGLASAP

VSGAGNHSYCRNPDEDPRGPWCYVSGEAGVPEKRPCEDLRCPETTSQALPAFTTEIQEAS

EGPGADEVQVFAPANALPARSEAAAVQPVIGISQRVRMNSKEKKDLGTLGYVLGITMMVI

IIAIGAGIILGYSYKRGKDLKEQHDQKVCEREMQRITLPLSAFTNPTCEIVDEKTVVVHT

SQTPVDPQEGTTPLMGQAGTPGA

CDKN2A (UniProtKB P42771, SEQ ID NO: 54)
MEPAAGSSMEPSADWLATAAARGRVEEVRALLEAGALPNAPNSYGRRPIQVMMMGSARVA

ELLLLHGAEPNCADPATLTRPVHDAAREGFLDTLVVLHRAGARLDVRDAWGRLPVDLAEE

LGHRDVARYLRAAAGGTRGSNHARIDAAEGPSDIPD

AFF3

(UniProtKB P51826, SEQ ID NO: 55)
MDSFDLALLQEWDLESLCVYEPDRNALRRKERERRNQETQQDDGTFNSSYSLFSEPYKTN

KGDELSNRIQNTLGNYDEMKDFLTDRSNQSHLVGVPKPGVPQTPVNKIDEHFVADSRAQN

QPSSICSTITSTPAAVPVQQSKRGTMGWQKAGHPPSDGQQRATQQGSLRTLLGDGVGRQQ

PRAKQVCNVEVGLQTQERPPAMAAKHSSSGHCVQNFPPSLASKPSLVQQKPTAYVRPMDG

QDQAPDESPKLKSSSETSVHCTSYRGVPASKPEPARAKAKLSKFSIPKQGEESRSGETNS

CVEEIIREMTWLPPLSAIQAPGKVEPTKFPFPNKDSQLVSSGHNNPKKGDAEPESPDSGT

SNTSMLEDDLKLSSDEEENEQQAAQRTALRALSDSAVVQQPNCRTSVPSSKGSSSSSSSG

SSSSSSDSESSSGSDSETESSSSESEGSKPPHFSSPEAEPASSNKWQLDKWLNKVNPHKP

PILIQNESHGSESNQYYNPVKEDVQDCGKVPDVCQPSLREKEIKSTCKEEQRPRTANKAP

GSKGVKQKSPPAAVAVAVSAAAPPPAVPCAPAENAPAPARRSAGKKPTRRTERTSAGDGA

NCHRPEEPAAADALGTSVVVPPEPTKTRPCGNNRASHRKELRSSVTCEKRRTRGLSRIVP

KSKEFIETESSSSSSSSDSDLESEQEEYPLSKAQTVAASASSGNDQRLKEAAANGGSGPR

APVGSINARTTSDIAKELEEQFYTLVPFGRNELLSPLKDSDEIRSLWVKIDLTLLSRIPE

HLPQEPGVLSAPATKDSESAPPSHTSDTPAEKALPKSKRKRKCDNEDDYREIKKSQGEKD

SSSRLATSTSNTLSANHCMMNINSVAIPINKNEKMLRSPISPLSDASKHKYTSEDLTSSS

RPNGNSLFTSASSSKKPKADSQLQPHGGDLTKAAHNNSENIPLHKSRPQTKPWSPGSNGH

-continued

RDCKRQKLVFDDMPRSADYFMQEAKRMKHKADAMVEKFGKALNYAEAALSFIECGNAMEQ

GPMESKSPYTMYSETVELIRYAMRLKTHSGPNATPEDKQLAALCYRCLALLYWRMFRLKR

DHAVKYSKALIDYFKNSSKAAQAPSPWGASGKSTGTPSPMSPNPSPASSVGSQGSLSNAS

ALSPSTIVSIPQRIHQMAANHVSITNSILHSYDYWEMADNLAKENREFFNDLDLLMGPVT

LHSSMEHLVQYSQQGLHWLRNSAHLS

PIM1
                                      (UniProtKB P11309, SEQ ID NO: 56)
MPHEPHEPLTPPFSALPDPAGAPSRRQSRQRPQLSSDSPSAFRASRSHSRNATRSHSHSH

SPRHSLRHSPGSGSCGSSSGHRPCADILEVGMLLSKINSLAHLRAAPCNDLHATKLAPGK

EKEPLESQYQVGPLLGSGGFGSVYSGIRVSDNLPVAIKHVEKDRISDWGELPNGTRVPME

VVLLKKVSSGFSGVIRLLDWFERPDSFVLILERPEPVQDLFDFITERGALQEELARSFFW

QVLEAVRHCHNCGVLHRDIKDENILIDLNRGELKLIDFGSGALLKDTVYTDFDGTRVYSP

PEWIRYHRYHGRSAAVWSLGILLYDMVCGDIPFEHDEEIIRGQVFFRQRVSSECQHLIRW

CLALRPSDRPTFEEIQNHPWMQDVLLPQETAEIHLHSLSPGPSK

MGMT
                                      (UniProtKB P16455, SEQ ID NO: 57)
MDKDCEMKRTTLDSPLGKLELSGCEQGLHEIKLLGKGTSAADAVEVPAPAAVLGGPEPLM

QCTAWLNAYFHQPEAIEEFPVPALHHPVFQQESFTRQVLWKLLKVVKFGEVISYQQLAAL

AGNPKAARAVGGAMRGNPVPILIPCHRVVCSSGAVGNYSGGLAVKEWLLAHEGHRLGKPG

LGGSSGLAGAWLKGAGATSGSPPAGRN

PDE4B
                                     (UniProtKB Q07343, SEQ ID NO: 58)
MKKSRSVMTVMADDNVKDYFECSLSKSYSSSSNTLGIDLWRGRRCCSGNLQLPPLSQRQS

ERARTPEGDGISRPTTLPLTTLPSIAITTVSQECFDVENGPSPGRSPLDPQASSSAGLVL

HATFPGHSQRRESFLYRSDSDYDLSPKAMSRNSSLPSEQHGDDLIVTPFAQVLASLRSVR

NNFTILTNLHGTSNKRSPAASQPPVSRVNPQEESYQKLAMETLEELDWCLDQLETIQTYR

SVSEMASNKFKRMLNRELTHLSEMSRSGNQVSEYISNTFLDKQNDVEIPSPTQKDREKKK

KQQLMTQISGVKKLMHSSSLNNTSISRFGVNTENEDHLAKELEDLNKWGLNIFNVAGYSH

NRPLTCIMYAIFQERDLLKTFRISSDTFITYMMTLEDHYHSDVAYHNSLHAADVAQSTHV

LLSTPALDAVFTDLEILAAIFAAAIHDVDHPGVSNQFLINTNSELALMYNDESVLENHHL

AVGFKLLQEEHCDIFMNLIKKQRQTLRKMVIDMVLATDMSKHMSLLADLKTMVETKKVTS

SGVLLLDNYTDRIQVLRNMVHCADLSNPTKSLELYRQWTDRIMEEFFQQGDKERERGMEI

SPMCDKHTASVEKSQVGFIDYIVHPLWETWADLVQPDAQDILDTLEDNRNWYQSMIPQSP

SPPLDEQNRDCQGLMEKFQFELTLDEEDSEGPEKEGEGHSYFSSTKTLCVIDPENRDSLG

ETDIDIATEDKSPVDT

NFKBIE
                                  (UniProtKB O00221, SEQ ID NO: 59)
MNQRRSESRPGNHRLQAYAEPGKGDSGGAGPLSGSARRGRGGGGAIRVRRPCWSGGAGRG

GGPAWAVRLPTVTAGWTWPALRTLSSLRAGPSEPHSPGRRPPRAGRPLCQADPQPGKAAR

RSLEPDPAQTGPRPARAAGMSEARKGPDEAEESQYDSGIESLRSLRSLPESTSAPASGPS

DGSPQPCTHPPGPVKEPQEKEDADGERADSTYGSSSLTYTLSLLGGPEAEDPAPRLPLPH

VGALSPQQLEALTYISEDGDTLVHLAVIHEAPAVLLCCLALLPQEVLDIQNNLYQTALHL

AVHLDQPGAVRALVLKGASRALQDRHGDTALHVACQRQHLACARCLLEGRPEPGRGTSHS

LDLQLQNWQGLACLHIATLQKNQPLMELLLRNGADIDVQEGTSGKTALHLAVETQERGLV

QFLLQAGAQVDARMLNGCTPLHLAAGRGLMGISSTLCKAGADSLLRNVEDETPQDLTEES

```
LVLLPFDDLKISGKLLLCTD

SYK
                                       (UniProtKB P43405, SEQ ID NO: 60)
MASSGMADSANHLPFFFGNITREEAEDYLVQGGMSDGLYLLRQSRNYLGGFALSVAHGRK

AHHYTIERELNGTYAIAGGRTHASPADLCHYHSQESDGLVCLLKKPFNRPQGVQPKTGPF

EDLKENLIREYVKQTWNLQGQALEQAIISQKPQLEKLIATTAHEKMPWFHGKISREESEQ

IVLIGSKTNGKFLIRARDNNGSYALCLLHEGKVLHYRIDKDKTGKLSIPEGKKFDTLWQL

VEHYSYKADGLLRVLTVPCQKIGTQGNVNFGGRPQLPGSHPATWSAGGIISRIKSYSFPK

PGHRKSSPAQGNRQESTVSFNPYEPELAPWAADKGPQREALPMDTEVYESPYADPEEIRP

KEVYLDRKLLTLEDKELGSGNFGTVKKGYYQMKKVVKTVAVKILKNEANDPALKDELLAE

ANVMQQLDNPYIVRMIGICEAESWMLVMEMAELGPLNKYLQQNRHVKDKNIIELVHQVSM

GMKYLEESNFVHRDLAARNVLLVTQHYAKISDFGLSKALRADENYYKAQTHGKWPVKWYA

PECINYYKFSSKSDVWSFGVLMWEAFSYGQKPYRGMKGSEVTAMLEKGERMGCPAGCPRE

MYDLMNLCWTYDVENRPGFAAVELRLRNYYYDVVN

FOXO1
                                       (UniProtKB Q9R1E0, SEQ ID NO: 61)
MAEAPQVVETDPDFEPLPRQRSCTWPLPRPEFNQSNSTTSSPAPSGGAAANPDAAASLAS

ASAVSTDFMSNLSLLEESEDFARAPGCVAVAAAAAASRGLCGDFQGPEAGCVHPAPPQPP

PTGPLSQPPPVPPSAAAAAGPLAGQPRKTSSSRRNAWGNLSYADLITKAIESSAEKRLTL

SQIYEWMVKSVPYFKDKGDSNSSAGWKNSIRHNLSLHSKFIRVQNEGTGKSSWWMLNPEG

GKSGKSPRRRAASMDNNSKFAKSRGRAAKKKASLQSGQEGPGDSPGSQFSKWPASPGSHS

NDDFDNWSTFRPRTSSNASTISGRLSPIMTEQDDLGDGDVHSLVYPPSAAKMASTLPSLS

EISNPENMENLLDNLNLLSSPTSLTVSTQSSPGSMMQQTPCYSFAPPNTSLNSPSPNYSK

YTYGQSSMSPLPQMPMQTLQDSKSSYGGLNQYNCAPGLLKELLTSDSPPHNDIMSPVDPG

VAQPNSRVLGQNVMMGPNSVMPAYGSQASHNKMMNPSSHTHPGHAQQTASVNGRTLPHVV

NTMPHISAMNRLTPVKTPLQVPLSHPMQMSALGSYSSVSSCNGYGRMGVLHQEKLPSDLD

GMFIERLDCDMESIIRNDLMDGDTLDFNFDNVLPNQSFPHSVKITTHSWVSG

CD79A
                                       (UniProtKB P11912, SEQ ID NO: 62)
MPGGPGVLQALPATIFLLFLLSAVYLGPGCQALWMHKVPASLMVSLGEDAHFQCPHNSSN

NANVTWWRVLHGNYTWPPEFLGPGEDPNGTLIIQNVNKSHGGIYVCRVQEGNESYQQSCG

TYLRVRQPPPRPFLDMGEGTKNRIITAEGIILLFCAVVPGTLLLFRKRWQNEKLGLDAGD

EYEDENLYEGLNLDDCSMYEDISRGLQGTYQDVGSLNIGDVQLEKP

CHI3L2
                                       (UniProtKB Q15782, SEQ ID NO: 63)
MGATTMDQKSLWAGVVVLLLLQGGSAYKLVCYFTNWSQDRQEPGKFTPENIDPFLCSHLI

YSFASIENNKVIIKDKSEVMLYQTINSLKTKNPKLKILLSIGGYLFGSKGFHPMVDSSTS

RLEFINSIILFLRNHNFDGLDVSWIYPDQKENTHFTVLIHELAEAFQKDFTKSTKERLLL

TAGVSAGRQMIDNSYQVEKLAKDLDFINLLSFDFHGSWEKPLITGHNSPLSKGWQDRGPS

SYYNVEYAVGYWIHKGMPSEKVVMGIPTYGHSFTLASAETTVGAPASGPGAAGPITESSG

FLAYYEICQFLKGAKITRLQDQQVPYAVKGNQWVGYDDVKSMETKVQFLKNLNLGGAMIW

SIDMDDFTGKSCNQGPYPLVQAVKRSLGSL
```

-continued

FAM117B
(UniProtKB Q6P1L5, SEQ ID NO: 64)
MSQRVRRNGSPTPAGSLGGGAVATAGGPGSRLQPMRATVPFQLKQQQQQQHGSPTRSGGG

GGGNNNGGCCGGASGPAGGGGGGGPRTASRSTSPTRGGGNAAARTSPTVATQTGASATST

RGTSPTRSAAPGARGSPPRPPPPPPLLGTVSSPSSSPTHLWTGEVSAAPPPARVRHRRRS

PEQSRSSPEKRSPSAPVCKAGDKTRQPSSSPSSIIRRTSSLDTLAAPYLAGHWPRDSHGQ

AAPCMRDKATQTESAWAEEYSEKKKGSHKRSASWGSTDQLKEIAKLRQQLQRSKHSSRHH

RDKERQSPFHGNHAAINQCQAPVPKSALIPVIPITKSTGSRFRNSVEGLNQEIEIIIKET

GEKEEQLIPQDIPDGHRAPPPLVQRSSSTRSIDTQTPGGADRGSNNSSRSQSVSPTSFLT

ISNEGSEESPCSADDLLVDPRDKENGNNSPLPKYATSPKPNNSYMFKREPPEGCERVKVF

EECSPKQLHEIPAFYCPDKNKVNFIPKSGSAFCLVSILKPLLPTPDLTLKGSGHSLTVTT

GMTTILLQPIAVASLSTNTEQDRVSRGTSTVMPSASLLPPPEPIEEAEG

LPAR5
(UniProtKB Q9H1C0, SEQ ID NO: 65)
MLANSSSINSSVLPCPDYRPTHRLHLVVYSLVLAAGLPLNALALWVFLRALRVHSVVSVY

MCNLAASDLLFTLSLPVRLSYYALHHWPFPDLLCQTTGAIFQMNMYGSCIFLMLINVDRY

AAIVHPLRLRHLRRPRVARLLCLGVWALILVFAVPAARVHRPSRCRYRDLEVRLCFESFS

DELWKGRLLPLVLLAEALGFLLPLAAVVYSSGRVFWTLARPDATQSQRRRKTVRLLLANL

VIFLLCFVPYNSTLAVYGLLRSKLVAASVPARDRVRGVLMVMVLLAGANCVLDPLVYYFS

AEGFRNTLRGLGTPHRARTSATNGTRAALAQSERSAVTTDATRPDAASQGLLRPSDSHSL

SSFTQCPQDSAL

NFATC1
(UniProtKB O95644, SEQ ID NO: 66)
MPSTSFPVPSKFPLGPAAAVFGRGETLGPAPRAGGTMKSAEEEHYGYASSNVSPALPLPT

AHSTLPAPCHNLQTSTPGIIPPADHPSGYGAALDGGPAGYFLSSGHTRPDGAPALESPRI

EITSCLGLYHNNNQFFHDVEVEDVLPSSKRSPSTATLSLPSLEAYRDPSCLSPASSLSSR

SCNSEASSYESNYSYPYASPQTSPWQSPCVSPKTTDPEEGFPRGLGACTLLGSPRHSPST

SPRASVTEESWLGARSSRPASPCNKRKYSLNGRQPPYSPHHSPTPSPHGSPRVSVTDDSW

LGNTTQYTSSAIVAAINALTTDSSLDLGDGVPVKSRKTTLEQPPSVALKVEPVGEDLGSP

PPPADFAPEDYSSFQHIRKGGFCDQYLAVPQHPYQWAKPKPLSPTSYMSPTLPALDTQLP

SHSGPYELRIEVQPKSHHRAHYETEGSRGAVKASAGGHPIVQLHGYLENEPLMLQLFIGT

ADDRLLRPHAFYQVHRITGKTVSTTSHEAILSNTKVLEIPLLPENSMRAVIDCAGILKLR

NSDIELRKGETDIGRKNTRVRLVFRVHVPQPSGRTLSLQVASNPIECSQRSAQELPLVEK

QSTDSYPVVGGKKMVLSGHNFLQDSKVIFVEKAPDGHHVWEMEAKTDRDLCKPNSLVVEI

PPFRNQRITSPVHVSFYVCNGKRKRSQYQRFTYLPANVPIIKTEPTDDYEPAPTCGPVSQ

GLSPLPRPYYSQQLAMPPDPSSCLVAGFPPCPQRSTLMPAAPGVSPKLHDLSPAAYTKGV

ASPGHCHLGLPQPAGEAPAVQDVPRPVATHPGSPGQPPPALLPQQVSAPPSSSCPPGLEH

SLCPSSPSPPLPPATQEPTCLQPCSPACPPATGRPQHLPSTVRRDESPTAGPRLLPEVHE

DGSPNLAPIPVTVKREPEELDQLYLDDVNEIIRNDLSSTSTHS

RBM38
(UniProtKB Q9H0Z9, SEQ ID NO: 68)
MLLQPAPCAPSAGFPRPLAAPGAMHGSQKDTTFTKIFVGGLPYHTTDASLRKYFEGFGDI

EEAVVITDRQTGKSRGYGFVTMADRAAAERACKDPNPIIDGRKANVNLAYLGAKPRSLQT

GFAIGVQQLHPTLIQRTYGLTPHYIYPPAIVQPSVVIPAAPVPSLSSPYIEYTPASPAYA

QYPPATYDQYPYAASPATAASFVGYSYPAAVPQALSAAAPAGTTFVQYQAPQLQPDRMQ

-continued

SGPP1
(UniProtKB Q9BX95, SEQ ID NO: 69)
MSLRQRLAQLVGRLQDPQKVARFQRLCGVEAPPRRSADRREDEKAEAPLAGDPRLRGRQP

GAPGGPQPPGSDRNQCPAKPDGGGAPNGVRNGLAAELGPASPRRAGALRRNSLTGEEGQL

ARVSNWPLYCLFCFGTELGNELFYILFFPFWIWNLDPLVGRRLVVIWVLVMYLGQCTKDI

IRWPRPASPPVVKLEVFYNSEYSMPSTHAMSGTAIPISMVLLTYGRWQYPLIYGLILIPC

WCSLVCLSRIYMGMHSILDIIAGFLYTILILAVFYPFVDLIDNFNQTHKYAPFIIIGLHL

ALGIFSFTLDTWSTSRGDTAEILGSGAGIACGSHVTYNMGLVLDPSLDTLPLAGPPITVT

LFGKAILRILIGMVFVLIIRDVMKKITIPLACKIFNIPCDDIRKARQHMEVELPYRYITY

GMVGFSITFFVPYIFFFIGIS

SLC6A16
(UniProtKB Q9GZN6, SEQ ID NO: 70)
MKTEAQPSTSLLANTSWTGTVISDSVPGSQTWEDKGSLTRSATSWTSEAQVSAARVAEAQ

ARTSQPKQISVLEALTASALNQKPTHEKVQMTEKKESEVLLARPFWSSKTEYILAQVGFS

MKPSCLWRFAYLWLNSGGCSFAAIYIFMLFLVGVPLLFLEMAAGQSMRQGGMGVWKIIAP

WIGGVGYSSFMVCFILGLYFNVVNSWIIFYMSQSFQFPVPWEKCPLIMNSSGFDPECERT

TPSIYFWYQQALKASDRIEDGGSPVYSLVLPFFLCWCLVGAFMINGLKSTGKVIYVLVLL

PCFIIVGFFIRTLLLEGAKFGLQQLVVAKISDVYNMSVWSLAGGQVLSNTGIGLGSVASL

ASYMPQSNNCLSDAFLVSVINLLTLLVFTSFNFCVLGFWATVITHRCCERNAEILLKLIN

LGKLPPDAKPPVNLLYNPTSIYNAWLSGLPQHIKSMVLREVTECNIETQFLKASEGPKFA

FLSFVEAMSFLPPSVFWSFIFFLMLLAMGLSSAIGIMQGIITPLQDTFSFFRKHTKLLIV

GVFLLMFVCGLFFTRPSGSYFIRLLSDYWIVFPIIVVVVFETMAVSWAYGARRFLADLTI

LLGHPISPIFGWLWPHLCPVVLLIIFVTMMVHLCMKPITYMSWDSSTSKEVLRPYPPWAL

LLMITLFAIVILPIPAYFVYCRIHRIPFRPKSGDGPMTASTSLPLSHQLTPSKEVQKEEI

LQVDETKYPSTCNVTS

According to the methods provided herein, the likelihood that a particular individual (e.g., a patient) is likely to respond to treatment with an anti-CD37 immunoconjugate (e.g., IMGN529) can be determined by detecting the expression level of at least one of the genes listed in Table 7 and comparing the expression level of the gene to a reference expression level. For example, as noted above, the reference expression level may be the median expression level of the at least one gene in a group/population of patients being tested for responsiveness to an anti-CD37 immunoconjugate (e.g., IMGN529). In some instances, the reference expression level is the expression level of the at least one gene in a non-cancerous sample from the same patient or unrelated individuals. In some instances, the reference expression level is the expression level of the at least one gene in a sample previously obtained from the individual at a prior time.

The subjects/patients may be informed that they have an increased likelihood of being responsive to treatment with an anti-CD37 immunoconjugate (e.g., IMGN529) and/or provided a recommendation that anti-cancer therapy include an anti-CD37 immunoconjugate (e.g., IMGN529). The gene expression level can be determined using at least one of the genes as described herein, or any combination of the genes as described herein (e.g., mean, weighted mean, or median) using methods known in the art and described in, e.g., Sokal R. R. and Rholf, F. J. (1995) "Biometry: the principles and practice of statistics in biological research," W. H. Freeman and Co. New York, N.Y.

In some instances, an increased expression level of at least one gene selected from the group consisting of: BASP1, CXCR5, BIK, LY86, TLR10, CD86, LCK, CD22, PTPN22, BCL6, PIK3IP1, CDKN2A, CD79A, CHI3L2, FAM117B, LPAR5, NFATC1, PTPN22, RBM38, SGPP1, and SLC6A16, indicates that a patient with GCB DLBCL is likely to respond to an anti-CD37 immunoconjugate therapy.

In some instances, an increased expression level of at least one gene selected from the group consisting of: AFF3, PIM1, MGMT, PDE4B, NFKBIE, SYK, FOXO1, CD79A, CHI3L2, FAM117B, LPAR5, NFATC1, PTPN22, RBM38, SGPP1, and SLC6A16 indicates that a patient with ABC DLBCL is likely to respond to an anti-CD37 immunoconjugate therapy.

In some instances, an absence of an increased expression level (e.g., a decreased expression level) of at least one gene selected from the group consisting of: CD44, VIM, ANXA2, BCL2, ANXA2P1, HSP90B1, NFKBIZ, CDK6, BIRC5, HEBP1, PHB, PSME3, RNU6-15, and RPL13 indicates that a patient with a GCB DLBCL is likely to respond to an anti-CD37 immunoconjugate therapy.

In some instances, an absence of an increased expression level of at least one gene selected from the group consisting of: HSPA1B, HSP90AA1, CADM1, CD86, TUBB2A, TUBG1, NOTCH1, HEBP1, PHB, PSME3, RNU6-15, and RPL13 indicates that a patient with ABC DLBCL is likely to respond to an anti-CD37 immunoconjugate therapy.

In one instance, this invention provides a method of identifying whether a patient with cancer will respond to treatment with an anti-CD37 immunoconjugate (e.g., IMGN529), comprising assessing the expression level of at least one of the genes listed in Table 7 in a sample from the patient obtained before the anti-CD37 immunoconjugate (e.g., IMGN529) is administered to the patient. An increase or an absence of an increase (e.g. a decrease) in the expression of at least one of the genes relative to a reference level (see above) indicates that the patient will respond to treatment with an anti-CD37 immunoconjugate (e.g., IMGN529). The patient can be informed that they have an increased likelihood of responding to treatment with an anti-CD37 immunoconjugate (e.g., IMGN529) and/or provided a recommendation that anti-cancer therapy include an anti-CD37 immunoconjugate (e.g., IMGN529).

In another instance, the methods provided herein for identifying the sensitivity or responsiveness of a patient to a anti-CD37 immunoconjugate (e.g., IMGN529) comprise assessing gene expression of at 1, 2, 3, 4, 5, 6, 7, 8, 9, 10, 11, 12, 13, 14, 15, 16, 17, 18, 19, 20, 21, 22, 23, 24, 25, 26, 27, or 28 gene(s) selected from the group consisting of: BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CD79A, CHI3L2, FAM117B, LPAR5, NFATC1, PTPN22, RBM38, SGPP1, and SLC6A16 in a cancer sample obtained from the patient and predicting the sensitivity or responsiveness of the patient to the anti-CD37 immunoconjugate (e.g., IMGN529), wherein an increase in the expression of at least 1, 2, 3, 4, 5, 6, 7, 8, 9, 10, 11, 12, 13, 14, 15, 16, 17, 18, 19, 20, 21, 22, 23, 24, 25, 26, 27, or 28 of the genes correlates with sensitivity or responsiveness of the patient to effective treatment with the anti-CD37 immunoconjugate (e.g., IMGN529).

In another instance, the method comprises assessing gene expression of at 1, 2, 3, 4, 5, 6, 7, 8, 9, 10, 11, 12, 13, 14, 15, 16, 17, 18, 19, 20, or 21 gene(s) selected from the group consisting of: CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13 from a cancer sample and predicting the sensitivity or responsiveness of the patient to the anti-CD37 immunoconjugate (e.g., IMGN529), wherein an absence of an increased expression level (e.g., a decreased expression level) of at least 1, 2, 3, 4, 5, 6, 7, 8, 9, 10, 11, 12, 13, 14, 15, 16, 17, 18, 19, 20, or 21 of the genes correlates with sensitivity or responsiveness of the patient to effective treatment with the anti-CD37 immunoconjugate (e.g., IMGN529).

The present invention further provides a method of identifying a gene (e.g., DNA, RNA, or protein) whose expression level is predictive of the sensitivity or responsiveness of a particular patient to an anti-CD37 immunoconjugate (e.g., IMGN529), comprising: (a) measuring the expression level of a candidate gene (e.g., DNA, RNA, or protein) in a panel of cells that displays a range of sensitivities to an anti-CD37 immunoconjugate (e.g., IMGN529), and (b) identifying a correlation between the expression level of, seropositivity for, or presence of said candidate gene (e.g., DNA, RNA, or protein) in the cells and the sensitivity or responsiveness of the cells to the anti-CD37 immunoconjugate (e.g., IMGN529), wherein the correlation indicates that the expression level, seropositivity, or presence of said biomarker is predictive of the responsiveness of a patient to treatment by the anti-CD37 immunoconjugate (e.g., IMGN529). In one instance of this method the panel of cells is a panel of samples prepared from samples derived from patients or experimental animal models. In an additional instance the panel of cells is a panel of cell lines in mouse xenografts.

In some instances, the expression level of a gene is analyzed by assessing the amount of a DNA, RNA, or protein. In some instances, the expression level of a gene is analyzed by assessing the activity of a gene (e.g., protein).

A cancer sample can be taken from a patient who is suspected of having, or is diagnosed as having a cancer, and hence is likely in need of treatment. A reference sample can be taken from a normal individual who is not suspected of having any disorder. For assessment of marker expression, samples, such as those containing cells, or proteins or nucleic acids produced by these cells, can be used in the methods of the present invention. In the methods of this invention, the level of a gene (e.g., DNA, RNA, or protein) can be determined by assessing the amount (e.g., the absolute amount or concentration) of the markers in a cancer sample. The cancer sample may be frozen, fresh, fixed (e.g., formalin fixed), centrifuged, and/or embedded (e.g., paraffin embedded), etc. The cancer sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the expression level of the gene in the sample. Likewise, biopsies can also be subjected to post-collection preparative and storage techniques, e.g., fixation.

A. Detection of Gene Expression Levels

The expression levels of the genes described herein can be detected using any method known in the art. For example, tissue or cell cancer samples from mammals can be conveniently assayed for, e.g., mRNAs or DNAs from a gene of interest using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art. In an illustrative instance of the invention, a method for detecting mRNA of a gene of interest in a cancer sample comprises producing cDNA from the sample by reverse transcription using at least one primer; amplifying the cDNA so produced; and detecting the presence of the amplified cDNA. In addition, such methods can include one or more steps that allow one to determine the levels of mRNA in a cancer sample (e.g., by simultaneously examining the levels a comparative control mRNA sequence of a "housekeeping" gene such as an Actin family member). Optionally, the sequence of the amplified cDNA can be determined.

1. Detection of Nucleic Acids

In another specific instance, expression of the genes as described herein can be performed by RT-PCR technology. Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of expressed genes set forth in Table 7 in a sample. As will be understood by the skilled artisan, a great many different primers and probes may be prepared and used effectively to amplify, clone and/or determine the presence and/or levels expressed of one or more of the genes listed in Table 7.

Other methods include protocols that examine or detect mRNAs from at least one of the genes listed in Table 7 in a tissue or cell sample by microarray technologies. Using nucleic acid microarrays or nucleotide microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment (see, e.g., WO 2001/75166). See, for example, U.S. Pat. Nos. 5,700,637, 5,445,934, and 5,807,522, Lockart, Nature Biotechnology 14:1675-1680 (1996); and Cheung et al., Nature Genetics 21 (Suppl):15-19 (1999) for a discussion of array fabrication.

In addition, the DNA profiling and detection method utilizing microarrays described in EP 1753878 may be employed. This method rapidly identifies and distinguishes between different DNA sequences utilizing short tandem repeat (STR) analysis and DNA microarrays. In an instance, a labeled STR target sequence is hybridized to a DNA microarray carrying complementary probes. These probes vary in length to cover the range of possible STRs. The labeled single-stranded regions of the DNA hybrids are selectively removed from the microarray surface utilizing a post-hybridization enzymatic digestion. The number of repeats in the unknown target is deduced based on the pattern of target DNA that remains hybridized to the microarray.

One example of a microarray processor is the Affymetrix GENECHIP® system, which is commercially available and comprises arrays fabricated by direct synthesis of oligonucleotides on a glass surface. Other systems may be used as known to one skilled in the art. Another example of a microarray processor is Illumina example of a microarray processor is Illumina BeadArray technology, which is also commercially available and is utilized in Illumina array products and array scanners for a broad range of DNA and RNA analysis applications, for example, Illumina HumanHT-12 Expression BeadChips. Expression of RNA can also be assessed using EdgeSeq technology from HTG Molecular.

Other methods for determining the level of the gene include quantitative PCR, semi-quantitative PCR, or RNase protection assay, as well as individualized genetic profiles that are necessary to treat cancer based on patient response at a molecular level. The specialized microarrays herein, e.g., oligonucleotide microarrays or cDNA microarrays, can comprise one or more genes having expression profiles that correlate with either sensitivity or resistance to an anti-CD37 immunoconjugate. Other methods that can be used to detect nucleic acids, for use in the invention, involve high throughput RNA sequence expression analysis, including RNA-based genomic analysis, such as, for example, RNASeq. RNA-Seq, also called whole transcriptome shotgun sequencing (WTSS), uses a variety of next-generation sequencing techniques to study RNA. A review of the RNA-Seq technology is provided in Chu Y, Corey DR (2012), RNA sequencing: platform selection, experimental design, and data interpretation. *Nucleic Acid Ther.* 22(4): 271-4.

Many references are available to provide guidance in applying the above techniques (Kohler et al., Hybridoma Techniques (Cold Spring Harbor Laboratory, New York, 1980); Tijssen, Practice and Theory of Enzyme Inimunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982); and Zola, Monoclonal Antibodies: A Manual of Techniques, pp. 147-158 (CRC Press, Inc., 1987)). Northern blot analysis is a conventional technique well known in the art and is described, for example, in Molecular Cloning, a Laboratory Manual, second edition, 1989, Sambrook, Fritch, Maniatis, Cold Spring Harbor Press, 10 Skyline Drive, Plainview, N.Y. 11803-2500. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis).

2. Detection of Proteins

As to detection of protein such as a protein corresponding to at least one of the genes listed in Table 7, for example, various protein assays are available including, for example, antibody-based methods as well as mass spectroscopy and other similar means known in the art. In the case of antibody-based methods, for example, the cancer sample can be contacted with an antibody specific for said gene under conditions sufficient for an antibody-protein complex to form, and then detecting said complex. Detection of the presence of the protein can be accomplished in a number of ways, such as by Western blotting (with or without immunoprecipitation), 2-dimensional SDS-PAGE, immunoprecipitation, fluorescence activated cell sorting (FACS), flow cytometry, cytofluorometry, protein microarray, immunoassay, mass spectrometry, dot blot, in situ hybridization, and ELISA procedures for assaying a wide variety of tissues and samples, including plasma or serum. A wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g., 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the cancer sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule," as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e., radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest Immunofluorescence and EIA techniques are both very well established in the art. However, other reporter molecules, such as radioisotope, chemiluminescent or bioluminescent molecules, may also be employed.

B. Kits

For use in detection of the genes (e.g., DNA, RNA, or protein), kits or articles of manufacture are also provided by the invention. Such kits can be used to determine if a subject with cancer will be effectively responsive to an anti-CD37 immunoconjugate (e.g., IMGN529). These kits may comprise a carrier means being compartmentalized to receive in close confinement one or more container means such as vials, tubes, and the like, each of the container means comprising one of the separate compounds or elements to be used in the method. For example, one of the container means may comprise a probe that is or can be detectably labeled. Such probe can be a polypeptide (e.g., an antibody) or polynucleotide specific for a protein or message, respectively. Where the kit utilizes nucleic acid hybridization to detect the target nucleic acid, the kit can also have containers containing nucleotide(s) for amplification of the target nucleic acid sequence and/or a container comprising a reporter-means, such as a biotin-binding protein, e.g., avidin or streptavidin, bound to a reporter molecule, such as an enzymatic, florescent, or radioisotope label.

Such kit will typically comprise the container described above and one or more other containers comprising materials desirable from a commercial and user standpoint, including buffers, diluents, filters, needles, syringes, and package inserts with instructions for use. A label can be present on the container to indicate that the composition is used for a specific application, and can also indicate directions for either in vivo or in vitro use, such as those described above.

A typical instance is a kit comprising a container, a label on said container, and a composition contained within said container, wherein the composition includes a primary antibody that binds to a protein, and the label on said container indicates that the composition can be used to evaluate the presence of such proteins in a cancer sample, and wherein the kit includes instructions for using the antibody for evaluating the presence of proteins in a particular sample type. The kit can further comprise a set of instructions and materials for preparing a sample and applying antibody to the sample. The kit may include both a primary and secondary antibody, wherein the secondary antibody is conjugated to a label, e.g., an enzymatic label.

Another instance is a kit comprising a container, a label on said container, and a composition contained within said container, wherein the composition includes one or more polynucleotides that hybridize to a complement of a gene as described herein under stringent conditions, and the label on said container indicates that the composition can be used to evaluate the presence of a gene as described herein in a sample, and wherein the kit includes instructions for using the polynucleotide(s) for evaluating the presence of RNA or DNA in a particular sample type.

Other optional components of the kit include one or more buffers (e.g., block buffer, wash buffer, substrate buffer, etc.), other reagents such as substrate (e.g., chromogen) that is chemically altered by an enzymatic label, epitope retrieval solution, control samples (positive and/or negative controls), control slide(s), etc. Kits can also include instructions for interpreting the results obtained using the kit.

In further specific instances, for antibody-based kits, the kit can comprise, for example: (1) a first antibody (e.g., attached to a solid support) that binds to a protein; and, optionally, (2) a second, different antibody that binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples that can be assayed and compared to the test sample. Each component of the kit can be enclosed within an individual container and all of the various containers can be within a single package, along with instructions for interpreting the results of the assays performed using the kit.

In some instances, the kit comprises (a) polypeptides or polynucleotides capable of determining the expression level of at least one gene selected from the group consisting of: BASP1, CXCR5, BIK, LY86, TLR10, CD86, LCK, CD22, PTPN22, BCL6, PIK3IP1, CDKN2A, AFF3, PIM1, MGMT, PDE4B, NFKBIE, SYK, FOXO1, CD79A, CHI3L2, FAM117B, LPAR5, NFATC1, PTPN22, RBM38, SGPP1, and SLC6A16, (b) instructions for use of such polypeptides or polynucleotides to determine the expression levels of the at least one gene, and (c) instructions for use of the polypeptides or polynucleotides to compare the expression level of the at least one gene to a reference expression level of the at least one gene; wherein an increase in the expression level of the at least one gene relative to a reference expression level indicates that the patient may benefit from treatment with an anti-CD37 immunoconjugate. In other instances, the kit comprises (a) polypeptides or polynucleotides capable of determining the expression level of at least one gene selected from the group consisting of: CD44, VIM, ANXA2, BCL2, ANXA2P1, HSP90B1, NFKBIZ, CDK6, BIRC5, HSPA1B, HSP90AA1, CADM1, CD86, TUBB2A, TUBG1, NOTCH1, HEBP1, PHB, PSME3, RNU6-15, and RPL13, (b) instructions for use of such polypeptides or polynucleotides to determine the expression levels of the at least one gene, and (c) instructions for use of the polypeptides or polynucleotides to compare the expression level of the at least one gene to a reference expression level of the at least one gene; wherein an absence of increase in the expression level (e.g. a decrease in the expression level) of the at least one gene relative to a reference expression level indicates that the patient may benefit from treatment with an anti-CD37 immunoconjugate.

In other instances, the kit of this invention can be a combination diagnostic and pharmaceutical kit which comprises any or all of the above-mentioned components and an anti-CD37 immunoconjugate (e.g., IMGN529).

C. Statistics

As used herein, the general form of a prediction rule consists in the specification of a function of one or multiple genes potentially including clinical covariates to predict response or non-response, or more generally, predict benefit or lack of benefit in terms of suitably defined clinical endpoints.

The simplest form of a prediction rule consists of a univariate model without covariates, wherein the prediction is determined by means of a cutoff or threshold. This can be phrased in terms of the Heaviside function for a specific cutoff c and a biomarker measurement x, where the binary prediction A or B is to be made, then if H $(x-c)=0$, then predict A, if H $(x-c)=1$, then predict B.

This is the simplest way of using univariate biomarker measurements in prediction rules. If such a simple rule is sufficient, it allows for a simple identification of the direction of the effect, i.e., whether high or low expression levels are beneficial for the patient.

The situation can be more complicated if clinical covariates need to be considered and/or if multiple biomarkers are used in multivariate prediction rules. The two hypothetical examples below illustrate the issues involved:

Covariate Adjustment (Hypothetical Example):

For a gene X it is found in a clinical trial population that high expression levels are associated with a worse clinical response (univariate analysis). A closer analysis shows that there are two types of clinical response in the population, a first group which possesses a worse response than the second group and at the same time the gene expression for the first group is generally higher following administration of at least one dose of an anti-CD37 immunoconjugate (e.g., IMGN529). An adjusted covariate analysis reveals that for each of the groups the relation of clinical benefit and clinical response is reversed, i.e., within the groups, lower expression levels are associated with better clinical response. The overall opposite effect was masked by the covariate type—and the covariate adjusted analysis as part of the prediction rule reversed the direction.

Multivariate Prediction (Hypothetical Example):

For a gene X it is found in a clinical trial population that high expression levels are slightly associated with a worse clinical response (univariate analysis). For a second biomarker Y a similar observation was made by univariate analysis. The combination of X and Y revealed that a good clinical response is seen if both biomarkers are low. This makes the rule to predict benefit if both biomarkers are below some cutoffs (AND—connection of a Heaviside prediction function). For the combination rule, a simple rule no longer applies in a univariate sense; for example, having low expression levels in X will not automatically predict a better clinical response.

These simple examples show that prediction rules with and without covariates cannot be judged on the univariate level of each gene. The combination of multiple genes plus a potential adjustment by covariates does not allow assigning simple relationships to single gene. Since the marker genes, in particular in serum, can be used in multiple-marker prediction models potentially including other clinical covariates, the direction of a beneficial effect of a single marker gene within such models cannot be determined in a simple way, and may contradict the direction found in univariate analyses, i.e., the situation as described for the single marker gene.

Statistical methods commonly used in the field, including but not limited to the ones described in the Examples, were also used herein. Examples of Statistical methods include Gene Set Enrichment Analysis (GSEA) and limma t-test.

GSEA is a computational method that determines whether an a priori defined set of genes shows statistically significant, concordant differences between two biological states (e.g. phenotypes). GSEA software is available at http://software.broadinstitute.org/gsea/index.jsp. Limma is an R/Bioconductor software package that provides an integrated solution for analyzing data from gene expression experiments. Principles and features of the limma package are described in Ritchie M E, et al., (2015), limma powers differential expression analyses for RNA-Seq (RNA-sequencing) and microarray studies. Nucleic Acids Res. 43(7): e47.

IV. Treatment with Anti-CD37 Immunoconjugates

The anti-CD37 immunoconjugates (e.g., IMGN529) provided herein are useful in a variety of applications including, but not limited to, therapeutic treatment methods, such as the treatment of cancer, such as CD37-expressing cancers, e.g., B-cell malignancies. In certain instances, the agents are useful for inhibiting tumor growth, inducing differentiation, reducing tumor volume, and/or reducing the tumorigenicity of a tumor. The methods of use can be in vivo methods.

In certain instances, the dosage is from about 0.1 to 3.0 mg of the anti-CD37 immunoconjugate (e.g., IMGN529) per kg of body weight (mg/kg). In certain instances, the dosage of the immunojugate is from 0.4 to 0.8 mg per kg of body weight. In certain instances, the dosage of the immunoconjugate is from 0.8 to 1.4 mg per kg of body weight. In certain instances, the dosage of the immunoconjugate is from 0.8 to 1.2 mg per kg of body weight. In certain instances, the dosage of the immunoconjugate is from 1.0 to 3.0 mg per kg of body weight. In certain instances, the dosage of the immunoconjugate is from 1.0 to 2.8 mg per kg of body weight. In certain instances, the dosage of the immunoconjugate is from about 1.0 to about 1.4 mg per kg of body weight. In certain instances, the dosage of the immunoconjugate is from about 1.4 to about 2.0 mg per kg of body weight. In certain instances, the dosage of immunoconjugate is from about 1.4 to about 3.0 mg per kg of body weight. In certain instances, the dosage of the immunoconjugate is from about 1.4 to about 2.8 mg per kg of body weight. In certain instances, the dosage of the immunoconjugate is from about 2.0 to about 2.8 mg per kg of body weight. In certain instances, the dosage of the immunoconjugate is from about 2.0 to about 3.0 mg per kg of body weight. In certain instances, the dosage of immunoconjugate is about 0.1 per kg of body weight. In certain instances, the immunoconjugate is about 0.2 mg per kg of body weight. In certain instances, the dosage of the immunoconjugate is about 0.3 mg per kg of body weight. In certain instances, the dosage of immunoconjugate is about 0.4 mg per kg of body weight. In certain instances, the dosage of the immunoconjugate is about 0.5 mg per kg of body weight. In certain instances, the dosage of the immunoconjugate is about 0.6 mg per kg of body weight. In certain instances, the dosage of the immunoconjugate is about 0.7 mg per kg of body weight. In certain instances, the dosage of the immunoconjugate is about 0.8 mg per kg of body weight. In certain instances, the dosage of the immunoconjugate is about 0.9 mg per kg of body weight. In certain instances, the dosage of the immunoconjugate is about 1.0 mg per kg of body weight. In certain instances, the dosage of the immunoconjugate is about 1.1 mg per kg of body weight. In certain instances, the dosage of the immunoconjugate is about 1.2 mg per kg of body weight. In certain instances, the dosage of the immunoconjugate is about 1.3 mg per kg of body weight. In certain instances, the dosage of the immunoconjugate is about 1.4 mg per kg of body weight. In certain instances, the dosage of the immunoconjugate is about 1.5 mg per kg of body weight. In certain instances, the dosage of the immunoconjugate is about 1.6 mg per kg of body weight. In certain instances, the dosage of the immunoconjugate is about 1.7 mg per kg of body weight. In certain instances, the dosage of the immunoconjugate is about 1.8 mg per kg of body weight. In certain instances, the dosage of the immunoconjugate is about 1.9 mg per kg of body weight. In certain instances, the dosage of the immunoconjugate is about 2.0 mg per kg of body weight. In certain instances, the dosage of immunoconjugate is about 2.1 mg per kg of body weight. In certain instances, the dosage of the immunoconjugate is about 2.2 mg per kg of body weight. In certain instances, the dosage of the immunoconjugate is about 2.3 mg per kg of body weight. In certain instances, the dosage of the immunoconjugate is about 2.4 mg per kg of body weight. In certain instances, the dosage of the immunoconjugate is about 2.5 mg per kg of body weight. In certain instances, the dosage of the immunoconjugate is about 2.6 mg per kg of body weight. In certain instances, the dosage of the immunoconjugate is about 2.7 mg per kg of body weight. In certain instances, the dosage of the immunoconjugate is about 2.8 mg per kg of body weight. In certain instances, the dosage of the immunoconjugate is about 2.9 mg per kg of body weight. In certain instances, the dosage of the immunoconjugate is about 3.0 mg per kg of body weight.

In certain instances, the dosage of the immunoconjugate is about 0.7 mg/kg and the immunoconjugate is administered every three weeks. In certain instances, the dosage of the immunoconjugate is about 1.0 mg/k and the immunoconjugate is administered every three weeks. In certain instances, the dosage of the immunoconjugate is about 1.4 mg/kg and the immunoconjugate is administered every three weeks (e.g., wherein G-CSF is also administered).

In certain instances, the disease treated with the anti-CD37 immunoconjugate (e.g., IMGN529) is a cancer. In certain instances, the cancer is characterized by CD37 expressing cells to which the anti-CD37 immunoconjugate binds.

The present invention provides for methods of treating cancer comprising administering a therapeutically effective amount of an anti-CD37 immunoconjugate (e.g., IMGN529) to a subject (e.g., a subject in need of treatment). In certain instances, the cancer is a B-cell malignancy. In certain instances, the cancer is a T-cell malignancy. In certain instances, the cancer is leukemia or lymphoma. In certain instances, the cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), small cell lymphoma, B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL). In certain instances, the cancer is selected from the group consisting of diffuse large B cell lymphoma (DLBCL) (including but not limited to activated B cell like diffuse large B-cell lymphoma (ABC-DLBCL) and germinal center B cell like diffuse B-cell lymphoma (GCB-DLBCL), follicular lymphoma (FL), unspecified NHL, MALT lymphoma, mantle cell lymphoma (MCL), Burkitt's lymphoma (BL), chronic lymphocytic leukemia (CLL), and primary mediastinal large B-cell lymphoma (PMBCL). In certain instances, the cancer is relapsed or refractory NHL. In certain instances, the subject is a human.

In certain instances, the method of treating cancer comprises administering a therapeutically effective amount of an anti-CD37 immunoconjugate (e.g., IMGN529) to a subject (e.g., a subject in need of treatment), wherein the administration decreases in the size or volume of one or more tumors or lesions, or in the extent of cancer in the body by at least 30%.

In certain instances, the method of inhibiting tumor growth comprises administering to a subject a therapeutically effective amount of an anti-CD37 immunoconjugate (e.g., IMGN529). In certain instances, the subject is a human. In certain instances, the subject has a tumor or has had a tumor removed.

In addition, the invention provides a method of reducing the tumorigenicity of a tumor in a subject, comprising administering a therapeutically effective amount of an anti-CD37 immunoconjugate (e.g., IMGN529) to the subject. In certain instances, the tumor comprises cancer stem cells. In certain instances, the frequency of cancer stem cells in the tumor is reduced by administration of the agent.

A clinician may use any of several methods known in the art to measure the effectiveness of a treatment with an anti-CD37 immunoconjugate (e.g., IMGN529). For example, in vivo imaging (e.g., MRI) can be used to determine the tumor size and to identify any metastases to determine relative effective responsiveness to the therapy.

The present invention further provides pharmaceutical compositions comprising one or more of the anti-CD37 immunoconjugates (e.g., IMGN529) described herein. In certain instances, the pharmaceutical compositions further comprise a pharmaceutically acceptable vehicle. These pharmaceutical compositions find use in inhibiting tumor growth and treating cancer in human patients.

In certain instances, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, succinate and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions for use as provided herein can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. In some instances, the administration is intravenous.

In some instances, the methods further comprise administering a corticosteroid to the patient. In some instances the corticosteroid can be selected from the group consisting of prednisone, prednisolone, methylprednisolone, beclamethasone, betamethasone, dexamethasone, fludrocortisone, hydrocortisone, and triamcinolone. In some instances, the corticosteroid can be dexamethasone. In some instances, the corticosteroid can be administered as a pre-treatment, i.e., prior to the administration of the anti-CD37 immunoconjugate. In some instances, the corticosteroid can be administered during the administration of the anti-CD37 immunoconjugate. In some instances, the corticosteroid can be administered during the administration of the anti-CD37 immunoconjugate and at least one additional time from about one day after to about five days after the administration of the anti-CD37 immunoconjugate. In some instances, the corticosteroid can be administered during the administration of the anti-CD37 immunoconjugate and at least one additional time from about one day after to about four days after the administration of the anti-CD37 immunoconjugate. In some instances, the corticosteroid can be administered during the administration of the anti-CD37 immunoconjugate and at least one additional time from about one day after to about three days after the administration of the anti-CD37 immunoconjugate. In some instances, the corticosteroid can be administered during the administration of the anti-CD37 immunoconjugate and at least one additional time from about one day after to about two days after the administration of the anti-CD37 immunoconjugate. In some instances, the corticosteroid can be administered during the administration of the anti-CD37 immunoconjugate and at least one additional time from about two days after to about five days after the administration of the anti-CD37 immunoconjugate. In some instances, the corticosteroid can be administered during the administration of the anti-CD37 immunoconjugate and at least one additional time from about two days after to about four days after the administration of the anti-CD37 immunoconjugate. In some instances, the corticosteroid can be administered during the administration of the anti-CD37 immunoconjugate and at least one additional time from about two days after to about three days after the administration of the anti-CD37 immunoconjugate. In some instances, the corticosteroid can be administered during the administration of the anti-CD37 immunoconjugate and at about two days after and at about three days after the administration of the anti-CD37 immunoconjugate. In some instances, the corticosteroid can be administered during the administration of the anti-CD37 immunoconjugate and at about two days after and at about three days after the administration of the anti-CD37 immunoconjugate. In some instances, the corticosteroid can be administered by peri-infusion. In some instances, the corticosteroid is administered 30 to 60 minutes prior to administration of the anti-CD37 immunoconjugate. In some instances, the corticosteroid is administered 30 to 60 minutes prior to administration of the anti-CD37 immunoconjugate and on at least one additional time on days 1 to 3 following administration of the anti-CD37 immunoconjugate. Pre-infusion intravenous steroid administration was found to eliminate hematological adverse effects. In some instances, the corticosteroid is administered on at least one of days 2 and 3 following infusion. In some instances, the corticosteroid is administered by IV 30 to 60 minutes prior to administration of the anti-CD37 immunoconjugate and orally on days 2 and 3 following infusion.

In some instances the corticosteroid is administered by IV. In some instances the steroid is administered orally.

In some instances, the corticosteroid is administered intravenously 30 to 60 minutes prior to the administration of the anti-CD37 immunoconjugate (e.g., IMGN529) and the corticosteroid is administered orally on days 2 and 3 of a 3-week anti-CD37 immunoconjugate (e.g., IMGN529) administration cycle.

In some instances the corticosteroid to be administered can be dexamethasone. In some instances the corticosteroid to be administered can be methylprednisolone. In some instances the corticosteroid to be administered can be prednisolone.

In some instances, from about 5 mg to about 10 mg dexamethasone is administered. In some instances, from about 8 mg to about 10 mg dexamethasone is administered. In some instances, about 10 mg dexamethasone is administered. In some instances, about 8 mg dexamethasone is administered. In some instances about 10 mg dexamethasone is administered by IV 30 to 60 minutes prior to administration of the anti-CD37 immunoconjugate. In some instances about 10 mg dexamethasone is administered by IV at the time of administration of the anti-CD37 immunoconjugate and again about 1 to about 5 days after administration of the anti-CD37 immunoconjugate. In some instances, the corticosteroid is administered by IV 30 to 60 minutes prior to administration of the anti-CD37 immunoconjugate and one dose of 8 mg of dexamethasone is delivered orally on days 2 and 3 following infusion.

In some instances, 10 mg dexamethasone is administered intravenously 30 to 60 minutes prior to the administration of the anti-CD37 immunoconjugates (e.g., IMGN529) and 8 mg dexamethasone is administered orally on days 2 and 3 of a 3-week anti-CD37 immunoconjugate (e.g., IMGN529) administration cycle.

In some instances, the methods further comprise administering a growth factor to the patient. Methods of administering white blood cell growth factors are reviewed, for example, in Smith et al., *J. Clin. Oncol.* 24: 3187-3205 (2006), which is herein incorporated by reference in its entirety. Growth factor treatment may decrease the likelihood of neutropenias. In some instances, the growth factor can be granulocyte colony-stimulating factor (G-CSF). In some instances the growth factor can be granulocyte-macrophage colony-stimulating factor (GM-CSF). In some instances the growth factor can be macrophage colony-stimulating factor (M-CSF). In some instances, the growth factor can be filgrastim. In some instances, the growth factor can be pegylated, e.g., pegylated G-CSF. In some instances, the growth factor can be pegfilgrastim, marketed as Neulasta®.

In some instances, the growth factor can be administered as a pre-treatment, i.e., prior to the administration of the anti-CD37 immunoconjugate. In some instances, the anti-CD37 immunoconjugate is administered on a 3-week (about 21-day) cycle and the growth factor can be administered at any point during the 3-week (about 21-day) cycle. In some instances, the anti-CD37 immunoconjugate is administered on a 3-week (about 21-day) cycle and the growth factor can be administered early to middle cycle of the 3-week (about 21-day) cycle. In some instances, the growth factor can be administered on at least one day from day 1 to about day 21 of the 3-week (about 21-day) cycle. In some instances, the growth factor can be administered on at least one day from day 1 to about day 20 of the 3-week (about 21-day) cycle. In some instances, the growth factor can be administered on at least one day from day 1 to about day 19 of the 3-week (about 21-day) cycle. In some instances, the growth factor can be administered on at least one day from day 1 to about day 18 of the 3-week (about 21-day) cycle. In some instances, the growth factor can be administered on at least one day from day 1 to about day 17 of the 3-week (about 21-day) cycle. In some instances, the growth factor can be administered on at least one day from day 1 to about day 16 of the 3-week (about 21-day) cycle. In some instances, the growth factor can be administered on at least one day from day 1 to about day 14 of the 3-week (about 21-day) cycle. In some instances, the growth factor can be administered on at least one day from day 1 to about day 12 of the 3-week (about 21-day) cycle. In some instances, the growth factor can be administered on at least one day from day about 15 to about day 21 of the 3-week (about 21-day) cycle. In some instances, the growth factor can be administered on at least one day from about day 3 to about day 10 of the 3-week (about 21-day) cycle. In some instances, the growth factor can be administered at least twice from about day 3 to about day 10 of the 3-week (about 21-day) cycle. In some instances, the growth factor can be administered at least three times from about day 3 to about day 10 of the 3-week (about 21-day) cycle. In some instances, the growth factor can be administered on at least one day from about day 4 to about day 10 of the 3-week (about 21-day) cycle. In some instances, the growth factor can be administered on at least one day from day 5 to day 8 of the 3-week (about 21-day) cycle. In some instances, the growth factor can be administered on at least one day selected from day 5, day 6, and day 8 of the 3-week (about 21-day) cycle. In some instances, the growth factor can be administered on days 5, 6, and 8 of the 3-week (about 21-day) cycle.

In some instances, G-CSF is administered at a dose of about 1 μg/kg body weight to about 15 μg/kg body weight, per day that the growth factor is administered. In some instances, G-CSF is administered at a dose of about 5 μg/kg/day. In some instances, G-CSF is administered at a dose of about 10 μg/kg/day.

In some instances, G-CSF is administered at a dose of about 200 μg to about 600 μg per day. In some instances, G-CSF is administered at a dose of about 300 μg to about 500 μg per day. In some instances, G-CSF is administered at a dose of about 300 μg to about 480 μg per day. In some instances, G-CSF is administered at a dose of about 300 μg/day. In some instances, G-CSF is administered at a dose of about 400 μg/day. In some instances, G-CSF is administered at a dose of about 480 μg/day. In some instances, G-CSF is administered at a dose of about 500 μg/day.

In some instances, GM-CSF is administered at a dose of about 100 μg/m² to about 500 μg/m², per day that the growth factor is administered. In some instances, GM-CSF is administered at a dose of about 250 μg/m²/day.

In some instances, GM-CSF is administered at a dose of about 200 μg to about 600 μg per day. In some instances, GM-CSF is administered at a dose of about 300 μg to about 500 μg per day. In some instances, GM-CSF is administered at a dose of about 300 μg to about 480 μg per day. In some instances, GM-CSF is administered at a dose of about 300 μg/day. In some instances, G-CSF is administered at a dose of about 400 µg/day. In some instances, GM-CSF is administered at a dose of about 480 µg/day. In some instances, GM-CSF is administered at a dose of about 500 µg/day.

In some instances, pegfilgrastim is administered at a dose of about 6 mg per cycle. In some instances, pegfilgrastim is administered at a dose of about 10 µg/kg to about 500 µg/kg per cycle. In some instances, pegfilgrastim is administered at a dose of about 10 µg/kg to about 400 µg/kg per cycle. In some instances, pegfilgrastim is administered at a dose of about 50 µg/kg to about 300 µg/kg per cycle. In some instances, pegfilgrastim is administered at a dose of about 50 µg/kg to about 200 µg/kg per cycle. In some instances, pegfilgrastim is administered at a dose of about 50 µg/kg to about 150 µg/kg per cycle. In some instances, pegfilgrastim is administered at a dose of about 100 µg/kg per cycle.

In some instances, administration of corticosteroids and/or G-CSF to the dosing protocol allows a higher dose of the CD37 immunoconjugate to be administered. In some instances, patients stay on the treatment longer due to the administration of corticosteroids and/or G-CSF. In some instances, less neutropenia is observed due to the administration of corticosteroids and/or G-CSF. In some instances, more clinical benefits are observed due to the administration of corticosteroids and/or G-CSF.

Anti-CD37 immunoconjugates that specifically bind to CD37 and methods of administering thereof are described in published U.S. patent applications, including U.S. Publication No. 2011/0256153, U.S. Publication No. 2012/0276119, U.S. Publication No. 2015/0093397, and U.S. Publication No. 2015/0343077, each of which is hereby incorporated by reference herein in its entirety.

Instances of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and instances described herein are for illustrative purposes only and that various modifications or changes in light thereof will be suggested to persons skilled in the art and are to be included within the spirit and purview of this application.

Example 1. Identification of Anti-Lymphoma Biomarkers of Response to IMGN529

Fifty-four lymphoma cell lines (ALCL, anaplastic large cell lines (n=5); CLL, chronic lymphocytic leukemia (n=2); ABC-DLBCL, activated B cell like diffuse large B cell (n=7); GCB-DLBCL, germinal center B cell like diffuse large B cell (n=20); MCL, mantle cell lymphoma (n=10); MZL, marginal zone lymphoma (n=6); PMBCL, Primary Mediastinal Large B-Cell Lymphoma (n=1); SMZL, splenic marginal zone lymphoma (n=3)) were exposed to increasing doses of IMGN529 or to the unconjugated cytotoxic payload DM1 for 72 hours. Cell proliferation was measured using the MTT assay. Apoptosis induction was defined by at least a 1.5-fold increase in caspase 3/7 signal activation with respect to controls using the Promega ApoTox-Glo Triplex Assay. CD37 surface expression was assessed by cytofluorimetry. Gene expression profiling (GEP) was done with the Illumina HumanHT-12 Expression BeadChips on untreated cell lines followed by GSEA (NES>|2|, P<0.05, FDR<0.25) and limma t-test (FC>|1.2|; P<0.05; top 200 up and top 200 down).

The IMGN529 median IC50 in the fifty-four cell lines was 790 pM (95% C.I., 250 pm-7.9 nM). Activity was stronger (P<0.001) in B cell lymphoma cell lines (n=46; median IC50=450 pM; 95% C.I., 150-780 pM) than in T cell lymphoma cell lines (n=8; median IC50=22.5 nM; 95% C.I., 14-40 nM). The median IC50 for DM1 was 30 pM (C.I.95%, 20-40 pM) with no differences between B and T cell lymphoma origin (FIG. 1). IMGN529 induced apoptosis in 33/54 (61%) lymphoma cell lines. Surface CD37 expression was higher in cell lines derived from B than from T cells (P<0.0001). IMGN529 IC50 values, but not of DM1, were negatively correlated with surface CD37 expression across all cell lines (R=−0.36; P=0.01), but not within the individual B or T cell subgroups.

Among B cell lines, DLBCL cell of origin, TP53 status, or the presence of BCL2 translocation did not affect the sensitivity to IMGN529, while IC50s were higher in the presence of MYC translocation (P=0.01). No association was seen between IMGN529-induced apoptosis or the sensitivity to DM1 with DLBCL cell of origin, TP53 status, or the presence of BCL2 or MYC translocations.

Figure 2A:
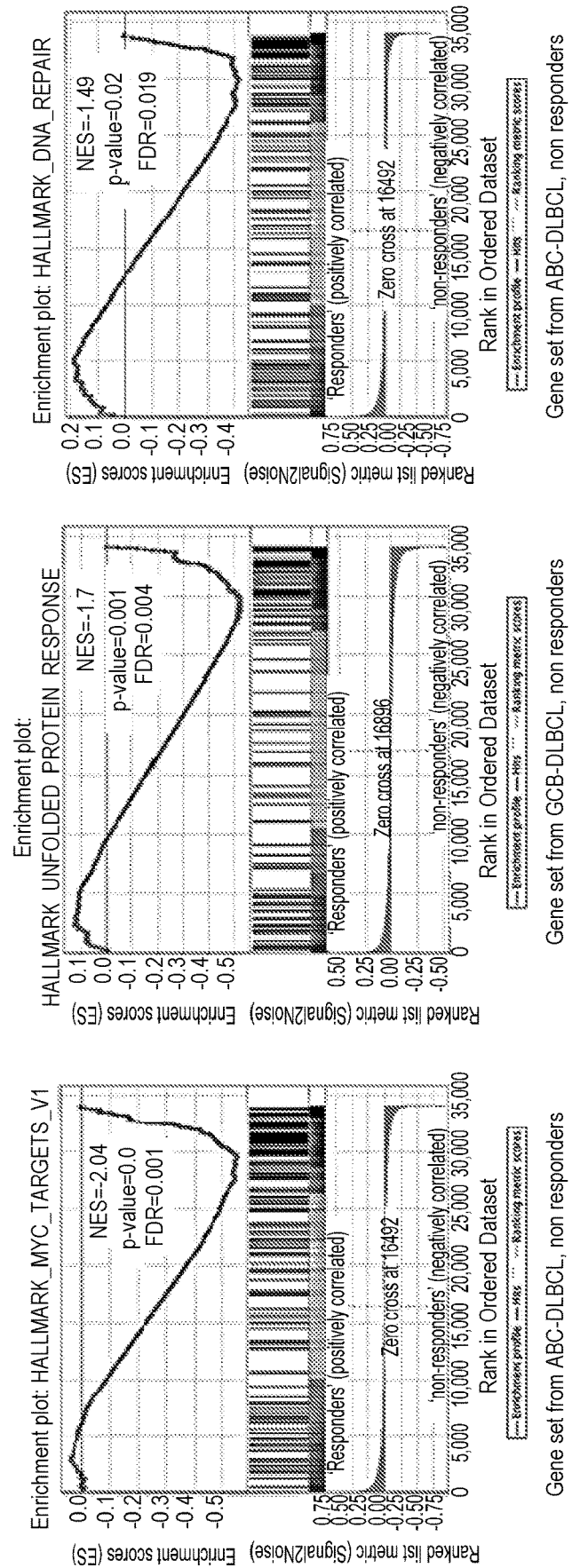
FIG. 2A shows that transcripts of genes involved in the unfolded protein response, glycolysis, MYC targets, and DNA repair, are enriched in resistant ("R") DLBCL cell lines ($IC_{50} \geq 3$ nM; or $IC_{50} > 10$ nM for GCB cell lines).
Figure 2B:
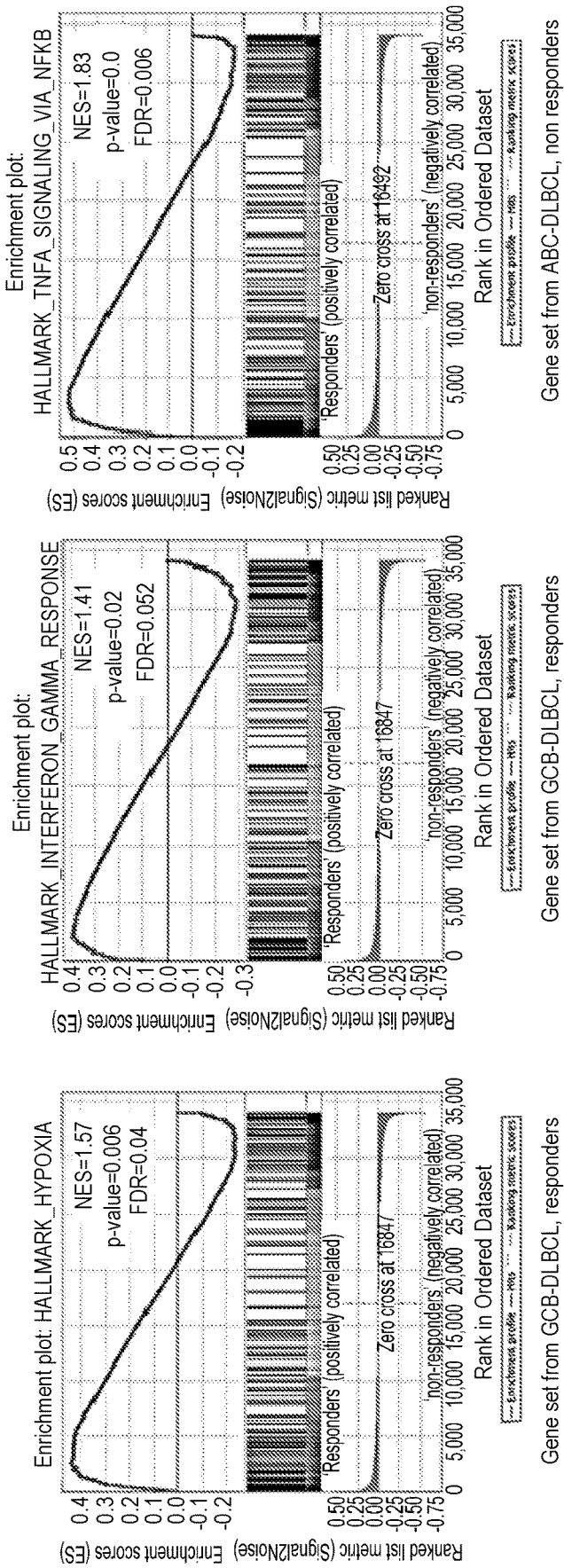
FIG. 2B shows that transcripts of genes involved in the PI3K/AKT/mTOR pathway, hypoxia, INF-gamma response, and TNFA signaling via NFKB pathways are enriched in sensitive ("S") DLBCL cell lines ($IC_{50} < 800$ pM or $\leq 800$ pM).

The baseline gene expression profiling of DLBCL cell lines that were highly sensitive to IMGN529 (IC50<0.8 nM; "S") versus less sensitive/resistant DLBCL cell lines (IC50>3 nM or >10 nM, "R") was compared, separately for germinal center B cell type (GCB) (S, n=11; R, n=8) and for activated B cell like (ABC) (S, n=4; R, n=3). Gene Set Enrichment Analysis (GSEA) and limma t-test were used in the statistical analysis of mRNA expression versus response status of the cell lines. In both DLBCL groups combined, MYC targets, genes involved in unfolded protein response, glycolysis and DNA repair were enriched in transcripts more expressed in R than S cell lines (FIG. 2A). Transcripts associated with low sensitivity or resistance included CD44, VIM, ANXA2, BCL2, ANXA2P1, HSP90B1, NFKBIZ, CDK6, BIRC5 in GCB and HSPA1B, HSP90AA1, CADM1, CD86, TUBB2A, TUBG1, NOTCH1 in ABC cell lines. HEBP1, PHB, PSME3, RNU6-15, RPL13 were more expressed in both GCB and ABC R. Genes involved in PI3K/AKT/mTOR, hypoxia, INF-gamma response, TNFA signaling via NFKB, and in complement were more expressed in S than in R cell lines (FIG. 2B). Genes associated with sensitivity to IMGN529 comprised: CD37 (IMGN529 target), CD79A, CHI3L2, FAM117B, LPAR5, NFATC1, PTPN22, RBM38, SGPP1, SLC6A16 in both GCB and ABC cell lines; BASP1, CXCR5, BIK, LY86, TLR10, CD86, LCK, CD22, PTPN22, BCL6, PIK3IP1, CDKN2A in GCB; AFF3, PIM1, MGMT, PDE4B, NFKBIE, SYK, FOXO1 in ABC.

The results from these experiments showed IMGN529 having very strong anti-tumoral activity in pre-clinical lymphoma models. High expression of CD37 and mostly genes involved in BCR signaling were associated with sensitivity to IMGN529. Conversely, the presence of MYC translocation, a high expression of MYC targets, and of genes involved in drug resistance (BCL2, BIRC5, CDK6, heat-shock proteins, annexins, proteasome, and tubulin components) appeared to negatively affect the response to IMGN529. These results represent therapeutic targets for combinations to be explored.

What is claimed is:

1. A method for treating a B cell cancer in a patient comprising administering an anti-CD37 immunoconjugate to the patient, wherein an increased expression level has been detected in a cancer sample obtained from the patient for at least one gene selected from the group consisting of: SLC6A16, CD79A, CHI3L2, FAM117B, LPAR5, NFATC1, PTPN22, RBM38, and SGPP1;
wherein the anti-CD37 immunoconjugate has the formula (A)-(L)-(M), wherein:
(A) is an antibody or antigen-binding fragment thereof that specifically binds to CD37 and comprises heavy and light chain variable region CDR sequences of SEQ ID NOs: 4-6 and SEQ ID NOs: 7-9, respectively;
(L) is a linker; and
(M) is a maytansinoid; and
wherein the linker (L) links (A) to (M).

2. The method of claim 1, wherein an increased expression level of CD37 has also been detected in a cancer sample from the patient.

3. The method of claim 1, wherein an increased expression level of at least 2 genes selected from the group consisting of: SLC6A16, CD79A, CHI3L2, FAM117B, LPAR5, NFATC1, PTPN22, RBM38, and SGPP1, has been detected in a cancer sample obtained from the patient.

4. The method of claim 1, wherein the immunoconjugate comprises an antibody or antigen-binding fragment thereof having the variable heavy chain sequence of SEQ ID NO: 12 and the variable light chain sequence of SEQ ID NO: 15 or having the variable heavy chain sequence of SEQ ID NO: 22 and the variable light chain sequence of SEQ ID NO: 15.

5. The method of claim 1, wherein the maytansinoid is DM1 or DM4.

6. The method of claim 1, wherein the linker in the immunoconjugate is SMCC.

7. The method of claim 1, wherein the immunoconjugate comprises an antibody or antigen-binding fragment thereof having the variable heavy chain sequence of SEQ ID NO: 12 and the variable light chain sequence of SEQ ID NO: 15, the cytotoxic agent DM1, and the linker SMCC.

8. The method of claim 1, wherein the immunoconjugate comprises an antibody or antigen-binding fragment thereof having the full-length heavy chain amino acid sequence of SEQ ID NO: 18 and the full-length light chain amino acid sequence of SEQ ID NO: 21, the cytotoxic agent DM1, and the linker SMCC.

9. The method of claim 1, further comprising detecting the expression level in the cancer sample obtained from the patient prior to administering the immunoconjugate.

10. The method of claim 1, wherein the detection method is cytofluorometry, flow cytometry, protein microarray, immunoassay, mass spectrometry, fluorescence activated cell sorting (FACS), ELISA, SDS-PAGE, dot blot, nucleotide microarray, quantitative PCR, semi-quantitative PCR, RNase protection assay, in situ hybridization, or RNA-Seq.

11. The method of claim 1, wherein the increased expression has been detected by comparing the expression level of the at least one gene to the expression level of at least one reference gene selected from the group consisting of: ACTB, GAPDH, GUSB, HPRT1, and 18S rRNA.

12. The method of claim 11, wherein the increased expression is an increase that is at least 1.5-fold greater than the change in expression level of the reference gene.

13. The method of claim 1, wherein the increased expression level is increased mRNA.

14. The method of claim 1, wherein the increased expression level is increased protein.

15. The method of claim 1, wherein the cancer sample is tissue, blood, plasma, bone marrow, or lymph.

16. The method of claim 1 further comprising administering a corticosteroid to the patient.

17. The method of claim 16, wherein the corticosteroid is administered prior to the administration of the immunoconjugate, or the corticosteroid is administered during the administration of the immunoconjugate.

18. The method of claim 17, wherein the corticosteroid is administered from about 30 to about 60 minutes prior to administration of the immunoconjugate.

19. The method of claim 1 further comprising administering a growth factor to the patient.

20. The method of claim 1, wherein the B cell cancer is a lymphoma.

21. The method of claim 1, wherein the B cell cancer is a diffuse large B-cell lymphoma (DLBCL.

22. The method of claim 1, wherein the B cell cancer is an activated B cell like diffuse large B-cell lymphoma (ABC-DLBCL).

23. The method of claim 1, wherein the B cell cancer is a germinal center B cell like diffuse B-cell lymphoma (GCB-DLBCL).

24. The method of claim 7, wherein the B cell cancer is a diffuse large B-cell lymphoma (DLBCL).

25. The method of claim 7, wherein the B cell cancer is an activated B cell like diffuse large B-cell lymphoma (ABC-DLBCL).

26. The method of claim 7, wherein the B cell cancer is a germinal center B cell like diffuse B-cell lymphoma (GCB-DLBCL).

* * * * *

UNITED STATES PATENT AND TRADEMARK OFFICE
CERTIFICATE OF CORRECTION

| | |
|---|---|
| PATENT NO. | : 11,278,629 B2 |
| APPLICATION NO. | : 16/346905 |
| DATED | : March 22, 2022 |
| INVENTOR(S) | : Francesco Bertoni et al. |

It is certified that error appears in the above-identified patent and that said Letters Patent is hereby corrected as shown below:

In the Claims

In Column 227, Claim 21, Line 4, delete "(DLBCL." and insert -- (DLBCL). --, therefor.

Signed and Sealed this
Twenty-fourth Day of May, 2022

Katherine Kelly Vidal
*Director of the United States Patent and Trademark Office*